United States Patent
Dehart et al.

(10) Patent No.: US 12,331,076 B2
(45) Date of Patent: Jun. 17, 2025

(54) ALPHAVIRUS-BASED REPLICONS FOR ADMINISTRATION OF BIOTHERAPEUTICS

(71) Applicant: Janssen Pharmaceuticals, Inc., Titusville, NJ (US)

(72) Inventors: Jason L. Dehart, San Diego, CA (US); Nathaniel Stephen Wang, San Diego, CA (US); Parinaz Aliahmad, San Diego, CA (US); Shigeki Miyake-Stoner, La Jolla, CA (US); Kurt Iver Kamrud, Olathe, KS (US)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 930 days.

(21) Appl. No.: 16/595,980

(22) Filed: Oct. 8, 2019

(65) Prior Publication Data

US 2020/0109178 A1    Apr. 9, 2020

Related U.S. Application Data

(60) Provisional application No. 62/742,868, filed on Oct. 8, 2018.

(51) Int. Cl.
    *C07K 14/005*      (2006.01)
    *C12N 7/00*      (2006.01)
    *A61K 38/00*      (2006.01)

(52) U.S. Cl.
    CPC .............. *C07K 14/005* (2013.01); *C12N 7/00* (2013.01); *A61K 38/00* (2013.01); *C12N 2770/36122* (2013.01); *C12N 2770/36133* (2013.01); *C12N 2770/36143* (2013.01)

(58) Field of Classification Search
    None
    See application file for complete search history.

(56) References Cited

U.S. PATENT DOCUMENTS

| | | | |
|---|---|---|---|
| 4,727,138 A | 2/1988 | Goeddel |
| 4,738,927 A | 4/1988 | Taniguchi |
| 4,762,791 A | 8/1988 | Goeddel |
| 4,810,643 A | 3/1989 | Souza |
| 4,892,743 A | 1/1990 | Leibowitz |
| 4,966,843 A | 10/1990 | Mccormick |
| 4,999,291 A | 3/1991 | Souza |
| 5,017,691 A | 5/1991 | Lee |
| 5,116,742 A | 5/1992 | Cech |
| 5,225,337 A | 7/1993 | Robertson |
| 5,246,921 A | 9/1993 | Reddy |
| 5,780,036 A | 7/1998 | Chisari |
| 5,958,060 A | 9/1999 | Premerlani |
| 6,041,252 A | 3/2000 | Walker |
| 6,110,161 A | 8/2000 | Mathiesen |
| 6,117,660 A | 9/2000 | Walters |
| 6,224,879 B1 | 5/2001 | Mathilda |
| 6,261,281 B1 | 7/2001 | Mathiesen |
| 6,273,525 B1 | 8/2001 | Erban |
| 6,278,895 B1 | 8/2001 | Bernard |
| 6,319,901 B1 | 11/2001 | Bernard |
| 6,697,669 B2 | 2/2004 | Dev |
| 6,873,549 B2 | 3/2005 | Khalid |
| 6,873,849 B2 | 3/2005 | De La Red |
| 6,912,417 B1 | 6/2005 | Bernard |
| 6,939,862 B2 | 9/2005 | Bureau |
| 6,958,060 B2 | 10/2005 | Mathiesen |
| 6,982,087 B2 | 1/2006 | Johnston |
| 7,328,064 B2 | 2/2008 | Mathiesen |
| 7,419,674 B2 | 9/2008 | Chulay |
| 7,664,545 B2 | 2/2010 | Westersten |
| 7,850,977 B2 | 12/2010 | Kamrud |
| 8,080,255 B2 | 12/2011 | Smith |
| 8,187,249 B2 | 5/2012 | Bernard |
| 8,209,006 B2 | 6/2012 | Smith |
| 8,216,589 B2 | 7/2012 | Yum |
| 8,859,198 B2 | 10/2014 | Bartholomeusz |

(Continued)

FOREIGN PATENT DOCUMENTS

| | | |
|---|---|---|
| JP | H10500017 | 1/1998 |
| JP | 2007537761 A | 12/2007 |

(Continued)

OTHER PUBLICATIONS

Boukhebza et al., "Comparative analysis of immunization schedules using a novel adenovirus-based immunotherapeutic targeting hepatitis B in naive and tolerant mouse models" Vaccine, 32(26), pp. 3258-3263, 2014.

Jones et al., "Hepatitis B virus reverse transcriptase: diverse functions as classical and emerging targets for antiviral intervention", Emerging Microbes and Infections, 2(9), e56, 9 pages, 2013.

Int'l Search Report and Written Opinion issued May 22, 2018 in Int'l Application No. PCT/IB2017/058142, 17 pages.

Obeng-Adjei et al. "DNA vaccine cocktail expressing genotype A and C HBV surface and consensus core antigens generates robust cytotoxic and antibody responses and mice and Rhesus macaques" Cancer Gene Therapy, 20, 352-662, 2013.

(Continued)

*Primary Examiner* — Benjamin P Blumel
(74) *Attorney, Agent, or Firm* — Ice Miller LLP

(57) ABSTRACT

The invention provides RNA replicons useful for administering a heterologous protein or peptide into a mammal and eliciting a reduced immune response or no immune response from the mammal. The RNA replicons have RNA sequences encoding for a heterologous protein or peptide, New World alphavirus nonstructural proteins nsP1, nsP2, and nsP4; and an alphavirus nsP3 protein macro domain, central domain, and hypervariable domain. The encoded hypervariable domain can have an amino acid sequence derived from an Old World alphavirus nsP3 hypervariable domain; or can have an amino acid sequence derived from a portion of a New World alphavirus n

(56) References Cited

U.S. PATENT DOCUMENTS

| | | |
|---|---|---|
| 8,961,995 B2 | 2/2015 | Frolov |
| 9,364,664 B2 | 6/2016 | Masterson |
| 9,452,285 B2 | 9/2016 | Draghia-Akli |
| 9,801,897 B2 | 10/2017 | Geall |
| 9,802,035 B2 | 10/2017 | Masterson |
| 10,538,786 B2 | 1/2020 | Kamrud |
| 11,020,476 B2 | 6/2021 | Boden |
| 11,021,692 B2 | 6/2021 | Boden |
| 11,185,688 B2 | 11/2021 | Hannaman |
| 2004/0213805 A1 | 10/2004 | Verheije |
| 2004/0235133 A1 | 11/2004 | Frolov |
| 2005/0070700 A1 | 3/2005 | Giese |
| 2005/0277605 A1 | 12/2005 | Wu |
| 2008/0279891 A1 | 11/2008 | Johnston |
| 2009/0018031 A1 | 1/2009 | Trinklein |
| 2009/0075384 A1 | 3/2009 | Kamrud |
| 2011/0110974 A1 | 5/2011 | Depla |
| 2012/0078161 A1 | 3/2012 | Masterson |
| 2012/0121650 A1 | 5/2012 | Johnston |
| 2014/0079734 A1 | 3/2014 | Frolov |
| 2014/0222105 A1 | 8/2014 | Broderick |
| 2015/0328404 A1 | 11/2015 | Murakami |
| 2016/0074500 A1 | 3/2016 | Pushko |
| 2016/0166678 A1 | 6/2016 | Kallen |
| 2016/0362472 A1 | 12/2016 | Bitter |
| 2017/0314043 A1 | 11/2017 | Kamrud |
| 2018/0104359 A1 | 4/2018 | Kamrud |
| 2018/0171340 A1 | 6/2018 | Kamrud |
| 2020/0164062 A1 | 5/2020 | Goh |

FOREIGN PATENT DOCUMENTS

| | | |
|---|---|---|
| WO | 8502862 | 7/1985 |
| WO | 8504188 | 9/1985 |
| WO | 9006370 | 6/1990 |
| WO | 9503777 A1 | 2/1995 |
| WO | 9531565 | 11/1995 |
| WO | 9637616 | 11/1996 |
| WO | 200224224 A2 | 3/2002 |
| WO | 2002042480 A2 | 5/2002 |
| WO | 2004055161 A2 | 7/2004 |
| WO | 2005087311 A1 | 9/2005 |
| WO | 2005113782 A1 | 12/2005 |
| WO | 2008093976 A1 | 8/2008 |
| WO | 2011015656 A2 | 2/2011 |
| WO | 2012087983 A1 | 6/2012 |
| WO | 2012109668 A1 | 8/2012 |
| WO | 2013007772 A1 | 1/2013 |
| WO | WO2013177133 * | 11/2013 |
| WO | 2014170493 | 10/2014 |
| WO | 2014170493 A2 | 10/2014 |
| WO | 2016020538 A1 | 2/2016 |
| WO | 2016054003 A1 | 4/2016 |
| WO | 2016184822 A1 | 11/2016 |
| WO | 2017024000 A1 | 2/2017 |
| WO | 2017172838 A1 | 10/2017 |
| WO | 2017176319 A1 | 10/2017 |
| WO | 2017180770 A1 | 10/2017 |
| WO | 2018075235 A1 | 4/2018 |
| WO | 2018106615 A1 | 6/2018 |
| WO | 2018225731 A1 | 12/2018 |
| WO | 2019099624 A1 | 5/2019 |
| WO | 2019123252 A1 | 6/2019 |

OTHER PUBLICATIONS

Cohen et al. "Is chronic hepatitis B being undertreated in the United States?" J. Viral Hepat., 18(6), 377-83,2011.

Belloni et al. "IFN-a inhibits HBV transcription and replication in cell culture and in humanized mice by targeting the epigenetic regulation of the nuclear cccDNA minichromosome" J. Clin. Invest., 122(2), 529-537, 2012.

World Health Organization, Hepatitis B: Fact sheet No. 204 [Internet] Mar. 2015. Available from https://www.who.int/news-room/fact-sheets/detail/hepatitis-b, 6 pages.

Michel et al. "Therapeutic vaccines and immune-based therapies for the treatment of chronic hepatitis B: perspectives and challenges." J. Hepatol., 54(6), 1286-1296, 2011.

Int'l Search Report and Written Opinion issued Apr. 17, 2019 in Int'l Application No. PCT/IB2018/060259, 16 pages.

Int'l Search Report and Written Opinion issued Jun. 25, 2018 in Int'l Application No. PCT/US2017/067269, 17 pages.

Int'l Search Report and Written Opinion issued Feb. 14, 2019 in Int'l Application No. PCT/US2018/066157, 19 pages.

Reyes-Sandoval Arturo et al, "Prime-Boost Immunization with Adenoviral and Modified Vaccinia Virus Ankara Vectors Enhances the Durability and Polyfunctionality of Protective Malaria CD8(+) T-Cell Responses", Infection and Immunity, (201001), vol. 78, No. 1, pp. 145-153, XP002778539.

Perrine Martin et al, "TG1050, an immunotherapeutic to treat chronic hepatitis B, induces robust T cells and exerts an antiviral effect in HBV-persistent mice", Gut, UK, (Nov. 26, 2014), vol. 64, No. 12, doi:10.1136/gutjnl-2014-308041, ISSN 0017-5749, pp. 1961-1971, XP055453477.

Bartenschlager et al., "Expression of the p. protein of the human hepatitis B virus in a vaccinia virus system and detection of the nucleocapsid-associated p. gene product by radiolabelling at newly introduced phosphorylation sites", Nucleic Acids Research, vol. 20, No. 2, pp. 195-202,1992.

Ramirez et al., "Biology of Attenuated Modified Vaccinia Virus Ankara Recombinant Vector in Mice: Virus Fate and Activation of B- and T-Cell Immune Responses in Comparision with the Western Reserve Strain and advantages as a Vaccine", Journal of Virology, Vo. 74, No. 2, pp. 923-933, 2000.

Int'l Search Report and Written Opinion issued Mar. 26, 2018 in Int'l Application No. PCT/IB2017058148, 14 pages.

Int'l Search Report and Written Opinion issued Mar. 27, 2019 in Int'l Application No. PCT/IB2018/060257, 15 pages.

Agapov et al., Noncytopathic Sindbis Virus RNA Vectors for Heterologous Gene Expression, Proc. Natl. Acad. Sci., 1998, pp. 12989-12994, vol. 95.

Altmann et al., Cotransfection of ICAM-1 and HLA-DR Reconstitutes Human Antigen-Presenting Cell Function in Mouse L Cells, Nature, 1989, pp. 512-514, vol. 338.

Altschul SF et al., "Basic Local Alignment Search Tool"; J. Mol. Biol. 215:403-410 (1990).

Atkins, G, et al. Therapeutic and Prophylactic Applications of Alphavirus Vectors, Expert Reviews in Molecular Medicine, Cambridge University Press, vol. 10, No. 1, pp. 1-18 (2008).

Attwood, T. The Babel of Bioinformatics, Science (2000) vol. 290, No. 5491, pp. 471-473 (Year: 2000).

Barbieri et al., Purification and partial characterization of another form of the antiviral protein from the seeds of *Phytolacca americana* L. (pokeweed), Biochem. J., 1982, pp. 55-59, vol. 203.

Barrette-Ng et al., Structure of Arterivirus nsp-4, J. Biol. Chem., 2002, pp. 39960-39966, vol. 277, Issue 42.

Beerens & Snijder, An RNA Pseudoknot in the 3' End of the Arterivirus Genome Has a Critical Role in Regulating Viral RNA Synthesis, J. Virol., 2007, pp. 9426-9436, vol. 81, Issue 17.

Berglund, P. et al., Enhancing Immune Response Using Suicidal DNA Vaccines,, Nature Biotechnology, vol. 16, pp. 562-565 (1998).

Besnard et al., Selection against expression of the *Escherichia coli* gene gpt in hprt+ mouse teratocarcinoma and hybrid cells, Mol. Cell. Biol., 1987, pp. 4139-4141, vol. 7.

Brakenhoff et al., Molecular cloning and expression of hybridoma growth factor in *Escherichia coli*, J. Immunol., Dec. 15, 1987, pp. 4116-4121, vol. 139, Issue 12.

Bzik et al., Molecular cloning and sequence analysis of the Plasmodium falciparum dihydrofolate reductase-thymidylate synthase gene, Proc. Natl. Acad. Sci. USA, Dec. 1987, pp. 8360-8364, vol. 84.

Calderwood et al., Nucleotide sequence of the Shiga-like toxin genes of *Escherichia coli*, Proc. Natl. Acad. Sci. USA, Jul. 1987, pp. 4364-4368, vol. 84.

Carroll and Collier, Active Site of Pseudomonas aeruginosa Exotoxin A, J. Biol. Chem., 1987, pp. 8707-8711, vol. 262.

(56) References Cited

OTHER PUBLICATIONS

Castillo-Olivares et al., Generation of a Candidate Live Marker Vaccine for Equine Arteritis Virus by Deletion of the Major Virus Neutralization Domain, J. Virol., 2003, pp. 8470-8480, vol. 77, Issue 15.
Chen et al., The complete primary structure of abrin-a B chain. FEBS Letters, 1992, pp. 115-118, vol. 309.
Cheng, W. et al. Enhancement of Sindbis Virus Self-Replicating RNA Vaccine Potency by Linkage of *Mycobacterium tuberculosis* Heat Shock Protein 70 Gene to an Antigen Gene, Journal of Immunology, vol. 166, pp. 6218-6226 (2001).
Chin et al., Tissue-specific Expression of Hepatic Functions Genetic Aspects, Ann. N.Y. Acad. Sci., Oct. 1986, pp. 120-130, vol. 478.
Collins et al., Primary Amino Acid Sequence of α-Trichosanthin and Molecular Models for Abrin A-chain and α-Trichosanthin, J. Biol. Chem., 1990, pp. 8665-8669, vol. 265.
Coussens et al., Tyrosine kinase receptor with extensive homology to EGF receptor shares chromosomal location with neu oncogene, Science, 1985, pp. 1132-1139, vol. 230.
Davis, N. et al., In Vitro Synthesis of Infectious Venezuelan Equine Encephalitis Virus RNA from a cDNA Clone: Analysis of a Viable Deletion Mutant' Virology, vol. 171, pp. 189-204 (1989).
De Vries et al., Genetic Manipulation of Equine Arteritis Virus Using Full-Length cDNA Clones: Separation of Overlapping Genes and Expression of a Foreign Epitope. Virology, 2000, pp. 84-97, vol. 270.
De Vries et al., Recombinant Equine Arteritis Virus Expression Vector, Virology, Jun. 5, 2001, pp. 259-276, vol. 284, Issue 2.
De Wilde et al., Cyclophilin Inhibitors Block Arterivirus Replication by Interfering with Viral RNA Synthesis, J. Virol., 2013, pp. 1454-1464, vol. 87, Issue 3.
Den Boon et al., Equine Arteritis Virus Subgenomic RNA Transcription: UV Inactivation and Translation Inhibition Studies, Virology, 1995, pp. 364-372, vol. 213.
Deng et al., Structural Basis for the Regulatory Function of a Complex Zinc-binding Domain in a Replicative Arterivirus Helicase Resembling a Nonsense-Mediated mRNA Decay Helicase, Nucl. Acids Res., 2013, pp. 3464-3477, vol. 42, Issue 5.
Ding et al., In Vivo Genome-Wide Profiling of RNA Secondary Structure Reveals Novel Regulatory Features, Nature, 2014, pp. 696-700 (and Methods), vol. 505.
Dowdy et al., Efficient Generation of Human iPSCs by a Synthetic Self-Replicative RNA, Cell Stem Cell, 2013, pp. 246-254, vol. 13.
Dubensky, T. et al. Sindbis Virus DNA-Based Expression Vectors: Utility for In Vitro and In Vivo Gene Transfer, Journal of Virology, vol. 70, No., 1, pp. 508-519 (1996).
Evensen et al., Direct Molecular Cloning and Expression of Two Distinct Abrin A-chains, J. Biol. Chem., Apr. 15, 1991, pp. 6848-6852, vol. 266, Issue 11.
Fainstein et al., Nucleotide sequence analysis of human abl and bcr-abl cDNAs, Oncogene, Dec. 1, 1989, pp. 1477-1481, vol. 4. Issue 12.
Faktor et al., The identification of hepatitis B virus X gene responsive elements reveals functional similarity of X and HTLV-I tax, Oncogene, Jun. 1, 1990, pp. 867-872, vol. 5, Issue 6.
Familletti et al., A convenient and rapid cytopathic effect inhibition assay for interferon, Methods in Enz., 1981, pp. 387-394, vol. 78.
Fang et al., Efficient-2 Frameshifting by Mammalian Ribosomes to Synthesize an Additional Arterivirus Protein, PNAS, 2012, pp. E2920-E2928.
Field et al., Isolation and Characterization of Acyclovir-Resistant Mutants of Herpes Simplex Virus, J. Genl. Virol., 1980, pp. 115-124, vol. 49.
Finter et al., The Use of Interferon-α in Virus Infections, Drugs, 1991, pp. 749-765, vol. 42.
Firth et al., Discovery of a Small Arterivirus Gene that Overlaps the GP5 Coding Sequence and is Important for Virus Production, J. Genl. Virol., 2011, pp. 1097-1106, vol. 92.

Frolov, I. et al. Cis-acting RNA elements at the 5' end of Sindbis virus genome RNA regulate minus- and plus-strand RNA synthesis, RNO, vol. 7, pp. 1638-1651 (2001).
Frolov, I et al., Translation of Sindbis Virus mRNA: analysis of sequences downstream of the initiating AUG codon that enhance translation. Journal of Virology, vol. 70, No. 2, pp. 1182-1190 (1996).
Frolov, I et al. Translation of Sindbis Virus mRNA: Effects of Sequences Downstream of the Initiating Codon, Journal of Virology, vol. 68, No. 12, pp. 8111-8117, (1994).
Gansbacher et al., Retroviral Vector-mediated γ-Interferon Gene Transfer into Tumor Cells Generates Potent and Long Lasting Antitumor Immunity, Cancer Res., Dec. 15, 1999, pp. 7820-7825, vol. 50.
Gansbacher et al., Interleukin 2 Gene Transfer into Tumor Cells Abrogates Tumorigenicity and Includes Protective Immunity, J. Ex. Med., The Rockefeller University Press, Oct. 1990, pp. 1217-1224, vol. 172.
Gibson et al., Enzymatic assembly of DNA molecules up to several hundred kilobases, Nature Methods, Apr. 12, 2009, pp. 343-345, vol. 6.
Maruggi Giulietta et al, "Engineered alphavirus replicon vaccines based on known attenuated viral mutants show limited effects on immunogenicity", Virology, (Oct. 5, 2013), vol. 447, No. 1, doi:10.1016/J.VIROL.2013.07.021, ISSN 0042-6822, pp. 254-264, XP028754361.
Glaser Al et al., An infectious cDNA clone of equine arteritis virus: a tool for future fundamental studies and vaccine development. Proceedings of the 8th International Conference on Equine Infectious Diseases, Dubai 1998; 1999, pp. 166-176.
Golumbek et al., Treatment of established renal cancer by tumor cells engineered to secrete interleukin-4, Science, Nov. 1, 1991, pp. 713-716, vol. 254.
Gorchakov, R. et al., Selection of Functional 5 cis-Acting Elements Promoting Efficient Sindbis Virus Genome Replication, Journal of Virology, vol. 78, No. 1, pp. 61-75 (2004).
Grabstein et al., Cloning of a T cell growth factor that interacts with the beta chain of the interleukin-2 receptor. Science, 1994, pp. 965-968, vol. 264.
Hardy, R. et al Requirements at the 3 End of the Sindbis Virus Genome for Efficient Synthesis of Minus-Strand RNA, Journal of Virology, pp. 4630-4639 (2005).
Hooper et al., Molecular Smallpox Vaccine Delivered by Alphavirus Replicons Elicits Protective Immunity in Mice and Non-Human Primates, Vaccine, 2009, pp. 494-511, vol. 28, Issue 2.
Horikawa et al., Molecular cloning and nucleotide sequence of cDNA encoding the human liver S-adenosylmethionine synthetase, Biochem. Intl., Sep. 1, 1991, pp. 81-90, vol. 25, Issue 1.
Hyde, J. et al., The 5' and 3' ends of alphavirus RNAs-non-coding is not non-functional, Virus Res., vol. 206, pp. 99-107 (2015).
Irvin JD, Purification and partial characterization of the antiviral protein from Phytolacca americana which inhibits eukaryotic protein synthesis, Arch. Biochem & Biophys, Aug. 1975, pp. 522-528, vol. 169, Issue 2.
Irvin JD, Pokeweed antiviral protein, Pharmac. Ther., 1983, pp. 371-387, vol. 21, Issue 3.
Irvin JD et al., Purification and properties of a second antiviral protein from Phytolacca americana which inactivates eukaryotic ribosomes, Arch. Biochem. & Biophys., Apr. 1, 1980, pp. 418-425, vol. 200, Issue 2.
Jackson et al., Nucleotide sequence analysis of the structural genes for Shiga-like toxin I encoded by bacteriophage 933J from *Escherichia coli*. Microb. Path., Feb. 1987, pp. 147-153, vol. 2, Issue 2.
Jayaraman et al., Enhancement of in vivo cell-mediated immune responses by three distinct cytokines, J. Immunol., 1990, pp. 942-951, vol. 144.
Kamrud et al., Alphavirus Replicon Approach to Promoterless Analysis of IRES Elements, Virology, 2007, pp. 376-387, vol. 360.
Karlin & Altschul, Applications and statistics for multiple high-scoring segments in molecular sequences Proc. Nat'l. Acad. Sci. USA 90:5873-87 (1993).

(56) References Cited

OTHER PUBLICATIONS

Karupiah et al., Elevated natural killer cell responses in mice infected with recombinant vaccinia virus encoding murine IL-2, J. Immunol., Jan. 1, 1990, pp. 290-298, vol. 144, Issue 1.
Kelly, B. et al. Potential of Alphavirus Vectors in the Treatment of Advanced Solid Tumors, Recent Patents on Anti-Drug Discovery, vol. 2, No. 2, pp. 159-166 (2007).
Kerr et al., Anti-penicillin-V-amidase conjugates kill antigen-positive tumor cells when combined with doxorubicin phenoxyacetamide, Cancer. Immunol. Immunother., 1990, pp. 202-206, vol. 31, Issue 4.
Kim et al. 2014. Enhancement of protein expression by alphavirus replicons by designing self-replicating subgenomic RNAs. Proceedings National Academy of Sciences, 111 (29):10708-10713.
Klimstra et al., Adaptation of Sindbis Virus to BHK Cells Selects for Use of Heparan Sulfate as an Attachment Receptor. J. Virol. 72: pp. 7357 (1988), 10 pages.
Kinney, R. et al., Attenuation of Venezuelan Equine Encephalitis Virus Strain TC-83 Is Encoded by the 5'-Noncoding Region and the E2 Envelope Glycoprotein, Journal of Virology, vol. 67, No. 3, pp. 1269-1277, (1993).
Knoops et al., Ultrastructural Characterization of Arterivirus Replication Structures: Reshaping the Endoplasmic Reticulum to Accommodate Viral RNA Synthesis, J. Virol., 2011, pp. 2474-2487, vol. 86, Issue 5.
Kofler R. et al., Mimicking live flavivirus immunization with a noninfectious RNA vaccine, PNAS, vol. 101, No. 7, pp. 1951-1956, (2004).
Kulasegaran-Shylini et al., Structural and Functional Elements of Promoter Encoded by the 5' Untranslated Region of the Venezuelan Equine Encephalitis Virus Genome J. Virol. 83:17 p. 8327-8339 (2009).
Kulasegaran-Shylini et al., The 5'UTR-specific mutation in VEEV TC-83 genome has a strong effect on RNA replication and subgenomic RNA synthesis, but not on translation of the encoded proteins. Virology, 387(1): 211-221 (2009).
Lamb et al., Nucleotide sequence of cloned cDNA coding for preproricin, Eur. J. Biochem., 1985, pp. 265-270, vol. 148.
Lee et al., Multiagent Vaccines Vectored by Venezuelan Equine Encephalitis Virus Replicon Elicits Immune Responses to Marburg Virus and Protection against Anthrax and Botulinum Neurotoxin in Mice, Vaccine, 2006, pp. 6886-6892, vol. 24.
Lehmann et al., Arterivirus nsp12 Versus the Coronavirus nsp16 2'-O-Methyltransferase: Comparison of the C-terminal Cleavage Products of Two Nidovirus pp1ab Polyproteins, J. Genl. Virol., 2015, pp. 2643-2655, vol. 96.
Lehmann et al., Arterivirus RNA-Dependent RNA Polymerase: Vital Enzymatic Activity remains Elusive, Virology, 2016, pp. 68-74, vol. 487.
Linsley et al., Binding of the B Cell activation antigen B7 to CD28 costimulates T cell proliferation and Interleukin 2 mRNA accumulation, J. Exp. Med., Mar. 1991, pp. 721-730, vol. 173.
Linsley et al., CTLA-4 Is a second receptor for the B Cell activation antigen B7, J. Exp. Med., Sep. 1991, pp. 561-570, vol. 174.
Luo, R., et al., Antiviral activity of type I and type III interferons against porcine reproductive and respiratory syndrome virus (PRRSV), Antiviral Research, vol. 91, pp. 99-101 (2011).
Maher and Dolinick, Specific hybridization arrest of dihydrofolate reductase mRNA in vitro using anti-sense RNA or anti-sense oligonucleotides, Arch. Biochem & Biophys., Feb. 15, 1987, pp. 214-220, vol. 253, Issue 1.
Maio, et al., Modulation by cytokines of HLA antigens, intercellular adhesion molecule 1 and high molecular weight melanoma associated antigen expression and of immune lysis of clones derived from the melanoma cell line MeM 50-10. Can. Immunol. Immunother., Jan. 1989, pp. 34-42, vol. 30, Issue 1.
Manolaridis, et al., Structure and Genetic Analysis of the Arterivirus Nonstructural Protein 7α, J. Virol., 2011, pp. 7449-7453, vol. 85, Issue 14.

McKnight et al., Deduced consensus sequence of Sindbis virus strain AR339: mutations contained in laboratory strains which affect cell culture and in vivo phenotypes. Virol. 70:1981 (1996), 9 pages.
McLoughlin, M. et al. Alphavirus infections in salmonids—a review, Journal of Fish Diseases, vol. 30, pp. 511-531 (2007).
Mekalanos et al., Cholera toxin genes: nucleotide sequence, deletion analysis and vaccine development, Nature, 1983, pp. 551-557, vol. 306.
Mogler, M. et al., RNA-based viral vectors, Expert Rev. Vaccines, pp. 1-30 (2014).
Molenkamp R et al, "The arterivirus replicase is the only viral protein required for genome replication and subgenomic mRNA transcription.", The Journal of General Virology Oct. 2000, (Oct. 2000), vol. 81, No. Pt 10, ISSN 0022-1317, pp. 2491-2496, XP002771366.
Molenkamp et al., Isolation and Characterization of an Arterivirus Defective Interfering RNA Genome, J. Virol., 2000, pp. 3156-3165, vol. 74, Issue 7.
Molenkamp et al., Characterization of an Arterivirus Defective Interfering RNA, 2001, pp. 519-525. In the Nidoviruses (Coronaviruses and Arteriviruses), Ehud Lavi et al. (ed.), Kluwer Academic/Plenum Publishers.
Mullen, Transfer of the bacterial gene for cytosine deaminase to mammalian cells confers lethal sensitivity to 5-fluorocytosine: A negative selection system, Proc. Natl. Acad. Sci. USA, Jan. 1992, pp. 33-37, vol. 89.
Muraggi, G et al. Engineered Alphavirus Replicon Vaccines Based on Known Attenuated Viral Mutants Show Limited Effects on Immunogenicity, Virology, vol. 44, pp. 254-264 (2013).
Nagata, et al., Synthesis in E. coli of a polypeptide with human leukocyte interferon activity, Nature, 1980, pp. 316-320, vol. 284.
Nedialkova, et al., Biochemical Characterization of Arterivirus Nonstructural Protein 11 Reveals the Nidovirus-Wide Conservation of a Replicative Endoribonuclease, J. Virol., 2009, pp. 5671-5682, vol. 83, Issue 11.
Nedialkova et al., Arterivirus Nsp1 Modulates the Accumulation of Minus-Strand Templates to Control the Relative Abundance of Viral mRNAs, PLoS Pathogens, 2010, e1000772, pp. 1-15, vol. 6, Issue 2.
Needleman, S. et al., A general method applicable to the search for similarities in the amino acid sequence of two proteins J. Mol. Biol. 48:443-53 (1970).
Nolz, J et al. Strategies and Implications for Prime-Boost Vaccination to Generate Memory CD8 T Cells, Advances in Experimental Medicine and Biology, pp. 69-83, (2011).
Pasternak, Genetic Manipulation of Arterivirus Alternative mRNA Leader-Body Junction Sites Reveals Tight Regulation of Structural Protein Expression, J. Virol., Dec. 2000, pp. 11642-11653, vol. 74, Issue 24.
Pasternak, Sequence requirements for RNA strand transfer during nidovirus discontinuous subgenomic RNA synthesis, EMBO J., 2001, pp. 7220-7228, vol. 20, Issue 24.
Pasternak, The stability of the duplex between sense and antisense transcription-regulating sequences is a crucial factor in arterivirus subgenomic mRNA synthesis, J. Virol., 2003, pp. 1175-1183, vol. 77, Issue 2.
Pasternak, Regulation of Relative Abundance of Arterivirus Subgenomic mRNAs, J. Virol., Aug. 2004, pp. 8102-8113, vol. 78, Issue 15.
Pearson, W. et al., Improved tools for biological sequence comparison, Proc. Natl. Acad. Sci. US, vol. 85, pp. 2444-2448 (1988).
Pedersen et al., Open Reading Frame 1a-Encoded Subunits of the Arterivirus Replicase induce Endoplasmic Reticulum-Derived Double-Membrane Vesicles which carry the Viral Replication Complex, J. Virol., 1999, pp. 2016-2026, vol. 73, Issue 3.
Perri et al., Replicon Vectors Derived from Sindbis Virus and Semliki Forest Virus that Establish Persistent Replication in Host Cells, J. Virol., 2000, pp. 9802-9807, vol. 74, Issue 20.
Pijlman, G. et al., Kunjin virus replicons: an RNA-based, noncytopathic viral vector system for protein production, vaccine and gene therapy applications, Expert Opin. Biol. Ther, vol. 6, No. 2, pp. 135-145 (2006).

(56) References Cited

OTHER PUBLICATIONS

Posthuma et al., Site-Directed Mutagenesis of the Nidovirus Replicative Endoribonuclease NendoU Exerts Pleiotropic Effects on the Arterivirus Life Cycle, J. Virol., 2006, pp. 1653-1661, vol. 80, Issue 4.
Posthuma et al., Formation of the Arterivirus Replication/Transcription Complex: a Key Role for Nonstructural Protein 3 in the Remodeling of Intracellular Membranes, J. Virol., 2008, pp. 4480-4491, vol. 82, Issue 9.
Pushko et al., Individual and Bivalent Vaccines Based on Alphavirus Replicons Protect Guinea Pigs against Infection with Lassa and Ebola Viruses, J. Virol., 2001, pp. 11677-11685, vol. 75, Issue 23.
Pushko et al., Replicon-Helper Systems from Attenuated Venezuelan Equine Encephalitis Virus: Expression of Heterologous Genes In Vitro and Immunization against Heterologous Pathogens In Vivo, Virology, Dec. 22, 1997, pp. 389-401, vol. 239, Issue 2.
Radford et al., Cell-Type Specificity of Interferon-γ-Mediated HLA Class I Gene Transcription in Human Hematopoietic Tumor Cells. American Society of Hepatology, 1991, pp. 2008-2015.
Rice, C. et al., Production of Infectious RNA Transcripts from Sindbis Virus cDNA Clones: Mapping of Lethal Mutations, Rescue of a Temperature-Sensitive Marker, and In Vitro Mutagenesis to Generate Defined Mutants, Journal of Virology, vol. 61, No. 12, pp. 3809-3819 (1987).
Rogne et al., The isolation and characterisation of a cDNA clone for human lecithin:cholesterol acyl transferase and its use to analyze the genes in patients with LCAT deficiency and fish eye disease, Biochem, Biophys. Res. Commun., 1987, pp. 161-169, vol. 148, Issue 1.
Sanchez and Holmgren, Recombinant system for overexpression of cholera toxin B subunit in Vibrio cholerae as a basis for vaccine development, Proc. Natl. Acad. Sci. USA, Jan. 1989, pp. 481-485, vol. 86, Issue 2.
Seif et al., Stable Antiviral Expression in BALB/c 3T3 Cells Carrying a Beta Interferon Sequence behind a Major Histocompatibility Complex Promoter Fragment, J. Virol., Oct. 1991, pp. 664-671, vol. 65, Issue 2.
Seybert et al., Biochemical Characterization of the Equine Arteritis Virus Helicase Suggests a Close Functional Relationship Between Arterivirus and Coronavirus Helicases, J. Virol., 2000, pp. 9586-9593, vol. 74, Issue 20.
Shylini, R Structure-Function Studies of the Venezuelanequine Encephalitis Virus 5'utr Promoter Element and Its Role in Attenuation of the Virus, Dissertation for Doctor of Philosophy, The University of Texas Medical Branch (2009) 147 pages.
Sjoberg,E et al., A Significantly Improved Semliki Forest Virus Expression System Based on Translation Enhancer Segments from the Viral Capsid Gene, Biotechnology, Vo,. 12, pp. 1127-1131, (1994).
Smith et al., Comparison of Biosequences, Adv. Appl. Math., 2:482-89 (1981).
Snijder, E.J., The Arterivirus Replicase, The Road from RNA to Protein(s), and Back Again, 1998, pp. 97-108. In Coronaviruses and Arteriviruses, Enjuanes et al. (ed.), Plenum Press, NY.
Snijder, E.J., Arterivirus RNA Synthesis Dissected, 2001, pp. 241-253. In the Nidoviruses (Coronaviruses and Arteriviruses), Ehud Lavi et al. (ed.), Kluwer Academic/Plenum Publishers.
Snijder et al., Proteolytic Processing of the Arterivirus Replicase, 1995, pp. 443-451. In Corona-and Related Viruses, P.J. Talbot and G.A. Levy (ed.), Plenum Press, NY.
Snijder et al., The Arterivirus Nsp2 Protease, J. Biol. Chem., 1995, pp. 16671-16676, vol. 270, Issue 28.
Snijder et al., Heterodimerization of the Two Major Envelope Proteins is Essential for Arterivirus Infectivity, J. Virol., 2003, pp. 97-104, vol. 77, Issue 1.
Snijder et al., 2005. The order Nidovirales, pp. 390-404, In Topley and Wilson's microbiology and microbial infections, B. W. Mahy and V. ter Meulen (ed.), Hodder Arnold, London, United Kingdom.
Snijder EJ et al., "Identification of a Novel Structural Protein of Arteriviruses," J. Virol, Aug. 1999, pp. 6335-6345, vol. 37, Issue 8.

Stanton et al., Nucleotide sequence comparison of normal and translocated murine c-myc genes, Nature, Aug. 1984, pp. 423-425, vol. 310.
Strauss etal., The AlpahViruses: Gene Expression, Replication and Evolution, Microbiological Reviews, pp. 491-562, Sep. 1994.
Stirpe et al., Gelonin, a New Inhibitor of Protein Synthesis, Nontoxic to Intact Cells, J. Biol. Chem., Jul. 25, 1980, pp. 6947-6953, vol. 255.
Te Velthuis, et al., Zn2+ Inhibits Coronavirus and Arterivirus RNA Polymerase Activity In Vitro and Zinc Ionophores Block the Replication of these Viruses in Cell Culture, PLoS Pathogens, 2010, e1001176, pp. 1-10, vol. 6, Issue 11.
Tepper et al., Murine interleukin-4 displays potent anti-tumor activity in vivo, Cell, May 5, 1989, pp. 503-512, vol. 57.
Thaa et al., Myristoylation of the Arterivirus E Protein: The Fatty Acid Modification is not Essential for Membrane Association but Contributes Significantly to Virus Infectivity, J. Genl. Virol., 2009, pp. 2704-2712, vol. 90.
Tijerina et al., DMS Footprinting of Structured RNAs and RNA-Protein Complexes, Nat. Protoc., 2007, pp. 2608-2623, vol. 2, Issue 10.
Tijms et al., A zinc finger-containing papain-like protease couples subgenomic mRNA synthesis to genome translation in a positive-stranded RNA virus, Proc. Natl. Acad. Sci. USA, 2001, pp. 1889-1894, vol. 98, Issue 4.
Tijms et al., Arterivirus Subgenomic mRNA Synthesis and Virion Biogenesis Depend on the Multifunctional nsp1 Autoprotease, J. Virol., Oct. 2007, pp. 10496-10505, vol. 81, Issue 19.
Toribio et al., Inhibition of host translation by virus infection in vivo, PNAS, vol. 107, No. 21, pp. 9837-9842 (2010).
Toribio et al., An RNA Trapping Mechanism in Alphavirus MRNA Promotes Translation and Initiation Nucleic Acids Res. 19, 44(9): pp. 4368-4380 (2016).
Tweten et al., Diphtheria toxin. Effect of substituting aspartic acid for glutamic acid 148 on ADP-ribosyltransferase activity., J. Biol. Chem., Jun. 3, 1985, pp. 10392-10394, vol. 260.
Twu et al., Hepatitis B virus X gene can transactivate heterologous viral sequences, Proc Natl. Acad. Sci. USA, Mar. 1989, pp. 2046-2050, vol. 86.
Van Aken et al., Expression, Purification, and In Vitro Activity of an Arterivirus Main Proteinase, Virus Res., 2006, pp. 97-106, vol. 120.
Van Aken et al., Mutagenesis Analysis of the nsp4 Main Proteinase Reveals Determinants of Arterivirus Replicase Polyprotein Autoprocessing, J. Virol., 2006, pp. 3428-3437, vol. 80, Issue 7.
Van Den Born et al., Discontinuous Subgenomic RNA Synthesis in Arteriviruses is Guided by an RNA Hairpin Structure Located in the Genomic Leader Region, J. Virol., 2005, pp. 6312-6324, vol. 79, Issue 10.
Van Den Born, Value of routine funduscopy in patients with hypertension: systematic review, BMJ, Jul. 9, 2005, pp. 1-5, vol. 331.
Van Den Born, et al., "An infectious recombinant equine arteritis virus expressing green fluorescent protein from its replicase gene," J. Genl. Virol., Apr. 2007, pp. 1196-1205, vol. 88.
Van Der Meer et al., ORF1a-Encoded Replicase Subunits are Involved in the Membrane Association of the Arterivirus Replication Complex, J. Virol., 1998, pp. 6689-6698, vol. 72, Issue 8.
Van Dinten, An infectious arterivirus cDNA clone: Identification of a replicase point mutation that abolishes discontinuous mRNA transcription, Proc. Natl. Acad. Sci. USA, Feb. 1997, pp. 991-996, vol. 94, Issue 3.
Van Dinten et al., Proteolytic Processing of the Open Reading Framer 1b-Encoded Part of Arterivirus Replicase is Mediated by nsp4 Serine Protease and is Essential for Virus Replication, J. Virol., 1999, pp. 2027-2037, vol. 73, Issue 3.
Van Dinten et al., The Predicted Metal-Binding Region of the Arterivirus Helicase Protein is Involved in Subgenomic mRNA Synthesis, Genome Replication, and Virion Biogenesis, J. Virol., 2000, pp. 5213-5223, vol. 74, Issue 11.
Van Hemert et al., The In Vitro RNA Synthesizing Activity of the Isolated Arterivirus Replication/Transcription Complex is Dependent on a Host Factor, J. Biol. Chem., 2008, pp. 16525-16536, vol. 283, Issue 24.

(56) References Cited

OTHER PUBLICATIONS

Van Kasteren et al., Arterivirus and Nairovirus Ovarian Tumor Domain-Containing Deubiquitinases Target Activated RIG-I to Control Innate Immune Signaling, J. Virol., 2011, pp. 773-785, vol. 82, Issue 2.
Van Kasteren et al., Deubiquitinase Function of Arterivirus Papain-Like Protease 2 Suppresses the Innate Immune Response in Infected Host Cells, PNAS, 2013, pp. E838-E847.
Van Marle, et al., Characterization of an Equine Arteritis Virus Replicase Mutant Defective in Subgenomic mRNA Synthesis, J. Virol., 1999, pp. 5274-5281, vol. 73, Issue 7.
Van Marle et al., Arterivirus discontinuous mRNA transcription is guided by base pairing between sense and antisense transcription-regulating sequences, Pro. Natl. Acad. Sci. USA, Aug. 6, 1999, pp. 12056-12061, vol. 96, Issue 21.
Ventoso, I., Adaptive Changes in Alphavirus mRNA Translation Allowed Colonization of Vertebrate Hosts, Journal of Virology, vol. 86, No. 17, pp. 9484-9494 (2012).
Ventoso, I. et al. Translational resistance of late alphavirus mRNA to eIF2 phosphorylation: a strategy to overcome the antiviral effect of protein kinase PKR, Genes and Development, vol. 20, pp. 87-100 (2006).
Vrudhula et al., Prodrugs of doxorubicin and melphalan and their activation by a monoclonal antibody-penicillin-G amidase conjugate, J. Med. Chem., 1993, pp. 919-923, vol. 36, Issue 7.
Ward, S. et al., Generation of CTL responses using Kunjin replicon RNA, Immunology and Cell Biology, vol. 81, pp. 73-78 (2003).
Warner et al. Induction of the HIV-Specific and Antibody Responses in Mice Using Retroviral Vector-Transduced Cells, AIDS Res. and Human Retroviruses, vol. 7, No. 8, pp. 645-655 (1991).
Wassenaar, et al., Alternative Proteolytic Processing of the Arterivirus Replicase ORF1a Polyprotein: Evidence that NSP2 Acts as a Cofactor for the NSP4 Serine Protease, J. Virol., 1997, pp. 9313-9322, vol. 71, Issue 12.
Watanabe, et al., Exogenous expression of mouse interferon gamma cDNA in mouse neuroblastoma C1300 cells results in reduced tumorigenicity by augmented anti-tumor immunity, Proc. Natl. Acad. Sci. USA, Dec. 1989, pp. 9456-9460, vol. 86.
Weber et al., Immunotherapy of a murine tumor with interleukin 2. J. Exp. Med., 1987, pp. 1716-1733, vol. 166.
White, L. et al., Role of Alpha/Beta Interferon in Venezuelan Equine Encephalitis Virus Pathogenesis: Effect of an Attenuating Mutation in the 59 Untranslated Region, Journal of Virology, vol. 75, No. 8, pp. 3706-3718 (2001).
Wilson et al., Prospects for gene therapy of familial hypercholesterolemia, Mol. Biol. Med., Jun. 1, 1990, pp. 223-232, vol. 7, Issue 3.
Wood et al., Preproabrin: genomic cloning, characterisation and the expression of the A-chain in *Escherichia coli*, Eur. J. Biochem., 1991, pp. 723-732, vol. 198.
Yamamoto et al., The human LDL receptor: a cysteine-rich protein with multiple Alu sequences in its mRNA, Cell, Nov. 1984, pp. 27-38, vol. 39, Issue 1.
Zhou, X. et al. Self-replicating Semliki Forest virus RNA as recombinant vaccine, Vaccine, vol. 12, No. 16, pp. 1510-1514 (1994).
GenBank/NCBI accession No. J02363, dated Oct. 25, 2000; accessed Jul. 16, 2018, 7 pages.
GenBank accession # JX473847, dated Dec. 22, 2012; accessed Apr. 17, 2019, 6 pages.
GenBank/NCBI accession No. L01443.1., dated Nov. 17, 2014; accessed Oct. 3, 2016, 7 pages.
GenBank/NCBI accession No. L04653, dated Jun. 1, 2001; accessed Jul. 16, 2018, 6 pages.
GenBank/NCBI accession No. NC_001449, dated Feb. 10, 2015; accessed Jul. 16, 2018, 7 pages.
GenBank/NCBI accession No. NC_003215, dated Feb. 10, 2015; accessed Jul. 16, 2018, 6 pages.
GenBank/NCBI accession No. U38304; dated Feb. 10, 2015; accessed Jul. 16, 2018, 5 pages.
GenBank/NCBI accession No. U38305, dated Jan. 30, 2016, accessed Jul. 16, 2018, 5 pages.
GenBank/NCBI accession No. X04129, dated Mar. 13, 2001; accessed Jul. 16, 2018, 5 pages.
International Search Report and Written Opinion, dated Dec. 1, 2017, in International Application No. PCT/US2017/054928, 18 pages.
International Search Report and Written Opinion, dated Jul. 10, 2017, in International Patent Application No. PCT/US2017/027249, filed Apr. 12, 2017, 16 pages.
International Search Report and Written Opinion, dated Jul. 3, 2018, in International Application No. PCT/US2017/064561, 22 pages.
Frolov et al, (Journal of Virology, 1999, p. 3854-3865).
Bolz et al.: "Use of Recombinant Virus Replicon Particles for Vaccination against *Mycobacterium ulcerans* Disease"; PLoS Negl Trop Dis,, Aug. 14, 2015, vol. 9(8):e0004011., PDF File: p. 1-18.
International Search Report issued on Apr. 23, 2019, regarding PCT/US2019/014210, 13 pages.
Lundstrom, Kenneth L: "Replicon RNA Viral Vectors as Vaccines"; Vaccines, 2016, vol. 4(4). pii: E39. PDF File: p. 1-23.
Uematsu et al.: "Lack of Interference with Immunogenicity of a Chimeric Alphavirus Replicon Particle-Based Influenza Vaccine by Preexisting Antivector Immunity"; Clin Vaccine Immunol., Jul. 2012, vol. 19(7), p. 991-998.
Xu et al.: "Type-specific and cross-reactive antibodies induced by human papillomavirus 31 L1/L2 virus-like particle";, J Med Microbiol. 2007, vol. 56(Pt 7), p. 907-13.
Tian et al. Arterivirus minor envelope proteins are a major determinant of viral tropism in cell culture. J Virol. Apr. 2012;86(7):3701-12. (Year: 2012).
Baker et al., Protein Structure Predication and Structural Genomics, Science (2001) vol. 294, No. 5540, pp. 93-96 (Year: 2001).
Huang et al. Development of a vaccine vector based on a subgenomic replicon of porcine reproductive and respiratory syndrome virus. J Virol Methods. Sep. 2009;160(1-2):22-8. (Year: 2009).
Araujo et al, "Expression of Hepatitis B virus surface antigen (HBsAg) from genotypes A, D and F and influence of amino acid variations related or not to genotypes on HBsAg detection," Brazilian Journal of Infectious Diseases, Jan. 1, 2009, vol. 13, Nr: 4.
Boukhebza, Houda et al. Comparative analysis of immunization schedules using a novel adenovirus-based immunotherapeutic targeting hepatitis B in naïve and tolerant mouse models, Vaccine, vol. 32, issue 26, pp. 3256-3263 (May 30, 2014).
GenBank: KT121715.1: Accession KT121715, Version KT121715.1. 2015, Sindbis virus isolate Treatmant1_population9, complete genome, 5 pages (Year: 2015).
GenBank: L01443.1 Accession No. L01443, 2004, Venezuelan equine encephalitis virus strain TC-83, complete genome, 5 pages (Year: 2004).
Giese M, Bahr U, Jakob NJ, Kehm R, Handermann M, Müller H, Vahlenkamp TH, Spiess C, Schneider TH, Schusse G, Darai G. U Stable and long-lasting immune response in horses after DNA vaccination against equine arteritis virus. Virus Genes. Oct. 2002;25(2):159-67. (Year: 2002).
Hernandez et al .Structural Differences Observed in Arboviruses of the Alphavirus and Flavivirus Genera 2014. Advances in Virology. vol. 2014, Article ID 259382, 25 pages (Year: 2014).
Jeeva S, Lee JA, Park SY, Song CS, Choi IS, Lee JB. Development of porcine respiratory and reproductive syndrome virus replicon vector for foot-and-mouth disease vaccine. Clin Exp Vaccine Res. Jan. 2014;3(1):100-9. doi: 10.7774/cevr.2014.3.1.100. Epub Dec. 18, 2013. PMID: 24427767; PMCID: PMC3890444. (Year: 2014).
Johansson et al, 2012, PLOS ONE, Intradermal Electroporation of Naked Replicon RNA Elicits Strong Immune Responses, 7(1):e29732.
Obeng-Adjei et al., "Synthetic DNA immunogen encoding hepatitis B core antigen drives immune response in liver," Cancer Gene Therapy, Nov. 5, 2012 Appleton & Lange, New York, vol. 19, Nr: 11, pp. 779-787.
Petrakova et al, Noncytopathic Replication of Venezuelan Equine Encephalitis Virus and Eastern Equine Encephalitis Virus Replicons in Mammalian Cells, Journal of Virology, Jun. 2005, p. 7597-7608.
Ramirez et at., "Biology of Attenuated Modified Vaccinia Virus Ankara Recombinant Vector in Mice: Virus Fate and Activation of

(56) References Cited

OTHER PUBLICATIONS

B- and T-Cell Immune Responses in Comparison with the Western Reserve Strain and advantages as a Vaccine", Journal of Virology, Vo. 74, No. 2, pp. 923-933, 2000.

Reyes-Sandoval Arturo et al., "Prime-Boost Immunization with Adenoviral and Modified Vaccinia Virus Ankara Vectors Enhances the Durability and Polyfunctionality of Protective Malaria CD8(+) T-Cell Responses", Infection and Immunity, (Jan. 2010), vol. 78, No. 1, pp. 145-153, XP002778539.

Yin et. al. Similarities and Differences in Antagonism of Neuron Alpha/Beta and Sindbis Alphaviruses 2009. Journal of Virology. 83 ( 19) p. 10036-10047 (Year: 2009).

Mir et. al. A Multicistronic DNA Vaccine Induces Significant Protection against Tuberculosis in Mice and Offers Flexibility in the Expressed Antigen Repertoire. 2009. Clinical and Vaccine Immunology. vol. 16, No. 10. p. 1467-1475 (Year: 2009).

Kim, et al., "New World and Old World Alphaviruses Have Evolved to Exploit Different Components of Stress Granules, FXR and G3BP Proteins, for Assembly of Viral Replication Complexes", PLOS Pathogens, vol. 12, No. 8, p. 1-31, (Aug. 2016).

Foy, et al., "Hypervariable domains of nsP3 proteins of New World and Old World alphaviruses mediate formation of distinct, virus-specific protein complexes", J. Virol., vol. 87, No. 4, p. 1997-2010, (Dec. 2012).

Gotte, et al., "The Enigmatic Alphavirus Non-Structural Protein 3 (nsP3) Revealing Its Secrets at Last", Viruses, vol. 10, No. 3, p. 105, 1/26 to 26/26, (Feb. 2018).

Meshram, et al., "Multiple Host Factors Interact with the Hypervariable Domain of Chikungunya Virus nsP3 and Determine Viral Replication in Cell-Specific Mode", J. Virol., vol. 92, No. 16, p. 1-24, (Aug. 2018).

International Search Report and Written Opinion issued Dec. 13, 2019 in International Appl. No. PCT/US2019/055125.

* cited by examiner

FIG. 2A nsP1 | nsP2 | nsP3 | nsP4 | rFF

Macro | AUD | HVD  VEEV WT
Macro | AUD | HVD  VEEV/SINV HVD (335-538)
Macro | AUD | HVD  VEEV/CHICK HVD (335-517)

FIG. 2B frequency of dsRNA+ cells vs Mock, WT, VEEV/CHIKV, VEEV/SINV (SGIα-rFF)

FIG. 2C

Luciferase activity vs Mock, WT, VEEV/CHIKV, VEEV/SINV (SGIα-rFF)

ALPHAVIRUS-BASED REPLICONS FOR ADMINISTRATION OF BIOTHERAPEUTICS

Reference to Copyright Material

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

CROSS-REFERENCE TO RELATED APPLICATIONS

This application claims priority to U.S. Provisional Patent Application No. 62/742,868, filed Oct. 8, 2018, the disclosure of which is hereby incorporated by reference herein in its entirety.

REFERENCE TO SEQUENCE LISTING SUBMITTED ELECTRONICALLY

This application contains a sequence listing, which is submitted electronically via EFS-Web as an ASCII formatted sequence listing with a file name "689405.107U1_SL", a creation date of Oct. 7, 2019, and having a size of 147 KB. The sequence listing submitted via EFS-Web is part of the specification and is herein incorporated by reference in its entirety.

BACKGROUND OF THE INVENTION

Alphavirus based self-amplifying RNAs (replicons) have been used for decades as a universal platform for vaccines. Two characteristics that make replicons suitable for such a platform are 1) high and prolonged protein expression and 2) the self-adjuvanting nature of the platform, which helps drive robust cellular, humoral and mucosal immunity. While these characteristics cause the replicon to excel as vaccine platforms, they have the potential to hinder its performance in other areas, particularly as platforms for the in vivo expression of biotherapeutics.

The use of biotherapeutics in medicine is on the rise. However, these recombinantly produced proteins are frequently recognized as foreign and elicit an immune response and the induction of anti-drug antibodies (ADAs), thus reducing the protein's therapeutic effectiveness. While the factors contributing to the development of an anti-drug antibody (ADA) response are varied the inflammatory milieu in which a biologic or biotherapeutic is delivered can promote and/or enhance an ADA response. Therefore, delivery of a biologic from a replicon that is naturally self-adjuvanting and inflammatory runs the risk of promoting an ADA response and reducing clinical efficacy of the encoded biotherapeutic. The ability to down-modulate the immune response against a heterologous protein expressed from a replicon would reduce the risk of generating ADAs and enhance the utility of replicons for the expression of biotherapeutics in vivo.

It would therefore be useful to have compositions and methods that would enable the administration of biotherapeutic molecules to humans or animals with a reduced or eliminated risk of provoking an undesirable immune response.

SUMMARY OF THE INVENTION

The invention provides RNA replicons useful for administering a heterologous molecule to a human or animal and reducing or eliminating an immune response from the human or animal to the heterologous molecule. The RNA replicons have RNA sequences (e.g. a gene of interest (GOI)) encoding a heterologous molecule (e.g. a protein or peptide), and RNA sequences encode New World alphavirus nonstructural proteins nsP1, nsP2, and nsP4; and an alphavirus nsP3 protein macro domain, central domain, and hypervariable domain (HVD). The encoded hypervariable domain can have an amino acid sequence derived from an Old World alphavirus nsP3 hypervariable domain, or can have an amino acid sequence derived from a portion of a New World alphavirus nsP3 hypervariable domain, and another portion derived from an Old World alphavirus nsP3 hypervariable domain, i.e. a chimeric nsP3 hypervariable domain. It was found that when the replicon based on a New World alphavirus is modified as described herein, an immune response provoked by the encoded heterologous protein or peptide is diminished or eliminated.

The RNA replicons are useful for the administration of biotherapeutic molecules such as proteins and peptides, where the replicons of the invention are administered to a human or animal with the biotherapeutic being encoded by the replicon, and the encoded biotherapeutic (e.g. a heterologous protein or peptide) is expressed in the human or animal.

In a first aspect the invention provides an RNA replicon having an RNA sequence encoding a heterologous protein or peptide; 5' and 3' alphavirus untranslated regions; RNA sequences encoding amino acid sequences derived from New World alphavirus nonstructural proteins nsP1, nsP2, and nsP4; and an RNA sequence encoding an amino acid sequence derived from an alphavirus nsP3 macro domain; an RNA sequence encoding an amino acid sequence derived from an alphavirus nsP3 central domain; and an RNA sequence encoding a hypervariable domain having an amino acid sequence derived from an Old World alphavirus nsP3 hypervariable domain, or an amino acid sequence comprising a portion derived from a New World alphavirus nsP3 hypervariable domain, and a portion derived from an Old World alphavirus nsP3 hypervariable domain.

In some embodiments, the alphavirus nsP3 macro domain and the alphavirus nsP3 central domain are derived from a New World alphavirus, but in other embodiments the alphavirus nsP3 macro domain and the alphavirus nsP3 central domain are derived from an Old World alphavirus. In various embodiments the Old World alphavirus is selected from the group consisting of: CHIKV, SINV, and SFV. The New World alphavirus can be Venezuelan Equine Encephalitis Virus (VEEV) or western equine encephalitis virus (WEEV), or eastern equine encephalitis virus (EEEV). In various embodiments the Old World alphavirus can be any of Sindbis virus (SINV), Chickungunya virus (CHIKV), Semliki Forest Virus (SFV), Ross River Virus (RRV), Sagiyama virus (SAGV), Getah virus (GETV), Middleburg virus (MIDV), Bebaru virus (BEBV), O'nyong nyong virus (ONNV), Ndumu (NDUV), and Barmah Forest virus (BFV).

In some embodiments, the portion derived from the Old World alphavirus nsP3 hypervariable domain comprises a motif selected from the group consisting of: FGDF (SEQ ID NO: 18) and FGSF (SEQ ID NO: 19). The portion derived from the Old World alphavirus nsP3 hypervariable domain can have a repeat selected from the group consisting of: an FGDF/FGDF (SEQ ID NO: 20) repeat, an FGSF/FGSF (SEQ ID NO: 21) repeat, an FGDF/FGSF (SEQ ID NO: 22) repeat, and an FGSF/FGDF (SEQ ID NO: 23) repeat; and the repeat sequences can be separated by at least 10 and not more than 25 amino acids. In some embodiments the repeat sequences are separated by an amino acid sequence derived from the group consisting of: NEGEIESLSSELLT (SEQ ID NO: 6), SDGEIDELSRRVTTESEPVL (SEQ ID NO: 7), and DEHEVDALASGIT (SEQ ID NO: 8).

In any of the embodiments of the RNA replicons the portion derived from the Old World alphavirus hypervariable domain can have any of amino acids 479-482 or 497-500 or 479-500 or 335-517 of CHIKV nsP3 HVD; or any of amino acids 451-454 or 468-471 or 451-471 of SFV nsP3 HVD; or amino acids 490-493 or 513-516 or 490-516 or 335-538 of SINV nsP3 HVD. In any of these embodiments (or in any embodiment described herein) the New World alphavirus can be VEEV and the portion derived from the New World alphavirus hypervariable domain does not comprise amino acids 478-518 of the VEEV nsP3 hypervariable domain; or does not comprise amino acids 478-545 of the VEEV nsP3 hypervariable domain; or does not comprise amino acids 335-518 of the VEEV nsP3 hypervariable domain. In other embodiments the New World alphavirus can be EEEV and the portion derived from the New World alphavirus hypervariable domain does not comprise amino acids 531-547 of the EEEV hypervariable domain. Or the New World alphavirus can be WEEV, and the portion derived from the New World alphavirus hypervariable domain does not comprise amino acids 504-520 of the WEEV hypervariable domain.

In any of the embodiments the RNA replicon can have a sub-genomic promoter that is operably linked to and regulates translation of the RNA sequence encoding the heterologous protein. The RNA replicons can also have a 5' cap and a 3' poly-A tail. The RNA replicon can have a positive sense, single-stranded RNA. In various embodiments the RNA replicons can have 10-12 kb of RNA and/or can have a diameter of 30-50 nm.

In various embodiments the heterologous protein is a biotherapeutic protein or peptide, which can be, for example, an antibody or an engineered chimeric antibody or an antibody fragment, an antigenic polypeptide or any other therapeutic or immunogenic polypeptide or peptide.

In some specific embodiments of the replicons the New World alphavirus is VEEV, and the portion derived from a New World alphavirus nsP3 hypervariable domain does not comprise amino acids 335-518 of the VEEV nsP3 hypervariable domain, and the portion derived from an Old World alphavirus nsP3 hypervariable domain comprises amino acids 490-516 of SINV nsP3 HVD; or the Old World alphavirus is SINV and the portion derived from an Old World alphavirus nsP3 hypervariable domain comprises amino acids 335-538 of SINV nsP3 HVD.

In any of the embodiments the RNA sequence encoding the heterologous protein or peptide can be operably linked to the RNA sequence encoding the nsP1, nsP2, and nsP4.

In another aspect the invention provides methods of administering a heterologous protein or peptide to a mammal. The methods involve administering to the mammal an RNA replicon described herein that encodes the heterologous protein or peptide, and wherein the heterologous protein or peptide is expressed within the mammal. The RNA replicon can be any described herein.

In another aspect the invention provides an RNA replicon having an RNA sequence encoding a heterologous protein or peptide; RNA sequences encoding amino acid sequences derived from New World alphavirus nonstructural proteins nsP1, nsP2, and nsP4; and an RNA sequence encoding an amino acid sequence derived from an Old World alphavirus nsP3 protein, and wherein the first 1-6 amino acids on the N-terminal and/or C-terminal side of the nsP3 protein are derived from a New World alphavirus sequence. Thus, the 1-6 amino acids can be present on the junction between nsP2 and nsP3; or the 1-6 amino acids can be present on the junction between nsP3 and nsP4. In various embodiments the Old World alphavirus can be any described herein. When the New World alphavirus is VEEV the nsP2/nsP3 junction sequence can be LHEAGC/APSY (SEQ ID NO: 12); when the junction is the nsP3/nsP4 junction the sequence can be RFDAGA/YIFS (SEQ ID NO: 13). In any of the embodiments the penultimate glycine (also referred to by its single-letter code "G") can be preserved and the remaining nsP3 amino acids varied as described herein. The junction sequences can optionally be preceded by a stop codon (TGA), which can be a readthrough stop codon. In other embodiments where the New World alphavirus is EEEV, the nsP2/nsP3 junction sequence can be QHEAGR/APAY (SEQ ID NO: 14), and with the penultimate G preserved. When the New World alphavirus is EEEV the sequence at the nsP3/nsP4 junction can be RYEAGA/YIFS (SEQ ID NO: 15), and the penultimate glycine can be optionally preserved while the remaining nsP3 amino acids varied as described herein. These sequences can also be preceded by a read-through stop codon (TGA). In other embodiments the New World alphavirus is WEEV, and the nsP2/nsP3 junction sequence can be RYEAGR/APAY (SEQ ID NO: 16), and the penultimate G preserved while the remaining amino acids in the nsP2/nsP3 junction are varied as described herein. For the nsP3/nsP4 junction of WEEV, the sequence can be RYEAGA/YIFS (SEQ ID NO: 17), with the penultimate glycine preserved and the remaining nsP3 amino acids varied as described herein; these sequences can also be preceded by a read-through stop codon (TGA). In various embodiments the sequences of SEQ ID NOs: 12-17 can also contain one or two or three substitutions on the N-terminal and/or C-terminal sides.

The summary of the invention described above is not limiting and other features and advantages of the invention will be apparent from the following detailed description of the invention, and from the claims. Section headings or sub-headings are provided solely for the convenience of the reader, and do not denote a departure from discussion or necessarily an entirely new subject matter area. Any subject matter can be discussed or disclosed under any section heading or sub-heading.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

FIG. 2A-FIG. 2C: FIG. 2A is a graphical illustration of a VEEV-based alphavirus replicon encoding red firefly luciferase (rFF). Three embodiments are depicted: one having a wild-type VEEV HVD of nsP3 (WT), one a VEEV/SINV hybrid (VEEV/SINV) having a portion of the HVD of SINV (by substituting amino acid residues 335-538 of VEEV HVD with amino acids 335-538 of SINV HVD; and another hybrid (VEEV/CHIKV) having a portion of CHIKV HVD (by substituting amino acid residues 335-518 of VEEV HVD with amino acids 335-517 of CHIKV HVD). FIGS. 2B and 2C are graphical illustrations showing that replicons containing mutant nsP3 proteins replicated to the same levels (FIG. 2B) and express the same levels of rFF (FIG. 2C) as replicons containing wild type nsP3.

FIG. 3A is a graph showing the results of monitoring in vivo luciferase activity and reported as total flux. 10 ug of each of the three VEEV-based alphavirus replicon RNAs depicted in FIG. 2A in saline was delivered intra-muscularly into the quadricep muscle of BALB/c mice, wherein α.SGI.rFF encodes VEEV WT, α.SGI.SINV.rFF encodes VEEV/SINV, and α.SGI.CHIKV.rFF encodes VEEV/CHIKV. FIG. 3B shows the results of monitoring the same but with 1 ug of replicon RNA. Replicons expressing mutant forms of nsP3 exhibited similar levels of luciferase activity as replicons with wild type nsP3.

FIG. 4 is a plot and bar graph showing the results of in vivo studies of VEEV-based replicons expressing HA from H5N1 influenza virus. The data show that replicons encoding a VEEV/CHIKV HVD chimera did not elicit HA specific IgG titers compared to a replicon expressing wild type HVD.

FIG. 5A provides a plot in graphical format demonstrating the frequency of HA specific short-lived effector CD8+ T cells (SLECs) in BALB/c mice immunized with the indicated VEEV-based replicons expressing H5N1 HA. FIG. 5B provides a plot in graphical format demonstrating the frequency of HA specific memory precursor effector CD8+ T cells (MPECs) in BALB/c mice immunized with the indicated VEEV-based replicons expressing H5N1 HA. WT refers to the unmodified replicon backbone derived from the TC-83 strain of VEEV; SGI refers to a replicon backbone that was modified to be interferon resistant.

FIG. 6 provides a portion of the domain structure and sequence alignment of nsP3 proteins of representative members of the New World and Old World alphaviruses. The schematic representation of the nsP3 protein shows the three predicted structural domains: the macro domain, the alpha domain, and the HVD. The sequence alignment of nsP3 proteins of different alphaviruses was performed with Clustal Omega. The domain sequences are underlined with the same colors as those used in the schematic presentation. The illustrated nsP3 protein sequences were derived from the following viruses: SFV (GenBank accession no. NP_740667.1) (protein shown is SEQ ID NO: 24), SINV (GenBank accession no. P03317.1) (protein shown is SEQ ID NO: 25), CHIKV (GenBank accession no. NP_690588.1) (protein shown is SEQ ID NO: 26), VEEV (GenBank accession no. P27282.2) (protein shown is SEQ ID NO: 27), and EEEV (GenBank accession no. Q4QXJ8.2) (protein shown is SEQ ID NO: 28). Image taken from Foy et al., Journal of Virology, Vol. 87, No. 4, pp. 1997-2010 (2013).

DETAILED DESCRIPTION OF THE INVENTION

Figure 1:
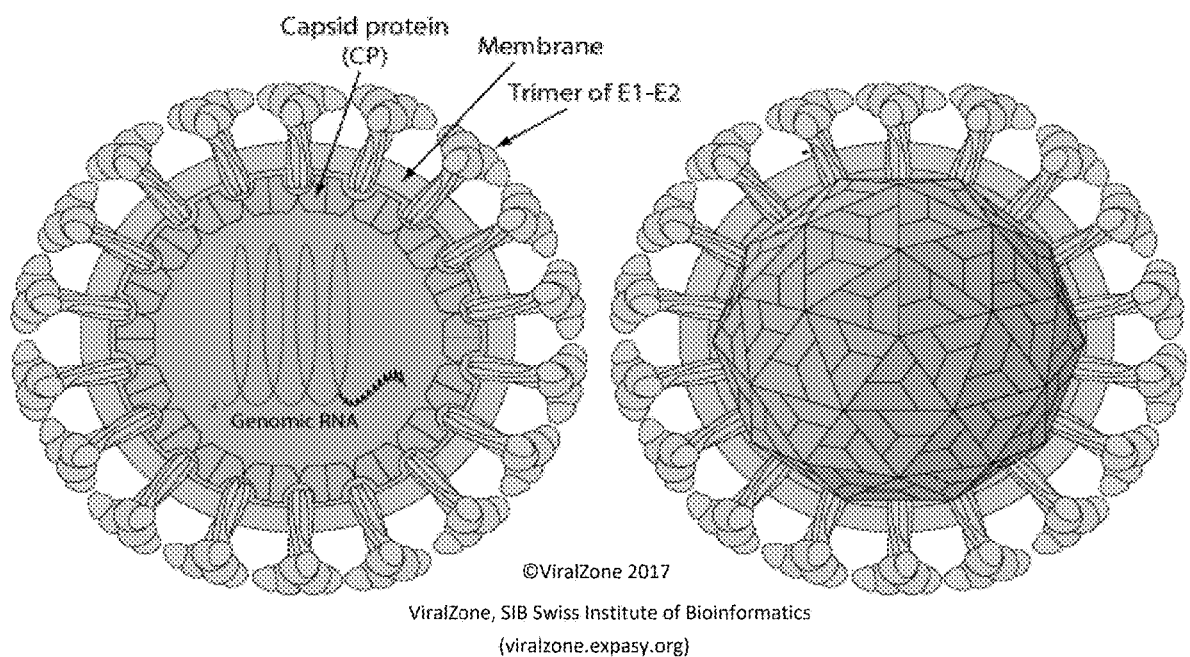
FIG. 1 provides a graphical illustration of a wild type alphavirus. The viral particle is shown as being enveloped, spherical, icosahedral, having a 65-70 nm diameter capsid with a T=4 icosahedral symmetry made of 240 monomers. The envelope contains 80 spikes, with each spike being a trimer of E1/E2 proteins.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications, and publications cited herein are incorporated by reference as if set forth fully herein. It must be noted that as used herein and in the appended claims, the singular forms "a," "an," and "the" include plural reference unless the context clearly dictates otherwise.

Unless otherwise stated, any numerical value, such as a % sequence identity or a % sequence identity range described herein, are to be understood as being modified in all instances by the term "about." Thus, a numerical value typically includes ±10% of the recited value. For example, a dosage of 10 mg includes 9 mg to 11 mg. As used herein, the use of a numerical range expressly includes all possible subranges, all individual numerical values within that range, including integers within such ranges and fractions of the values unless the context clearly indicates otherwise.

Throughout this specification and the claims which follow, unless the context requires otherwise, the word "comprise," and variations such as "comprises" and "comprising," will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having."

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising," "containing," "including," and "having," whenever used herein in the context of an aspect or embodiment of the invention can be replaced with the term "consisting of" or "consisting essentially of" to vary scopes of the disclosure.

In one general aspect, the invention relates to RNA replicons that encode a heterologous protein or peptide, and methods of administering them to a human or animal using the RNA replicons. The RNA replicons of the invention contain an RNA sequence encoding a heterologous protein or peptide, and RNA sequences encoding amino acid sequences derived from New World alphavirus nsP1, nsP2, and nsP4 proteins. The replicons also have an RNA sequence encoding an amino acid sequence derived from an alphavirus nsP3 macro domain, and an RNA sequence encoding an amino acid sequence derived from an alphavirus nsP3 central domain. The RNA replicons of the invention further have an RNA sequence encoding an amino acid sequence derived entirely from an Old World alphavirus nsP3 hypervariable domain, or an amino acid sequence having a portion derived from a New World alphavirus nsP3 hypervariable domain, and a portion derived from an Old World alphavirus nsP3 hypervariable domain. i.e. the HVD can be a hybrid or chimeric New World/Old World sequence. As used herein, a "polypeptide", "peptide" or "protein" means a molecule that comprises at least two amino acid residues linked by a peptide bond to form a polypeptide.

As used herein, with respect to an alphavirus nsP3 or an alphavirus nsP3 hypervariable domain (HVD), the amino acid residues are numbered relative to the amino acid sequence of the wild-type alphavirus nsP3. The amino acid sequence of a wild-type alphavirus nsP3 is described herein or otherwise available from the public record, such as the GenBank database. For example, with respect to a SFV nsP3, the amino acid residues are numbered relative to wild-type SFV nsP3 of SEQ ID NO:24; with respect to a SINV nsP3, the amino acid residues are numbered relative to wild-type SINV nsP3 of SEQ ID NO:25; with respect to a CHIKV nsP3, the amino acid residues are numbered relative to wild-type CHIKV nsP3 of SEQ ID NO:26; with respect to a VEEV nsP3, the amino acid residues are numbered relative to wild-type VEEV nsP3 of SEQ ID NO: 27; with respect to an EEEV nsP3, the amino acid residues are numbered relative to wild-type EEEV nsP3 of SEQ ID NO: 28; and with respect to a WEEV nsP3, the amino acid residues are numbered relative to wild-type WEEV nsP3 of SEQ ID NO: 29.

The nsP1, nsP2, nsP3, and nsP4 proteins encoded by the replicon are functional or biologically active proteins. The RNA replicons of the invention can also encode a 3' untranslated region (UTR) and a 5' UTR, which can be alphavirus 3' and 5' UTRs. The RNA replicons can also encode control elements (e.g. one or more sub-genomic promoters) and a poly-A tail. The promoter, 5' and/or 3' UTRs, and RNA sequence encoding the heterologous protein or peptide can be operably linked so that the replicon RNA self-amplifies upon introduction into an organism and the heterologous protein or peptide is expressed in the organism.

The inventors of the application discovered that, unexpectedly, in an RNA replicon derived from a New World alphavirus (NW) genome, if at least a portion of the RNA encoding the nsP3 protein is substituted with RNA encoding at least a portion of nsP3 derived from an Old World alphavirus (OW), then the immunogenicity in a mammal to a heterologous protein or peptide encoded in the replicon is significantly reduced or eliminated. Thus, in some embodiments of the replicon, the nsP3 macro domain and central domain can be derived from New World alphavirus sequences, while the HVD a) is derived from an Old World alphavirus HVD sequence, or b) has a portion derived from an Old World alphavirus HVD sequence and a portion derived from a New World alphavirus HVD sequence.

In another embodiment the macro and central domains are derived from Old World alphavirus macro and central domain sequences, and the HVD a) is derived from an Old World alphavirus HVD sequence, or b) has a portion derived from an Old World alphavirus HVD sequence and a portion derived from a New World alphavirus HVD sequence.

In another embodiment the macro domain is derived from a New World alphavirus macro domain sequence, the central domain is derived from an Old World alphavirus central domain sequence, and the HVD a) is derived from an Old World alphavirus HVD sequence, or b) has a portion derived from an Old World alphavirus HVD sequence and a portion derived from a New World alphavirus HVD sequence.

In another embodiment the macro domain is derived from an Old World alphavirus macro domain sequence, the central domain is derived from a New World alphavirus central domain sequence, and the HVD a) is derived from an Old World alphavirus HVD sequence, or b) has a portion derived from an Old World alphavirus HVD sequence and a portion derived from a New World alphavirus HVD sequence.

In some embodiments the replicon encodes an HVD that is a hybrid or chimeric New World/Old World sequence having a portion derived from a New World alphavirus HVD sequence and a portion derived from an Old World HVD sequence. In various embodiments the Old World portion can be at least 5 or at least 10 or at least 15 or at least 20 or at least 25 or at least 30 or at least 52 or at least 53 or at least 75 or at least 100 or at least 125 or at least 150 or at least 175 or at least 200 amino acids. The portions together can comprise an HVD having the same length as a wild type Old World or New World alphavirus HVD sequence, or can be up to 10 or up to 20 or up to 30 amino acids shorter; or can be up to 10 or up to 20 or up to 30 or up to 40 or up to 50 or up to 60 or up to 70 or up to 80 or up to 90 or up to 100 amino acids longer than a wild type, Old World or New World alphavirus HVD sequence.

In some embodiments the N-terminal portion of the HVD can be derived from the New World nsP3 HVD sequence and the C-terminal amino acids of the HVD can be derived from a wild type OW alphavirus HVD amino acid sequence, for example the at least 5 or at least 10 or at least 15 or at least 20 or at least 25 or at least 30 or at last 31 or at least 32 or at least 33 or at least 34 or at least 35 or 35-55 or 35-65 or at least 40 or at least 45 or at least 50 or at least 52 or at least 53 or at least 60 or at least 70 or at least 80 or at least 100 or at least 125 or at least 150 or at least 175 C-terminal amino acids of the HVD can be an amino acid sequence derived from (and optionally corresponding to) the amino acids of the OW HVD; in any of these embodiments the HVD can also be less than 200 or less than 175 or less than 150 or less than 125 or less than 100 or less than 80 amino acids in length. In further embodiments the C-terminal amino acids can be retained from the NW alphavirus C-terminal HVD sequence, such as the terminal 1-5 or 5 or 5-10 or 10-12 or 10-13 or 10-15 or 15-20 amino acids, while the remaining C-terminal amino acids can be derived from an OW alphavirus HVD as described.

In any of the embodiments described herein the New World alphavirus can be VEEV or EEEV or WEEV or any New World alphavirus described herein or known in the art, and the Old World alphavirus can be CHIKV, SINV, or SFV or any Old World virus described herein or known in the art. New World and Old World alphaviruses can be used in the invention in any combination, and all possible combinations and sub-combinations are disclosed as if set forth fully herein.

Alphavirus Replicons

Alphaviruses are classified in the Group IV Togaviridae family of viruses. These viruses carry a positive-sense single-stranded RNA genome, which typically ranges from 11 kb-12 kb. The alphavirus replicons of the invention can be 11 kb-12 kb in length, or 10-13 kb, or 7-20 kb or 7-25 kb in length, and can have a 5' cap and a 3' poly-A tail, which can be an alphavirus 5' cap and 3' poly-A tail. The 5' cap can be those known to persons of skill in the art, e.g. a 7-methylguanylate cap, or the anti-reverse cap analog 3'-O-Me-m7G(5')ppp(5')G or another analog cap structures. They are generally enveloped viruses and are spherical in shape, having a diameter of about 70 nm. They also can have an isometric nucleocapsid. The replicons can be encoded on a single piece of RNA. The alphavirus genome and the replicons have two open reading frames (ORFs), non-structural and structural. The non-structural portion of the genome encodes proteins nsP1-nsP4, which play a role in transcription and replication of viral RNA and are produced as a polyprotein and are the virus replication machinery. But the replicons can have one or two or more than two open reading frames. Any of the alphavirus replicons of the invention can lack, or not comprise, or not be comprised within or associated with, a capsid, nucleocapsid, coat protein, or nucleoprotein. The alphavirus replicons can be an RNA molecule.

The structural portion of the genome encodes the core nucleocapsid protein C, and envelope proteins P62 and E1 that associate as a heterodimer. The RNA replicons of the invention can have any one or more of the described characteristics of an alphavirus. In some embodiments the RNA replicons of the invention lack sequences encoding alphavirus structural proteins; or do not encode alphavirus (or, optionally, any other) structural proteins. In some embodiments the RNA replicons of the invention do not encode any one or more of protein C, P62, 6K, and E1, including all combinations and sub-combinations as if set forth fully herein. In some embodiments the RNA replicons of the invention do not encode any one of protein C, P62, 6K, and E1.

The geographic separation of the alphavirus family may be a factor in the evolution and adaption of these viruses to their unique environments. Circulating alphavirus sero-complexes can be further categorized as either Old World or New World alphaviruses. Old World and New World alphaviruses have sequences that can be utilized in the invention as described herein. New World alphaviruses include any New World alphavirus, for example the Eastern equine encephalitis virus (EEEV), the Venezuelan equine encephalitis virus (VEEV), Western equine encephalitis virus (WEEV), Fort Morgan (FMV), Highland J virus (HJV), Buggy Creek virus (BCRV), Mucambo virus (MUCV), and Pixuna virus (PIXV). The Old World alphaviruses include any Old World alphavirus, for example Sindbis virus (SINV), Semliki Forest virus (SFV), Chikungunya virus (CHIKV), Bebaru virus (BEBV), O'Nyong Nyong virus (ONNV), Ross River virus (RRV), Sagiyama virus (SAGV), Getah virus (GETV), Middleburg virus (MIDV), Ndumu virus (NDUV), Barmah Forest virus (BFV), Mayaro virus (MAYV), Aura virus (AURA), Una virus, Whataroa virus, Babank virus, and Kyzylagach virus. New World and Old World viruses and their sequences can be used in any combination or sub-combination in the RNA replicons of the invention, and are disclosed in all possible combinations and sub-combinations as if set forth fully herein.

The RNA replicons of the invention can be derived from alphavirus genomes, meaning that they have some of the structural characteristics of alphavirus genomes, or be similar to them. The RNA replicons of the invention can be modified alphavirus genomes. In some embodiments of the replicons disclosed herein one or more sequences of the replicon can be provided "in trans," i.e. the sequences of the replicon are provided on more than one RNA molecule. In other embodiments all of the sequences of the replicon are present on a single RNA molecule, which can also be administered to a mammal to be treated as described herein.

Derived From

The RNA replicons of the invention can contain RNA sequences from (or amino acid sequences encoded by) a wild-type New World or Old World alphavirus genome. Any of the RNA replicons of the invention disclosed herein can contain RNA sequences "derived from" or "based on" wild type alphavirus genome sequences, meaning that they have at least 60% or at least 65% or at least 68% or at least 70% or at least 80% or at least 85% or at least 90% or at least 95% or at least 97% or at least 98% or at least 99% or 100% or 80-99% or 90-100% or 95-99% or 95-100% or 97-99% or 98-99% sequence identity with an RNA sequence (which can be a corresponding RNA sequence) from a wild type RNA alphavirus genome, which can be a New World or Old World alphavirus genome. Any of the nucleic acids or amino acid sequences disclosed herein can be functional or biologically active and operably linked to another sequence required for self-replication of the alphavirus or replicon. A molecule is functional or biologically active if it performs at least 50% of the same activity as its natural (or wild type), corresponding molecule, but a functional molecule can also perform at least 60% or at least 70% or at least 90% or at least 95% or 100% of the same activity as its natural (or wild type) corresponding molecule. The RNA replicons can also encode an amino acid sequence derived from or based on a wild type alphavirus amino acid sequence, meaning that they have at least 60% or at least 65% or at least 68% or at least 70% or at least 80% or at least 70% or at least 80% or at least 90% or at least 95% or at least 97% or at least 98% or at least 99% or 100% or 80-99% or 90-100% or 95-99% or 95-100% or 97-99% or 98-99% sequence identity with an amino acid sequence (which can be a corresponding sequence) encoded by a wild type RNA alphavirus genome, which can be a New World or Old World alphavirus genome. Sequences derived from other sequences can be up to 5% or up to 10% or up to 20% or up to 30% longer or shorter than the original sequence. In any of the embodiments the sequence identity can be at least 95% or at least 97% or at least 98% or at least 99% or 100% for any nucleotide sequence encoding (or amino acid sequence having) a G3BP or FXR binding site thereon. These sequences can also be up to 5% or up to 10% or up to 20% or up to 30% longer or shorter than the original sequence.

Figure 6:
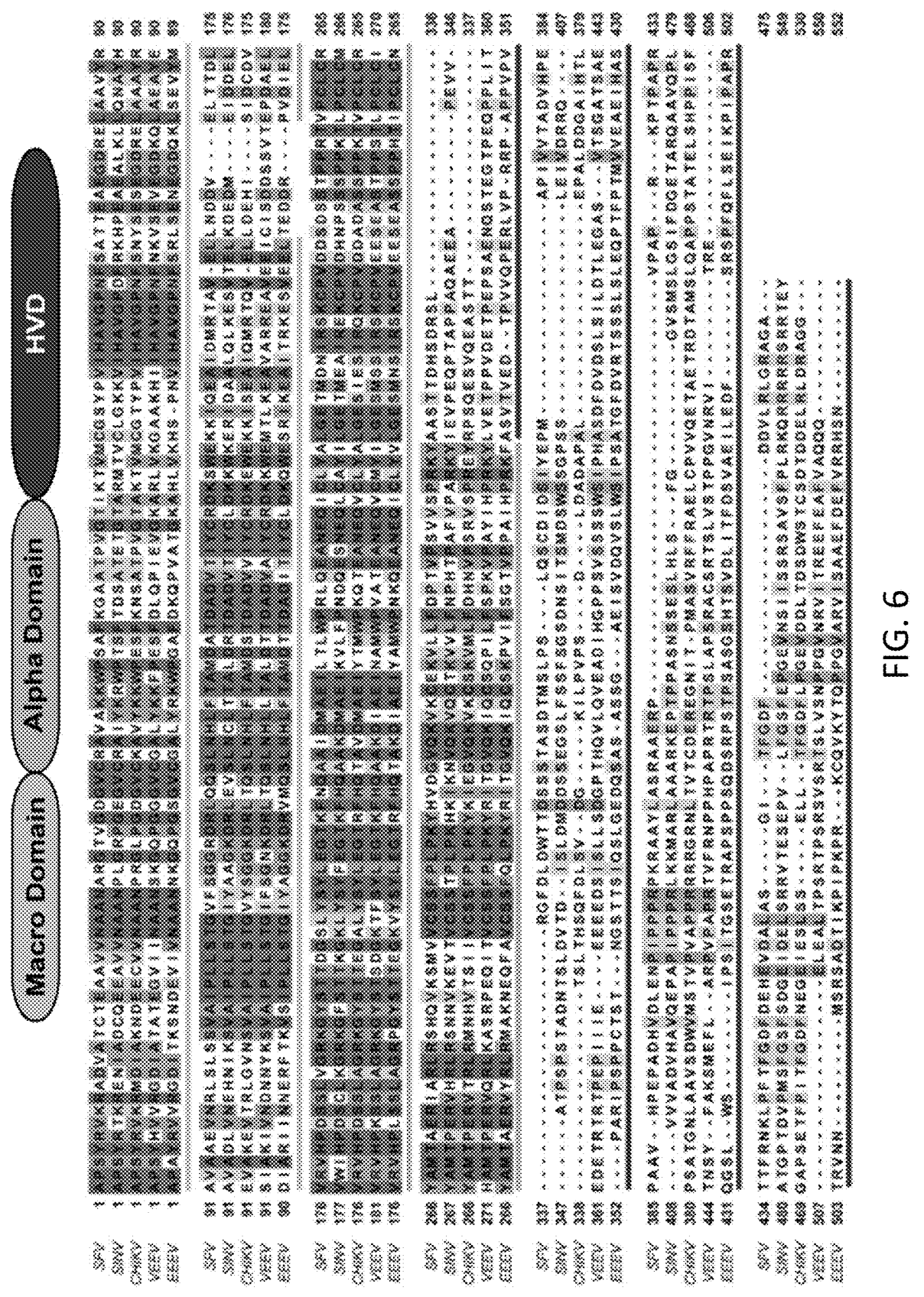

For example, in some embodiments the RNA sequences encoding any one or more of the nsP1, nsP2, nsP3 macro domain, nsP3 central domain, nsP3 hypervariable domain, and/or nsP4 proteins, can be derived from corresponding wild type alphavirus sequences. The "corresponding" sequence can be the analogous sequence in another type of alphavirus. Corresponding sequences are disclosed herein and can also be determined through sequence alignment tools known to persons of ordinary skill (e.g. Clustal Omega). FIG. 6 shows a sequence alignment illustrating the corresponding sequences of nsP3 proteins from representative members of Old World and New World alphaviruses, which was obtained using Clustal Omega. But other sequence alignment tools accepted by persons of ordinary skill in the art can also be used. Programs useful for performing sequence alignments are also found in Molecular Systems Biology (2011) 7, 539. Thus, nsP1, nsP2, nsP3, nsP4 sequences from a New World alphavirus "correspond to" nsP1, nsP2, nsP3, nsP4 sequences from an Old World alphavirus, respectively. Sequences can be corresponding sequences as well. Corresponding amino acid sequences can be at least 5 or at least 10 or at least 15 or at least 20 or at least 25 or at least 30 or at least 52 or at least 53 or at least 75 or at least 100 or at least 125 or at least 150 or at least 175 or at least 200 amino acids, and up to 5% or up to 10% or up to 20% or up to 30% longer or shorter than the original sequence; corresponding nucleic acid sequences can be at least 15 or at least 30 or at least 45 or at least 60 or at least 75 or at least 90 or at least 156 or at least 159 or at least 225 or at least 300 or at least 375 or at least 450 or at least 525 or at least 600 nucleotides. Such sequences can be up to 5% or up to 10% or up to 20% or up to 30% longer or shorter than the original sequence.

In some embodiments of the replicons each of the nsP1, nsP2, and nsP4 sequences can be derived from or based on a New World alphavirus genome. In some embodiments the RNA replicon derived from or based on a wild type New World alphavirus genome can contain at least one RNA sequence (besides at least one heterologous protein or peptide) that is not from a wild type New World alphavirus genome, which can be the sequence of nsP3, or of a central and/or macro domain(s) of nsP3, or of at least a portion of the HVD. In some embodiments the RNA replicon derived from a New World alphavirus genome can have an RNA sequence encoding nsP3, or a domain of nsP3, or a portion of a domain of nsP3 substituted with a corresponding sequence from a wild type Old World alphavirus genome. When referring to the whole replicon “derived from” or “based on” does not count the sequence(s) of RNA that encode(s) the at least one heterologous protein or peptide and, optionally, can also not count the sequence encoding the nsP3 protein, or any one or more the macro domain, the central domain, and/or the HVD domain of nsP3 in any combination or sub-combination.

The term “RNA replicon” refers to RNA which contains all of the genetic information required for directing its own amplification or self-replication within a permissive cell, which can be a human, mammalian, or animal cell. The RNA replicon 1) encodes an RNA-dependent RNA polymerase, which may interact with viral or host cell-derived proteins, nucleic acids or ribonucleoproteins to catalyze the RNA amplification process. The non-structural proteins include nsP1, nsP2, nsP3, nsP4; and 2) contains cis-acting RNA sequences required for replication and transcription of the genomic and subgenomic RNAs, such as 3' and 5' UTRs (alphavirus nucleotide sequences for non-structural protein-mediated amplification), and/or a sub-genomic promoter. These sequences may be bound during the process of replication to self-encoded proteins, or non-self-encoded cell-derived proteins, nucleic acids or ribonucleoproteins, or complexes between any of these components. In some embodiments, a modified RNA replicon molecule typically contains the following ordered elements: 5' viral RNA sequence(s) required in cis for replication (e.g. a 5' UTR and a 5' CSE), sequences coding for biologically active non-structural proteins (e.g. nsP1234), a promoter for transcribing the subgenomic RNA, 3' viral sequences required in cis for replication (e.g. 3' UTR), and a polyadenylate tract, and optionally, a sequence (or two or more sequences) encoding a heterologous protein or peptide after or under the control of a sub-genomic promoter. Further, the term RNA replicon can refer to a positive sense (or message sense) molecule and the RNA replicon can be of a length different from that of any known, naturally-occurring RNA viruses. In any of the embodiments of the present disclosure, the RNA replicon can lack (or not contain) the sequence(s) of at least one (or all) of the structural viral proteins (e.g. nucleocapsid protein C, and envelope proteins P62, 6K, and E1). In these embodiments, the sequences encoding one or more structural genes can be substituted with one or more heterologous sequences such as, for example, a coding sequence for at least one heterologous protein or peptide (or other gene of interest (GOI)).

In various embodiments the RNA replicons disclosed herein can be engineered, synthetic, or recombinant RNA replicons. As used herein, the term recombinant means any molecule (e.g. DNA, RNA, etc.), that is or results, however indirectly, from human manipulation of a polynucleotide. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant RNA replicon can be one or more of the following: 1) synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination) of nucleic acid molecules; 2) conjoined nucleotide sequences that are not conjoined in nature; 3) engineered using molecular cloning techniques such that it lacks one or more nucleotides with respect to the naturally occurring nucleotide sequence; and 4) manipulated using molecular cloning techniques such that it has one or more sequence changes or rearrangements with respect to the naturally occurring nucleotide sequence.

As used herein, the terms “percent identity” or “homology” or “shared sequence identity” or “percent (%) sequence identity” with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertions or deletions shall not be construed as affecting homology, and internal deletions and/or insertions into the polypeptide sequence of less than about 30, less than about 20, or less than about 10 or less than 5 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A BESTFIT® comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

In disclosing the nucleic acid or polypeptide sequences herein, for example sequences of nsP1, nsP2, nsP3, nsP3 macro domain, nsP3 central domain, nsP3 hypervariable domain, nsP4, RdRp, P1234, also disclosed are sequences considered to be based on or derived from the original sequence. Sequences disclosed therefore include polypeptide sequences having sequence identities of at least 40%, at least 45%, at least 50%, at least 55%, of at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or 100% or 85-99% or 85-95% or 90-99% or 95-99% or 97-99% or 98-99% sequence identity with the full-length polypeptide sequence of any polypeptide sequence described herein, such as SEQ ID NOs: 1-29 (and nucleotide sequences encoding any of SEQ ID NOs: 1-29), and fragments thereof. Also disclosed are fragments or portions of any of the sequences disclosed herein. Fragments or portions of sequences can include sequences having at least 5 or at least 7 or at least 10, or at least 20, or at least 30, at least 50, at least 75, at least 100, at least 125, 150 or more or 5-10 or 10-12 or 10-15 or 15-20 or 20-40 or 20-50 or 30-50 or 30-75 or 30-100 amino acid residues of the entire sequence (or a nucleic acid encoding such fragments), or at least 100 or at least 200 or at least 300 or at least 400 or at least 500 or at least 600 or at least 700 or at least 800 or at least 900 or at least 1000 or 100-200 or 100-500 or 100-1000 or 500-1000 amino acid residues (or a nucleic acid encoding such fragments), or any of these amounts but less than 500 or less than 700 or less than 1000 or less than 2000 consecutive amino acids of any of SEQ ID NOs: 1-29 or of any fragment disclosed herein, or a nucleic acid encoding such fragments. Also disclosed are variants of such sequences, e.g., where at least one or two or three or four or five amino acid residues have been inserted N- and/or C-terminal to, and/or within, the disclosed sequence(s) which contain(s) the insertion and substitution, and nucleic acid sequences encoding such variants. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme). The nucleic acid sequences described herein can be RNA sequences.

Any of the components or sequences of the RNA replicon can be operably linked to any other of the components or sequences. The components or sequences of the RNA replicon can be operably linked for the expression of the at least one heterologous protein or peptide (or biotherapeutic) in a host cell or treated organism and/or for the ability of the replicon to self-replicate. The term "operably linked" denotes a functional linkage between two or more sequences that are configured so as to perform their usual function. Thus, a promoter or UTR operably linked to a coding sequence is capable of effecting the transcription and expression of the coding sequence when the proper enzymes are present. The promoter need not be contiguous with the coding sequence, so long as it functions to direct the expression thereof. Thus, an operable linkage between an RNA sequence encoding a heterologous protein or peptide and a regulatory sequence (for example, a promoter or UTR) is a functional link that allows for expression of the polynucleotide of interest. Operably linked can also refer to sequences such as the sequences encoding the RdRp (e.g. nsP4), nsP1-4, the UTRs, promoters, and other sequences encoding in the RNA replicon, are linked so that they enable transcription and translation of the biotherapeutic molecule and/or replication of the replicon. The UTRs can be operably linked by providing sequences and spacing necessary for recognition and translation by a ribosome of other encoded sequences.

G3BP and FXR

Figure 7:
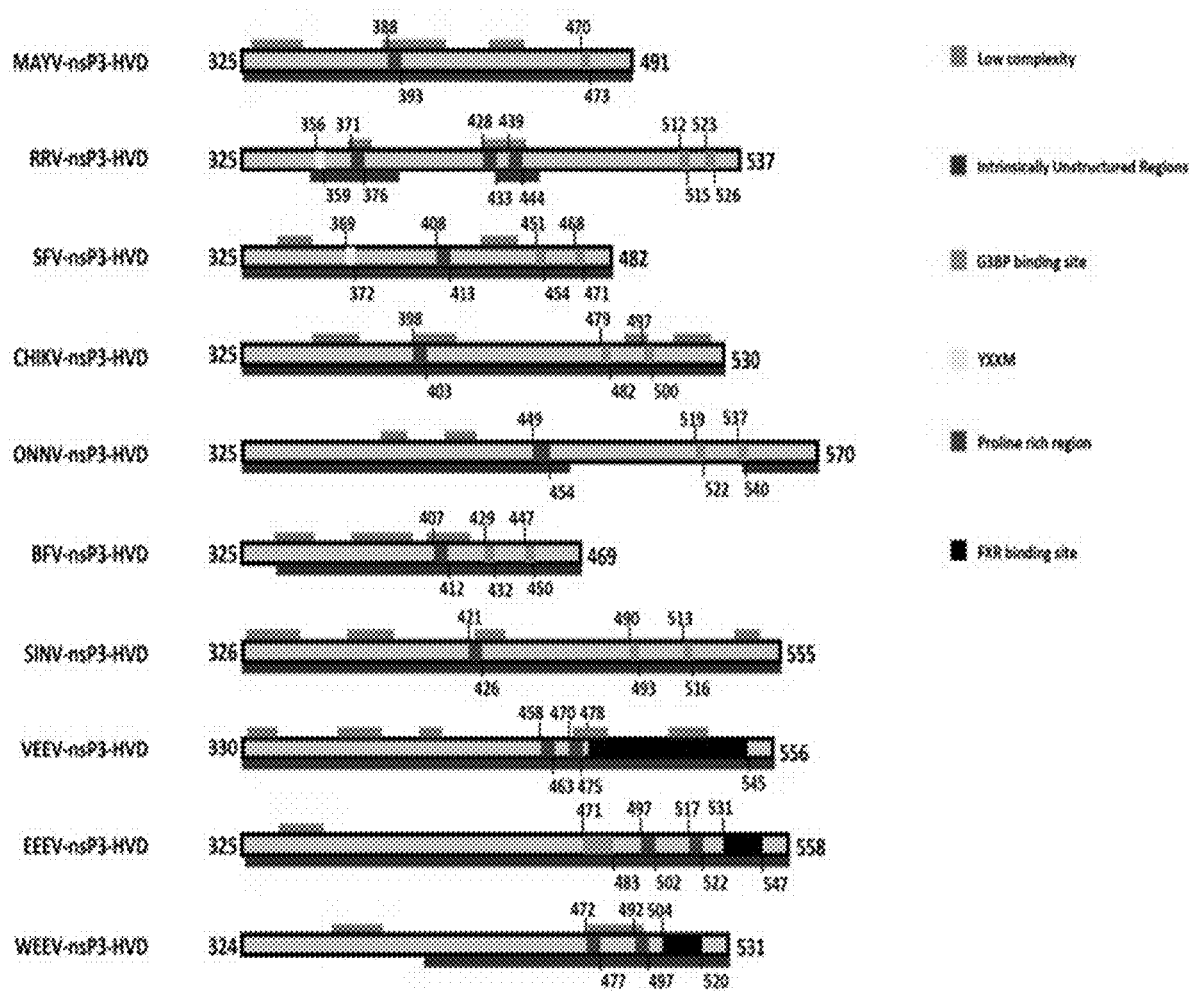
FIG. 7 provides an illustration showing different areas in the HVD of the encoded nsP3 proteins of various New World and Old World viruses (reproduced from FIG. 2 of Gotte et al., Viruses, 2018, 10, 105). The Uniprot entries of nsP3 sequences used for the figure are: MAYV (Q8QZ73), RRV (P13887), SFV (P08411), CHIKV (Q8JUX6), ONNV (Q8QZ73), BFV (P87515), SINV (P03317), VEEV (P36328), EEEV (Q4QXJ8), WEEV (P13896). G3BP binding sites are present for the following Old World virus nsP3 proteins: for MAYV, amino acids 470-473; For RRV, amino acids 512-515 and 523-526; for SFV, amino acids 451-454 and 468-471; for CHIKV, amino acids 479-482 and 497-500; for ONNV, amino acids 519-522 and 537-540; for BFV, amino acids 429-432 and 447-450; for SINV, amino acids 490-493 and 513-516. For New World P1234 viral protein G3BP (and FXR) binding sites are present as follows: for VEEV, amino acids 478-545 have an FXR binding site; for EEEV, amino acids 471-483 have a G3BP binding site and amino acids 531-547 encode an FXR binding site; for WEEV, amino acids 504-520 have an FXR binding site.

G3BP (Ras-GTPase-activating protein (Src-homology 3 (SH3) domain)-binding protein) and FXR (fragile X family proteins) are both RNA binding proteins that self-assemble forming ribonucleoprotein complexes (RNP). Both bind to the HVD domains. The RNP complexes formed by G3BP and FXR perform distinct functions within the cell. For example, G3BP is critical for the nucleation and formation of stress granules in the immune response. Stress granules function to sequester and shut down mRNA translation as well as regulate the induction and secretion of type I interferons and other cytokines. Together these activities reinforce the antiviral state within the cell and promote an adaptive immune response. The FXR family proteins on the other hand are not believed to have a role in innate immunity but associate with polyribosomes and form RNA transport granules in neurons. FIG. 7 indicates areas on various alphavirus nsP3 HVDs where these RNA binding proteins bind to alphavirus sequences.

Non-Structural Proteins

Alphavirus genomes encode non-structural proteins nsP1, nsP2, nsP3, and nsP4, which are produced as a single polyprotein precursor, sometimes designated P1234 (or nsP1-4 or nsP1234), and which is cleaved into the mature proteins through proteolytic processing. nsP1 can be about 60 kDa in size and may have methyltransferase activity and be involved in the viral capping reaction. nsP2 has a size of about 90 kDa and may have helicase and protease activity while nsP3 is about 60 kDa and contains three domains: a macrodomain, a central (or alphavirus unique) domain, and a hypervariable domain (HVD) (See FIG. 6). nsP4 is about 70 kDa in size and contains the core RNA-dependent RNA polymerase (RdRp) catalytic domain. After infection the alphavirus genomic RNA is translated to yield a P1234 polyprotein, which is cleaved into the individual proteins.

nsP3

Alphavirus nsP3 protein contains three domains; a) a macro domain, b) a central (or alpha) domain, and c) a hypervariable domain (HVD). The corresponding amino acid sequences for the three domains of some representative members of Old World and New World alphaviruses are shown in FIG. 6. In various embodiments the replicons of the invention have an RNA sequence encoding an nsP3 macro domain derived from a wild type alphavirus nsP3, and an nsP3 central domain derived from a wild type alphavirus nsP3. In various embodiments the macro and central domain(s) can both be derived from a New World wild type alphavirus nsP3, or can both be derived from an Old World wild type alphavirus nsP3 protein. In some embodiments the macro domain can be derived from a New World wild type alphavirus macro domain and the central domain can be derived from an Old World wild type alphavirus central domain, or vice versa. The various domains can be of any sequence described herein.

Hypervariable Domain (HVD)

In some embodiments the replicons can have a New World alphavirus HVD where the sequence to the C-terminal side of the amino acid where an FXR binding site begins can be deleted and replaced with a replacement sequence of an Old World wild type alphavirus HVD sequence, or portion thereof. Old World alphavirus replacement sequences are described herein. Thus, when the New World alphavirus is VEEV, those amino acids to the C-terminal side of amino acid 478 of the nsP3 can be deleted; when the New World alphavirus is EEEV, those amino acids to the C-terminal side of amino acid 531 of the nsP3 can be deleted; and when the New World alphavirus is WEEV, those amino acids to the C-terminal side of amino acid 504 of the nsP3 can be deleted (see FIG. 7). In any of these embodiments a replacement sequence can be substituted as described herein. As otherwise described herein, a portion of the C-terminal amino acids of the New World alphavirus HVD can be nevertheless retained at the C-terminal side of the Old World sequence.

In some embodiments at least a portion of the sequence encoding the FXR binding site in the New World alphavirus can be deleted and replaced with a replacement sequence, which are described herein. Thus, when the New World alphavirus is VEEV amino acids 478-517 or 478-545 of the nsP3 can be deleted and replaced with a replacement sequence of an Old World alphavirus. Or when the New World alphavirus is VEEV at least one of the repeats present between amino acids 478-545 of the nsP3 can be deleted and optionally replaced with an Old World alphavirus replacement sequence. When the New World alphavirus is EEEV amino acids 531-547 of the nsP3 can be deleted and replaced with an Old World replacement sequence. When the New World alphavirus is WEEV amino acids 504-520 of the nsP3 can be deleted and replaced with an Old World replacement sequence. In other embodiments the entire sequence encoding the FXR binding site can be deleted, or at least 50% or at last 70% or at least 80% or at least 90% of the FXR binding site can be deleted, and optionally replaced with a replacement sequence. In any of the embodiments the indicated sequence can be deleted and no replacement sequence inserted.

The Old World alphavirus replacement sequences can comprise amino acids fragments having one or more G3BP binding sites, or at least a portion of a G3BP binding site. Thus, a replacement sequence can be FGDF (SEQ ID NO: 18) or FGSF (SEQ ID NO: 19). A replacement sequence can also be derived from at least a portion of a wild type nsP3 hypervariable domain of an Old World alphavirus. Further examples of Old World alphavirus replacement sequences are described below. The Old World alphavirus replacement sequences can be used in replicons having sequences of any of the New World alphavirus HVD sequences described herein. In any of the embodiments the New World alphavirus can be VEEV, EEEV, WEEV, or any New World alphavirus described herein.

When the Old World alphavirus is CHIKV, the replacement sequence can be amino acids 479-582 or 479-500 or 479-500 of CHIKV nsP3.

When the Old World alphavirus is SINV, the replacement sequence can be a sequence comprising amino acids 490-493 or 513-516 or 490-516 of SINV nsP3.

When the Old World alphavirus is SFV the replacement sequence can be a sequence comprising amino acids 451-471, or 451-454, or 468-471 of SFV nsP3.

When the Old World alphavirus is MAYV, the replacement sequence can be a sequence comprising amino acids 470-473 of MAYV nsP3.

When the Old World alphavirus is RRV, the replacement sequence can a sequence comprising be amino acids 412-426, or 512-515, or 523-526 of RRV nsP3.

When the Old World alphavirus is ONNV, the replacement sequence can be a sequence comprising amino acids 519-540, or 519-522, or 537-540 of ONNV nsP3.

When the Old World alphavirus is BFV, the replacement sequence can be a sequence comprising amino acids 429-450, or 429-432, or 447-450 of BFV nsP3.

The New World and Old World alphaviruses can be any described herein and can be combined in any possible combination or sub-combination, all of which are disclosed as if set forth fully herein.

The alphavirus genome encodes a core RNA-dependent RNA polymerase in nsP4. Cleavage of the polyprotein may occur at the nsP2/3 junction, influencing the RNA template used during genome replication. After cleavage nsP3 may create a ring structure that encircles nsP2, and these two proteins have a substantial interface. Thus, preservation of the sequences around the junctions of nsP2/3 and/or nsP3/4 may be useful.

Thus, in some embodiments the macro and/or central and/or HVD domains of the nsP3 protein can have the C-terminal and/or the N-terminal portions (as described herein) being an amino acid sequence derived from a New World alphavirus while the remaining portion of the domain(s) is/are derived from an Old World alphavirus sequence. For example, the macro and/or central and/or HVD domains can have a sequence derived from a corresponding Old World alphavirus domain but have the first 4 or 5 or 6 or 4-6 or 6-8 or 6-10 amino acids of the N-terminal and/or the C-terminal of nsP3 being derived from the New World alphavirus sequence (which can be the New World alphavirus from which the nsP1, nsP2, and nsP4 are derived). Thus, the replicon can be as described herein having an RNA sequence encoding an amino acid sequence derived from an Old World alphavirus nsP3 macro and/or central and/or HVD domain and the first 1-3 or 1-4 or 1-5 or 1-6 or 1-7 or 1-8 amino acids on the N-terminal and/or C-terminal side of the domain(s) are derived from a New World alphavirus domain(s), or may have one or two or three substitutions thereon. As used in this context the term "C-terminal" and "N-terminal" do not indicate a true terminus, but the point at which the polyprotein (e.g., P1234) will be cleaved into separate polypeptides (e.g., nsP1, nsP2, nsP3 and nsP4). The sequences encoding the nsPs feature a stop codon and normally transcription will stop at that point. But when the stop codon is treated as a readthrough stop codon the terminus can be the "/" indicated in SEQ ID NOs: 12-17, which can represent the N-terminal and/or C-terminal of the nsPs. The junction sequences can be those 1-6 amino acids on either side of the terminus, e.g. on the nsP3 side. These embodiments allow the nsP3 sequence to be derived from Old World sequences yet preserve the junctions between nsP2/nsP3, and between nsP3/nsP4. The preservation of these junctions may permit cleavage of the P1234 protein junctions using the New World alphavirus enzymes. In some embodiments the penultimate glycine is preserved in the junction. The Old World alphavirus can be any described herein. For example, when the New World alphavirus is VEEV, the nsP2/nsP3 sequence can be LHEAGC/APSY (SEQ ID NO: 12), with the slash ("/") representing the border between nsP2 and nsP3, and with the penultimate G preserved while the remaining amino acids in the nsP2/nsP3 junction are varied as described herein. In the case of the nsP3/nsP4 junction of VEEV, the sequence can be RFDAGA/YIFS (SEQ ID NO: 13), with the penultimate glycine again preserved and the remaining nsP3 amino acids varied as described herein. These sequences can also be preceded by a stop codon (TGA), which as noted above can sometimes be treated as a readthrough stop codon. When the New World alphavirus is EEEV, the nsP2/nsP3 sequence can be QHEAGR/APAY (SEQ ID NO: 14), with the slash ("/") representing the border between nsP2 and nsP3, and with the penultimate G preserved while the remaining amino acids in the nsP2/nsP3 junction are varied as described herein. In the case of the nsP3/nsP4 junction of EEEV, the sequence can be RYEAGA/YIFS (SEQ ID NO: 15), with the penultimate glycine again preserved and the remaining nsP3 amino acids varied as described herein. These sequences can also be preceded by a read-through stop codon (TGA), as above. When the New World alphavirus is WEEV, the nsP2/nsP3 sequence can be RYEAGR/APAY (SEQ ID NO: 16), with the slash ("/") representing the end or terminus of nsP2 (and the junction between nsP2 and nsP3), and with the penultimate G preserved while the remaining amino acids in the nsP2/nsP3 junction are varied as described herein. In the case of the nsP3/nsP4 junction of WEEV, the sequence can be RYEAGA/YIFS (SEQ ID NO: 17), with the penultimate glycine again preserved and the remaining nsP3 amino acids varied as described herein. These sequences can also be preceded by a read-through stop codon (TGA), as explained herein. Any of these sequences (SEQ ID NOs: 12-17) can also contain one or two or three substitutions on the N-terminal and/or C-terminal sides.

Repeat Motifs

Alphaviruses can contain conserved sequence elements (CSEs), which are similar or identical sequences in nucleic acid sequences or polypeptides across species. The CSEs can occur in the HVD of a New World or Old World alphavirus nsP3 and are known in the art.

Old World alphaviruses can also contain FGDF (SEQ ID NO: 18) or FGSF (SEQ ID NO: 19) amino acid motifs, which can repeat in the sequence to form a repeat sequence or repeating motif. In any of the embodiments of the RNA replicon of the invention the HVD of the Old World alphavirus can contain an FGDF/FGDF (SEQ ID NO: 20) repeat, or an FGSF/FGSF (SEQ ID NO: 21) repeat, or an FGDF/FGSF (SEQ ID NO: 22) repeat, or an FGSF/FGDF (SEQ ID NO: 23) repeat. In all embodiments where a repeat is present the two repeating motifs can be separated by one or more amino acid residues. In various embodiments the two repeating motifs can be separated by 5 or 6 or 7 or 8 or 9 or 10 or at least 10 or 11 or 12 or 13 or 14 or 15 or 16 or 17 or 18 or 19 or 20 or 21 or 22 or 23 or 24 or 25 amino acid residues or by more than 25 amino acid residues, which in one embodiment can be random amino acids. In one embodiment the motifs or repeat motifs are separated by at least 10 and not more than 25 amino acids, which also can be random amino acids. In various embodiments the two repeating motifs can be separated by NEGEIESLSSELLT (SEQ ID NO: 6), SDGEIDELSRRVTTESEPVL (SEQ ID NO: 7), or DEHEVDALASGIT (SEQ ID NO: 8), or a sequence derived from any of them, which can be of the same length; thus, disclosed are repeating motifs separated by SEQ ID NOs: 6, 7, or 8, having 1) an FGDF (SEQ ID NO: 18) motif on both ends; 2) an FGSF (SEQ ID NO: 19) motif on both ends; 3) an FGDF (SEQ ID NO: 18) motif on either the 3' or 5' end and an FGSF (SEQ ID NO: 19) motif on the opposite end. In various embodiments amino acid sequences can also follow the second motif. Examples include the amino acid sequence DDVLRLGRAGA (SEQ ID NO: 11) or EPGEVNSIISSRSAVSFPLRKQRRRRRSRRTEY (SEQ ID NO: 10) or LPGEVDDLTDSDWSTCSDTDDELRL-DRAGG (SEQ ID NO: 9), or a sequence derived from any of them, any of which can follow a motif or repeating motif disclosed herein.

Untranslated Regions

Any of the replicons of the invention can also comprise a 5' and a 3' untranslated region (UTR). The UTRs can be wild type New World or Old World alphavirus UTR sequences, or a sequence derived from any of them. In various embodiments the 5' UTR can be of any suitable length, such as about 60 nt or 50-70 nt or 40-80 nt. In some embodiments the 5' UTR can also have conserved primary or secondary structures (e.g. one or more stem-loop(s)) and can participate in the replication of alphavirus or of replicon RNA. In some embodiments the 3' UTR can be up to several hundred nucleotides, for example it can be 50-900 or 100-900 or 50-800 or 100-700 or 200 nt-700 nt. The '3 UTR also can have secondary structures, e.g. a step loop, and can be followed by a polyadenylate tract or poly-A tail. In any of the embodiments of the invention the 5' and 3' untranslated regions can be operably linked to any of the other sequences encoded by the replicon. The UTRs can be operably linked to a promoter and/or sequence encoding a heterologous protein or peptide by providing sequences and spacing necessary for recognition and transcription of the other encoded sequences.

In one embodiment the RNA replicon of the invention can have an RNA sequence encoding a heterologous protein or peptide (e.g. a monoclonal antibody or a biotherapeutic protein or peptide), RNA sequences encoding amino acid sequences derived from a wild type New World alphavirus nsP1, nsP2, and nsP4 protein sequences, and 5' and 3' UTR sequences (for non-structural protein-mediated amplification). The RNA replicons can also have a 5' cap and a polyadenylate (or poly-A) tail. The RNA replicon can also encode an amino acid sequence derived from a New World alphavirus macro domain, an amino acid sequence derived from a New World alphavirus central domain, and an amino acid sequence derived from an Old World alphavirus hypervariable domain. In alternative embodiments the RNA replicon can encode a portion having an amino acid sequence derived from a New World hypervariable domain, and another portion having an amino acid sequence derived from an Old World alphavirus hypervariable domain, as described herein.

The immunogenicity of a heterologous protein or peptide can be determined by a number of assays known to persons of ordinary skill, for example immunostaining of intracellular cytokines or secreted cytokines by epitope-specific T-cell populations, or by quantifying frequencies and total numbers of epitope-specific T-cells and characterizing their differentiation and activation state, e.g., short-lived effector and memory precursor effector CD8+ T-cells. Immunogenicity can also be determined by measuring an antibody-mediated immune response, e.g. the production of antibodies by measuring serum IgA or IgG titers.

Heterologous Proteins and Peptides

The RNA replicons of the invention include an RNA sequence encoding at least one protein or peptide that is heterologous to an alphavirus and can also be (but is not necessarily) heterologous to the human, mammal, or animal that expresses the RNA sequence in the body. In any embodiment the replicons can have RNA sequence(s) encoding two or three or more heterologous proteins or peptides. In various embodiments the heterologous protein or peptide is a biotherapeutic molecule as described herein. While the administration of biotherapeutic molecules to a human, mammal, or animal carries the risk of provoking an anti-drug antibody immune response, the invention allows for the administration of the replicon to the human, mammalian, or animal body, and for expression of the biotherapeutic in the human, mammalian, or animal body, while generating a substantially reduced or no immune response from the cells of human, mammal, or animal receiving the replicon and expressing the biotherapeutic molecule. In any of the embodiments the sequence encoding the heterologous protein or peptide can be operably linked to one or more other sequences of the replicon (e.g. a promoter or 5' or 3' UTR sequences), and can be under the control of a sub-genomic promoter so that the heterologous protein or peptide is expressed in the human, mammal, or animal.

The heterologous protein or peptide can be any protein or peptide and examples include cytokines, growth factors, immunoglobulins, monoclonal antibodies (including Fab antigen-binding fragments, Fc fusion proteins), hormones, interferons, interleukins, regulatory peptides and proteins. Specific examples of monoclonal antibodies that can be the heterologous protein include raxibacumab, tocilizumab, brentuzimab vedotin, Factor IX Fc fusion protein, rilonacept, ofatumumab, bevacizumab, belimumab, certolizumab pegol, ramucirumab, Factor VIII Fc fusion protein, etanercept, vedolizumab, cetuximab, aflibercept, obinutuzumab, trastuzumab, adalimumab, canakinumab, infliximab, ado-trastuzumab emtansine, pembrolizumab, alemtuzumab, ranibizumab, romiplostim, belatacept, abatacept, pertuzumab, denosumab, infliximab, catumaxomab, infliximab, abciximab, rituximab, golimumab, basiliximab, eculizamab, ustekinumab, siltuximab, palivizumab, natalizumab, panitumumab, denosumab, omalizumab, ipilimumab, zivafliber-cept, and ibritumomab tiuxetan. In other embodiments the heterologous protein or peptide can be an endothelial growth factor (e.g. vascular EGF, a hormone (e.g. insulin, relaxin), an exon skipping oligonucleotide, a morpholino oligomer, a morpholino antisense oligomer, or RNAs encoding tumor-specific antigens. In some embodiments the heterologous protein or peptide can be encoded by an RNA sequence of up to 5 kb or up to 6 kb or up to 7 kb or up to 8 kb, or up to 9 kb or up to 10 kb or up to 11 kb or up to 12 kb. The heterologous protein can also be a single-chain antibody molecule.

The alphavirus replicons of the invention can also have a sub-genomic promoter for expression of the heterologous protein or peptide. The term "subgenomic promoter," as used herein, refers to a promoter of a subgenomic mRNA of a viral nucleic acid. As used herein, an "alphavirus subgenomic promoter" is a promoter as originally defined in a wild type alphavirus genome that directs transcription of a subgenomic messenger RNA as part of the alphavirus replication process.

The term "heterologous" when used in reference to a polynucleotide, a gene, a nucleic acid, a polypeptide, a protein, or an enzyme, refers to a polynucleotide, gene, a nucleic acid, polypeptide, protein, or an enzyme that is not derived from the host species. For example, "heterologous gene" or "heterologous nucleic acid sequence" as used herein, refers to a gene or nucleic acid sequence from a different species than the species of the host organism it is introduced into. Heterologous sequences can also be synthetic and not derived from an organism or not found in Nature. When referring to a gene regulatory sequence or to an auxiliary nucleic acid sequence used for manipulating expression of a gene sequence (e.g. a 5' untranslated region, 3' untranslated region, poly A addition sequence, intron sequence, splice site, ribosome binding site, internal ribosome entry sequence, genome homology region, recombination site, etc.) or to a nucleic acid sequence encoding a protein domain or protein localization sequence, "heterologous" means that the regulatory or auxiliary sequence or sequence encoding a protein domain or localization sequence is from a different source than the gene with which the regulatory or auxiliary nucleic acid sequence or nucleic acid sequence encoding a protein domain or localization sequence is juxtaposed in a genome, chromosome or episome. Thus, a promoter operably linked to a gene to which it is not operably linked to in its natural state (for example, in the genome of a non-genetically engineered organism) is referred to herein as a "heterologous promoter," even though the promoter may be derived from the same species (or, in some cases, the same organism) as the gene to which it is linked. Similarly, when referring to a protein localization sequence or protein domain of an engineered protein, "heterologous" means that the localization sequence or protein domain is derived from a protein different from that into which it is incorporated by genetic engineering.

The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector or a replicon. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exo-nucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector or that has been integrated into an RNA replicon.

Methods

The invention also provides methods of administering a nucleic acid to a human, mammal, or animal patient. The nucleic acid can be an RNA sequence that encodes a protein or peptide (which can be a heterologous protein or peptide).

The methods involve administering to the patient an RNA replicon described herein, wherein a protein or peptide encoded by the replicon is expressed (or transcribed) in the patient, which can be done utilizing the patient body's cellular components. In any of the (non-limiting) embodiments herein, the mammal can be a human, a domestic animal, food animals, or a companion animal. The animal can also be any bird, fish (e.g. of the Salmonidae family), poultry, or fowl, e.g. a chicken, duck, goose, turkey, ostrich, emu, swan, peafowl, pheasant, partridge, or guinea fowl. The replicon can be administered in a pharmaceutically acceptable carrier, for example saline, water, or another acceptable carrier.

As used herein, "pharmaceutically acceptable carrier" means any substance suitable for use in administering to an individual. For example, a pharmaceutically acceptable carrier can be a sterile aqueous solution, such as phosphate buffer saline (PBS), or water-for-injection. In some embodiments, the pharmaceutically acceptable carrier can be a buffer, a preservative, an isotonic agent, a stabilizer, a surfactant, a wetting agent, an emulsifier, an antioxidant, a bulking agent, or a chelating agent. Such additional ingredients, of course, should not adversely affect the overall stability of the pharmaceutical formulation of the present invention.

The replicon can also be administered as a pharmaceutically acceptable salt. As used herein, "pharmaceutically acceptable salts" means physiologically and pharmaceutically acceptable salts of compounds, such as nucleic acid compounds or polynucleotides, i.e., salts that retain the desired biological activity of the parent compound and do not impart undesired toxicological effects thereto. Pharmaceutically acceptable acidic/anionic salts for use in the invention include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid. Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, chloroprocaine, choline, cyclohexylamine, diethanolamine, ethylenediamine, lithium, L-lysine, magnesium, meglumine, N-methyl-D-glucamine, piperidine, potassium, procaine, quinine, sodium, triethanolamine, or zinc.

The invention also provides methods of administering a heterologous protein or peptide to a mammal comprising administering to the mammal an RNA replicon described herein that encodes the heterologous protein or peptide, and wherein the heterologous protein or peptide is expressed within the mammal. The method allows administration of the heterologous protein or peptide to the mammal with a lower or eliminated immune response from the mammal versus administration of the naked heterologous protein and peptide.

EMBODIMENTS

Embodiment 1 is an RNA replicon comprising
an RNA sequence encoding a heterologous protein or peptide;
5' and 3' alphavirus untranslated regions;
RNA sequences encoding amino acid sequences derived from New World alphavirus nonstructural proteins nsP1, nsP2, and nsP4; and
an RNA sequence encoding an amino acid sequence derived from an alphavirus nsP3 macro domain;
an RNA sequence encoding an amino acid sequence derived from an alphavirus nsP3 central domain; and
an RNA sequence encoding an amino acid sequence derived from an alphavirus nsP3 hypervariable domain comprising
  a. an amino acid sequence derived from an Old World alphavirus nsP3 hypervariable domain; or
  b. an amino acid sequence comprising a portion derived from a New World alphavirus nsP3 hypervariable domain, and a portion derived from an Old World alphavirus nsP3 hypervariable domain.

Embodiment 2 is the RNA replicon of embodiment 1, wherein the alphavirus nsP3 macro domain and the alphavirus nsP3 central domain are from a New World alphavirus.

Embodiment 3 is the RNA replicon of embodiment 1, wherein the alphavirus nsP3 macro domain and the alphavirus nsP3 central domain are from an Old World alphavirus.

Embodiment 4 is the RNA replicon of any one of embodiments 1 to 3, wherein the alphavirus nsP3 hypervariable domain comprises the amino acid sequence derived from the Old World alphavirus nsP3 hypervariable domain.

Embodiment 5 is the RNA replicon of any one of embodiments 1 to 4, wherein the Old World alphavirus is selected from the group consisting of: CHIKV, SINV, and SFV.

Embodiment 6 is the RNA replicon of any one of embodiments 1 to 5, wherein the New World alphavirus is Venezuelan Equine Encephalitis Virus (VEEV).

Embodiment 7 is the RNA replicon of any one of embodiments 1 to 5, wherein the New World alphavirus is Venezuelan Equine Encephalitis Virus (EEEV).

Embodiment 8 is the RNA replicon of any one of embodiments 1 to 5, wherein the New World alphavirus is selected from the group consisting of: a Venezuelan equine encephalitis virus (VEEV), a western equine encephalitis virus (WEEV), and an eastern equine encephalitis virus (EEEV).

Embodiment 9 is the RNA replicon of any one of embodiments 1 to 8, wherein the Old World alphavirus is selected from the group consisting of: Sindbis virus (SINV), Chickungunya virus (CHIKV), Semliki Forest Virus (SFV), Ross River Virus (RRV), Sagiyama virus (SAGV), Getah virus (GETV), Middleburg virus (MIDV), Bebaru virus (BEBV), O'nyong nyong virus (ONNV), Ndumu (NDUV), and Barmah Forest virus (BFV).

Embodiment 10 is the RNA replicon of any one of embodiments 1 to 9, wherein the portion derived from the Old World alphavirus nsP3 hypervariable domain comprises a motif selected from the group consisting of: FGDF (SEQ ID NO: 18) and FGSF (SEQ ID NO: 19).

Embodiment 11 is the RNA replicon of any one of embodiments 1 to 10, wherein the portion derived from the Old World alphavirus nsP3 hypervariable domain comprises a repeat selected from the group consisting of: an FGDF/

FGDF (SEQ ID NO: 20) repeat, an FGSF/FGSF (SEQ ID NO: 21) repeat, an FGDF/FGSF (SEQ ID NO: 22) repeat, and an FGSF/FGDF (SEQ ID NO: 23) repeat; and further wherein the repeat sequences are separated by at least 10 and not more than 25 amino acids.

Embodiment 12 is the RNA replicon of embodiment 11, wherein the repeat sequence is separated by an amino acid sequence derived from the group consisting of: NEGEIESLSSELLT (SEQ ID NO: 6), SDGEIDELSRRVT-TESEPVL (SEQ ID NO: 7), and DEHEVDALASGIT (SEQ ID NO: 8).

Embodiment 13 is the RNA replicon of any one of embodiments 1 to 12, wherein the portion derived from the Old World alphavirus hypervariable domain comprises amino acids 479-482 or 497-500 or 479-500 or 335-517 of CHIKV nsP3 HVD; or amino acids 451-454 or 468-471 or 451-471 of SFV nsP3 HVD; or amino acids 490-493 or 513-516 or 490-516 or 335-538 of SINV nsP3 HVD.

Embodiment 14 is the RNA replicon of any one of embodiments 1 to 12, wherein the portion derived from the Old World alphavirus hypervariable domain comprises amino acids 479-500 or 335-517 of CHIKV nsP3 HVD; or amino acids 451-471 of SFV nsP3 HVD; or amino acids 490-516 of SINV nsP3 HVD.

Embodiment 15 is the RNA replicon of embodiment 13, wherein the New World alphavirus is VEEV and the portion derived from the New World alphavirus hypervariable domain does not comprise amino acids 478-518 of the VEEV nsP3 hypervariable domain.

Embodiment 16 is the RNA replicon of embodiment 13, wherein the New World alphavirus is VEEV and the portion derived from the New World alphavirus hypervariable domain does not comprise amino acids 478-545 of the VEEV nsP3 hypervariable domain.

Embodiment 17 is the RNA replicon of embodiment 13, wherein the New World alphavirus is VEEV and the portion derived from the New World alphavirus hypervariable domain does not comprise amino acids 335-518 of the VEEV nsP3 hypervariable domain.

Embodiment 18 is the RNA replicon of embodiment 14, wherein the Old World alphavirus is CHIKV and the portion derived from the Old World alphavirus hypervariable domain comprises amino acids 335-517 of the CHIKV nsP3.

Embodiment 19 is the RNA replicon of embodiment 14, wherein the Old World alphavirus is SINV and the portion derived from the Old World alphavirus hypervariable domain comprises amino acids 335-538 of the SINV nsP3.

Embodiment 20 is the RNA replicon of embodiment 13, wherein the New World alphavirus is EEEV, and the portion derived from the New World alphavirus hypervariable domain does not comprise amino acids 531-547 of the EEEV nsP3 hypervariable domain.

Embodiment 21 is the RNA replicon of embodiment 20, wherein the New World alphavirus is EEEV, and the portion derived from the New World alphavirus hypervariable domain does not comprise amino acids 531-547 of the EEEV nsP3 hypervariable domain, and wherein the portion derived from the Old World alphavirus hypervariable domain comprises amino acids 479-500 of CHIKV nsP3 HVD;
amino acids 451-471 of SFV nsP3 HVD; or
amino acids 490-516 of SINV nsP3 HVD.

Embodiment 22 is the RNA replicon of embodiment 13, wherein the New World alphavirus is WEEV, and the portion derived from the New World alphavirus hypervariable domain does not comprise amino acids 504-520 of the WEEV nsP3 hypervariable domain.

Embodiment 23 is the RNA replicon of embodiment 22, wherein the New World alphavirus is WEEV, and the portion derived from the New World alphavirus hypervariable domain does not comprise amino acids 504-520 of the WEEV nsP3 hypervariable domain, and wherein the portion derived from the Old World alphavirus hypervariable domain comprises
amino acids 479-500 of CHIKV nsP3 HVD; or
amino acids 451-471 of SFV nsP3 HVD; or
amino acids 490-516 of SINV nsP3 HVD.

Embodiment 24 is the RNA replicon of any one of embodiments 1 to 23, further comprising a sub-genomic promoter that is operably linked to and regulates translation of the RNA sequence encoding the heterologous protein.

Embodiment 25 is the RNA replicon of any one of embodiments 1 to 24, further comprising a 5' cap and a 3' poly-A tail.

Embodiment 26 is the RNA replicon of any one of embodiments 1 to 25, wherein the replicon comprises positive sense, single-stranded RNA.

Embodiment 27 is the RNA replicon of any one of embodiments 1 to 26, wherein the replicon comprises 10-12 kb of RNA and has a diameter of 30-50 nm.

Embodiment 28 is the RNA replicon of any one of embodiments 1 to 27, wherein the heterologous protein is a biotherapeutic protein or peptide.

Embodiment 29 is the RNA replicon of any one of embodiments 1 to 28, wherein the heterologous protein is an antibody.

Embodiment 30 is the RNA replicon of embodiment 1, wherein the New World alphavirus is VEEV, and the alphavirus nsP3 hypervariable domain comprises a portion derived from the New World alphavirus nsP3 hypervariable domain not comprising amino acids 335-518 of the VEEV nsP3 hypervariable domain, and a portion derived from an Old World alphavirus nsP3 hypervariable domain comprising amino acids 490-493 or 513-516 or 490-516 or 335-538 of SINV nsP3 HVD.

Embodiment 31 is the RNA replicon of embodiment 30, wherein the portion derived from an Old World alphavirus nsP3 hypervariable domain comprises amino acids 490-516 of SINV nsP3 HVD.

Embodiment 32 is the RNA replicon of embodiment 30, wherein the Old World alphavirus is SINV and the portion derived from an Old World alphavirus nsP3 hypervariable domain comprises amino acids 335-538 of SINV nsP3 HVD.

Embodiment 33 is the RNA replicon of any one of embodiments 1 to 32 wherein the RNA sequence encoding the heterologous protein or peptide is operably linked to the RNA sequence encoding the nsP1, nsP2, and nsP4.

Embodiment 34 is a method of administering a heterologous protein or peptide to a mammal, comprising administering to the mammal an RNA replicon of any one of embodiments 1 to 33 that encodes the heterologous protein or peptide, and wherein the heterologous protein or peptide is expressed within the mammal.

Embodiment 35 is the method of embodiment 34, wherein the New World alphavirus is VEEV and the RNA replicon is a replicon of embodiment 14.

Embodiment 36 is the method of embodiment 34, wherein the RNA replicon is a replicon of embodiment 19.

Embodiment 37 is the method of embodiment 34, wherein the RNA replicon is a replicon of embodiment 22.

Embodiment 38 is the method of embodiment 34, wherein the RNA replicon is a replicon of embodiment 25.

Embodiment 39 is an RNA replicon comprising
an RNA sequence encoding a heterologous protein or peptide;
RNA sequences encoding amino acid sequences derived from New World alphavirus nonstructural proteins nsP1, nsP2, and nsP4; and
an RNA sequence encoding an amino acid sequence derived from an Old World alphavirus nsP3 protein, and wherein the first 1-6 amino acids on the N-terminal and/or C-terminal side of the nsP3 protein are derived from a New World alphavirus sequence.

Embodiment 40 is an alphavirus replicon RNA, comprising: in the order from the 5' to 3'end,
(1) an alphavirus 5' untranslated sequence for directing replication of the alphavirus replicon;
(2) an RNA sequence encoding alphaviral nonstructural proteins nsP1, nsP2, nsP3, and nsP4;
(3) an alphavirus subgenomic promoter sequence,
(4) an RNA sequence encoding one or more heterologous proteins or peptides, and
(5) an alphavirus 3' untranslated sequence,
wherein the nsP1, nsP2 and nsP4 are from one or more New World alphaviruses, and
the nsP3 comprises, in the order from the amino-terminus to the carboxyl terminus, a macro domain, a central domain and a hypervariable domain (HVD), wherein
the macro domain and the central domain are from one or more New World alphaviruses and/or Old World alphaviruses; and
the HVD is from an Old World alphavirus, or the HVD comprises a portion of an HVD from a New World alphavirus and a portion of an HVD from an Old World alphavirus.

Embodiment 41 is the alphavirus replicon RNA of embodiment 40, wherein the nsP1, nsP2 and nsP4 are from one or more New World alphaviruses selected from the group consisting of a Venezuelan equine encephalitis virus (VEEV), a western equine encephalitis virus (WEEV), and an eastern equine encephalitis virus (EEEV).

Embodiment 42 is the alphavirus replicon RNA of embodiment 40, wherein the nsP1, nsP2 and nsP4 are from a Venezuelan equine encephalitis virus (VEEV).

Embodiment 43 is the alphavirus replicon RNA of any one of embodiments 40-42, wherein the Old World alphavirus is selected from the group consisting of: Sindbis virus (SINV), Chickungunya virus (CHIKV), Semliki Forest Virus (SFV), Ross River Virus (RRV), Sagiyama virus (SAGV), Getah virus (GETV), Middleburg virus (MIDV), Bebaru virus (BEBV), O'nyong nyong virus (ONNV), Ndumu (NDUV), and Barmah Forest virus (BFV).

Embodiment 44 is the alphavirus replicon RNA of embodiment 43, wherein the Old World alphavirus is Sindbis virus (SINV), Chickungunya virus (CHIKV) or Semliki Forest Virus (SFV).

Embodiment 45 is the alphavirus replicon RNA of any one of embodiments 4044, wherein the macro domain and the central domain are from one or more Old World alphaviruses.

Embodiment 46 is the alphavirus replicon RNA of any one of embodiments 4044, wherein the macro domain and the central domain are from one or more New World alphaviruses.

Embodiment 47 is the alphavirus replicon RNA of embodiment 40, wherein the nsP1, nsP2 and nsP4, the macro domain and the central domain are from a Venezuelan equine encephalitis virus (VEEV), and the HVD comprises a portion of an HVD from the VEEV and a portion of an HVD from an Old World alphavirus selected from a group consisting of Sindbis virus (SINV), Chickungunya virus (CHIKV) and Semliki Forest Virus (SFV).

Embodiment 48 is the alphavirus replicon RNA of embodiment 47, wherein the HVD comprises the HVD from the VEEV, except that amino acid residues 335-538 of the nsP3 of the VEEV are substituted with amino acid residues 335-538 of the nsP3 of the SINV.

Embodiment 49 is the alphavirus replicon RNA of embodiment 47, wherein the HVD comprises the HVD from the VEEV, except that amino acid residues 335-518 of the nsP3 of the VEEV are substituted with amino acid residues 335-517 of the nsP3 of the CHIKV.

Example 1—Immunogenicity of VEEV-Based Replicon

A VEEV-based alphavirus replicon encoding a mutant nsP3 was constructed by replacing the nucleotide sequence encoding amino acids 335-518 of VEEV nsP3 with a nucleotide sequence encoding amino acids 335-517 of the Chikungunya (CHIKV) nsP3 to create a VEEV based replicon expressing a VEEV/CHIKV nsP3 chimera (SEQ ID NO: 30). This replacement removed the first motif of a repeat sequence from VEEV, and replaced it with a FGDF/FGDF (SEQ ID NO: 20) repeat sequence from the CHIKV genome (at amino acids 479-482 and 497-500). In a parallel experiment, amino acids 335-538 of VEEV nsP3 (HVD region) were replaced with amino acids 335-538 of Sindbis virus (SINV) nsP3 amino acids (HVD region) to generate a replicon encoding a VEEV/SINV nsP3 chimera (SEQ ID NO: 31) (See FIGS. 2 and 7). This replacement removed a repeat sequence from VEEV and replaced it with a FGSF/FGSF (SEQ ID NO: 21) repeat sequence from SINV. Replicons containing the WT, VEEV/CHIKV or VEEV/SINV chimeric nsP3 and expressing a red firefly luciferase (rFF) reporter from the subgenomic RNA (SGIα-rFF) were delivered into BHK-21 cells in triplicate by electroporation. Following electroporation, a portion of the cells were plated into one well of a 6 well plate and one well of a 96 well plate and allowed to recover for 20 hours. Electroporated cells were stained for the presence of dsRNA and analyzed by flow cytometry to determine the frequency of dsRNA positive cells as a measure of replicon amplification. Replicons containing mutant nsP3 were found to replicate to the same levels as a replicon containing a WT nsP3 (FIG. 2B). When analyzed for luciferase activity no difference was seen between replicons containing WT or the indicated mutant forms of nsP3 (FIG. 2C).

Example 2—Expression of Heterologous Protein from Replicon

Figure 3A:
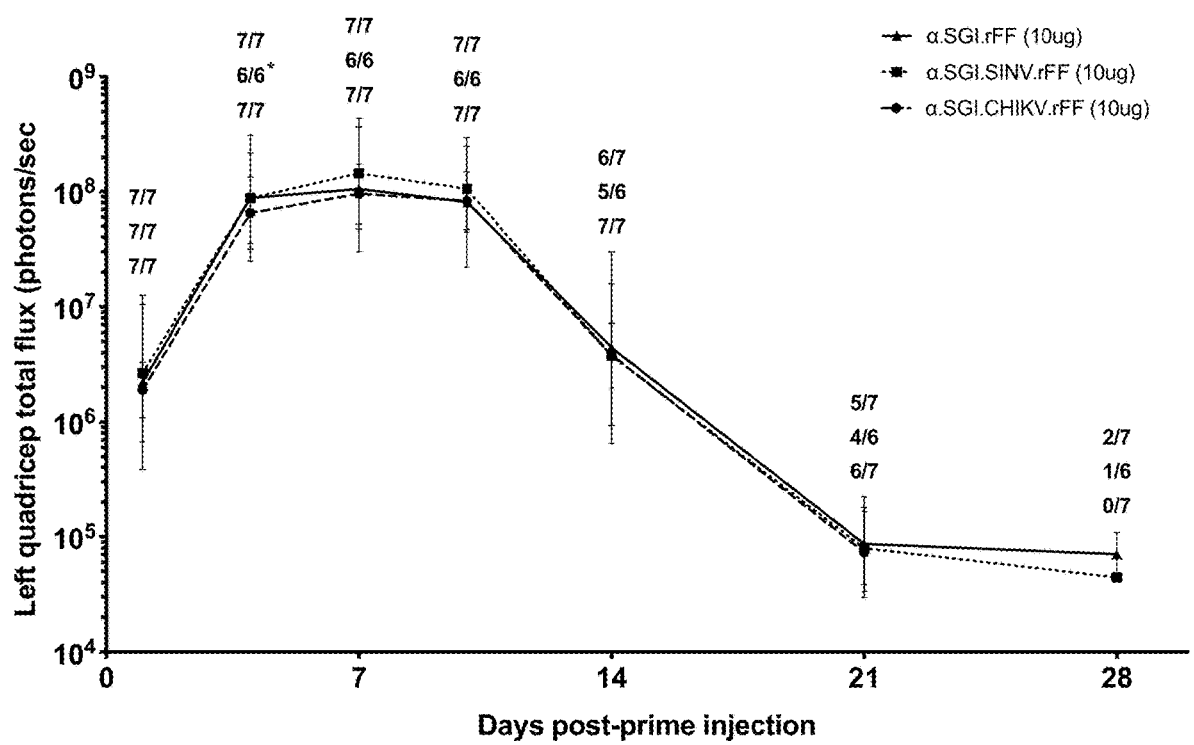
FIG. 3A-FIG. 3B.
Figure 3B:
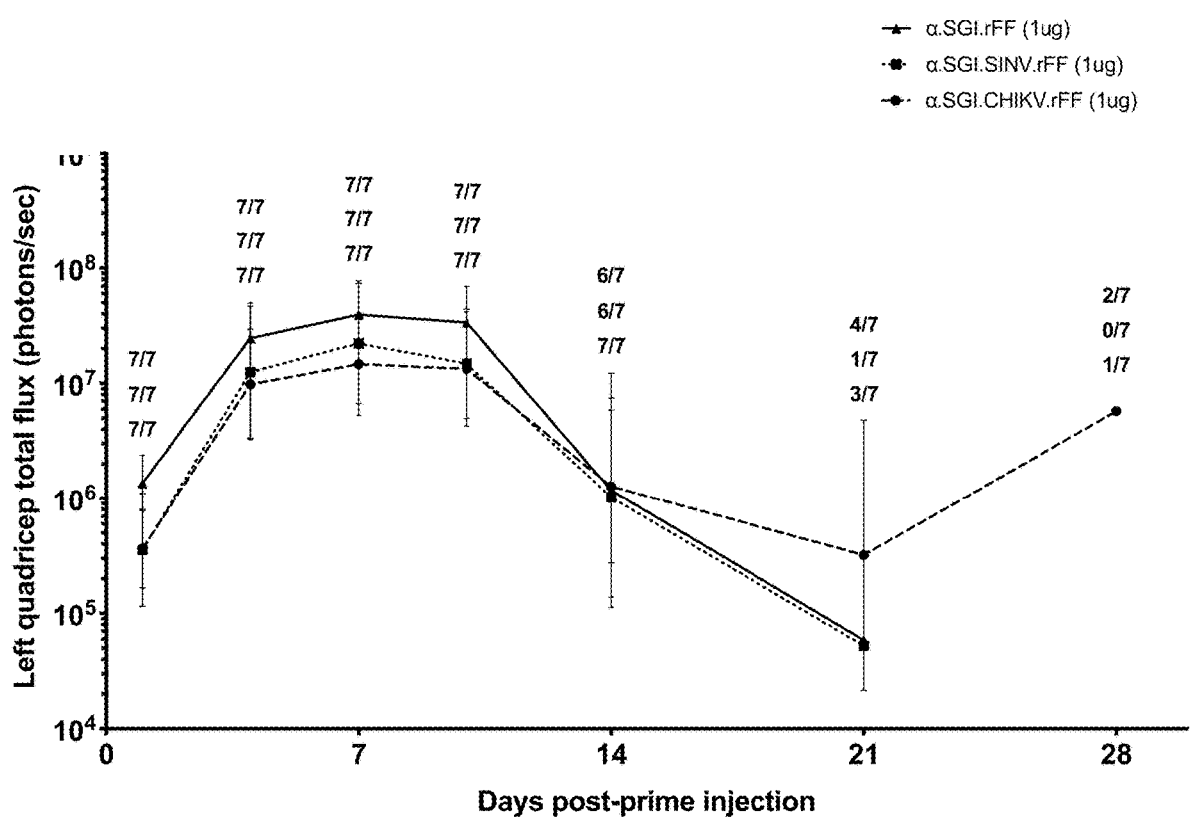

This example examined in vivo expression of recombinant firefly luciferase (rFF) from replicons (Example 1) encoding the mutant nsP3 as described in FIG. 2A. One or ten micrograms of replicon RNA in saline was delivered intramuscularly (IM) into the quadricep muscle of BALB/c mice. At indicated time points luciferase activity was monitored in vivo using a commercially available in vivo imaging system and reported as total flux (FIGS. 3A and 3B). The data show that replicons expressing mutant forms of nsP3 exhibited similar levels of luciferase activity in vivo compared to a replicon containing wild type nsP3 from VEEV.

Example 3—Immunogenicity

Figure 4:
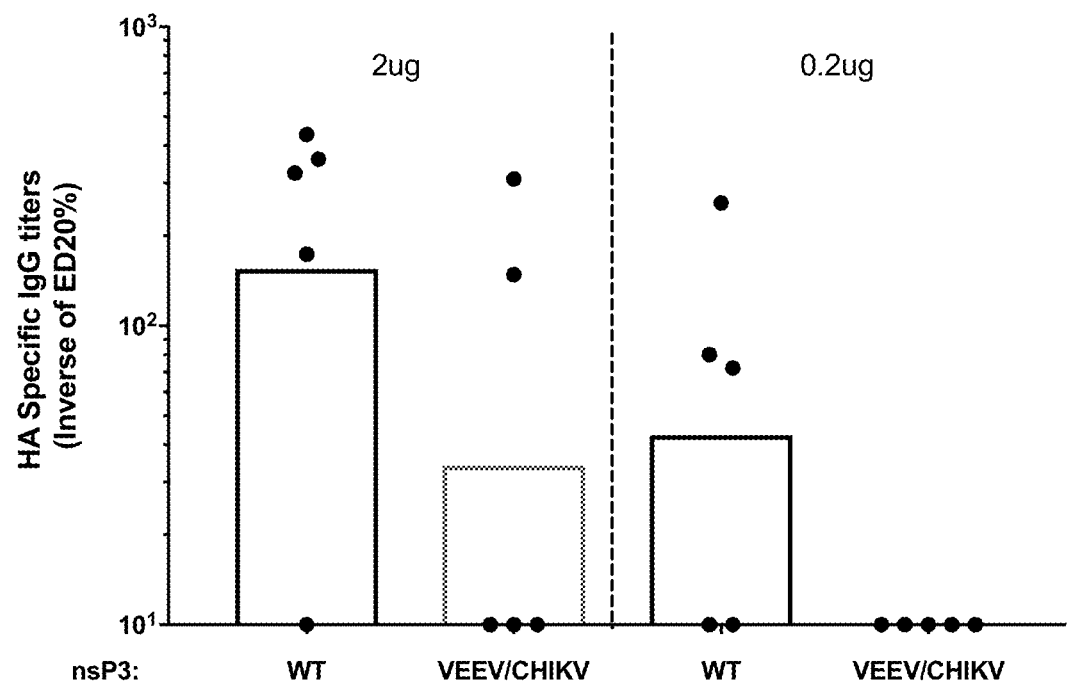

This example examined the immunogenicity of a VEEV-based replicon encoding a VEEV/CHIKV chimeric form of nsP3 (from Example 1) versus the immunogenicity of a replicon with a wild type (WT) VEEV nsP3. Each replicon encoded and expressed hemagglutinin (HA) from the H5N1 strain of influenza as the heterologous protein. 2.0 ug or 0.2 ug of RNA in saline was delivered intra-muscularly to the quadricep muscle of BALB/c mice at day 0 and boosted with the same replicon RNA and dose at day 28. Two weeks post boost (day 42 post prime) spleens and serum were collected. Serum was analyzed for HA specific antibodies by ELISA (FIG. 4). The data show that replicons encoding an a VEEV/CHIKV nsP3 chimera significantly reduced HA specific IgG titers compared to a replicon with wild type nsP3.

Figure 5A:
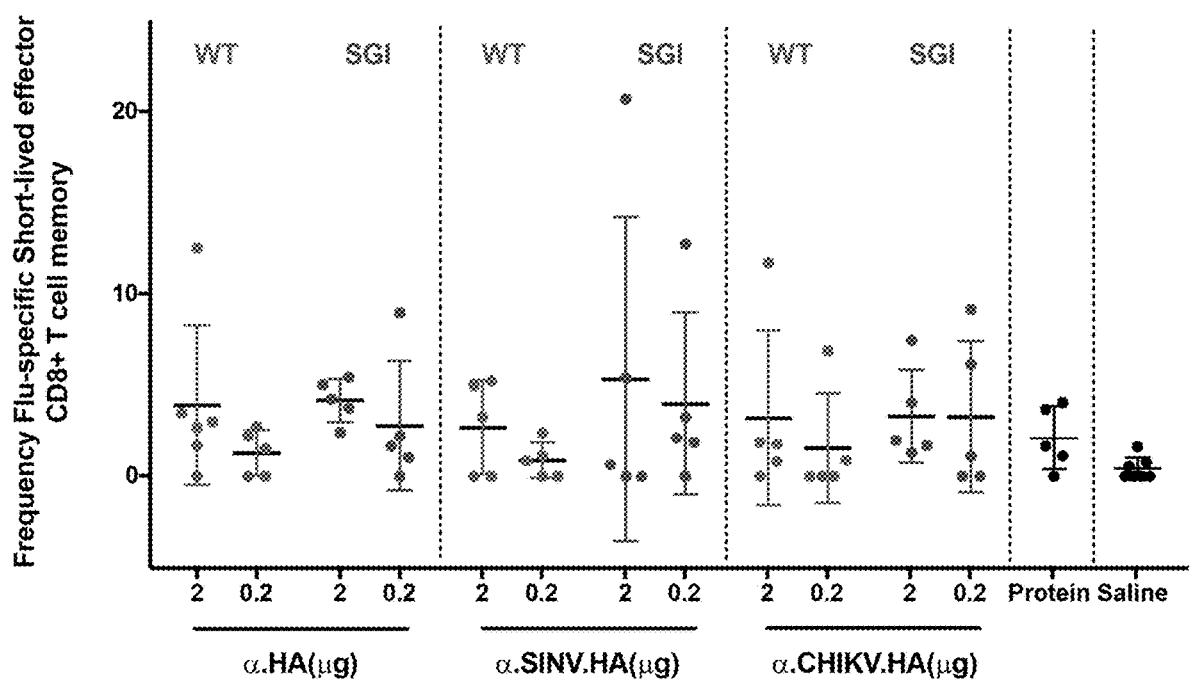
FIG. 5A-FIG. 5B.
Figure 5B:
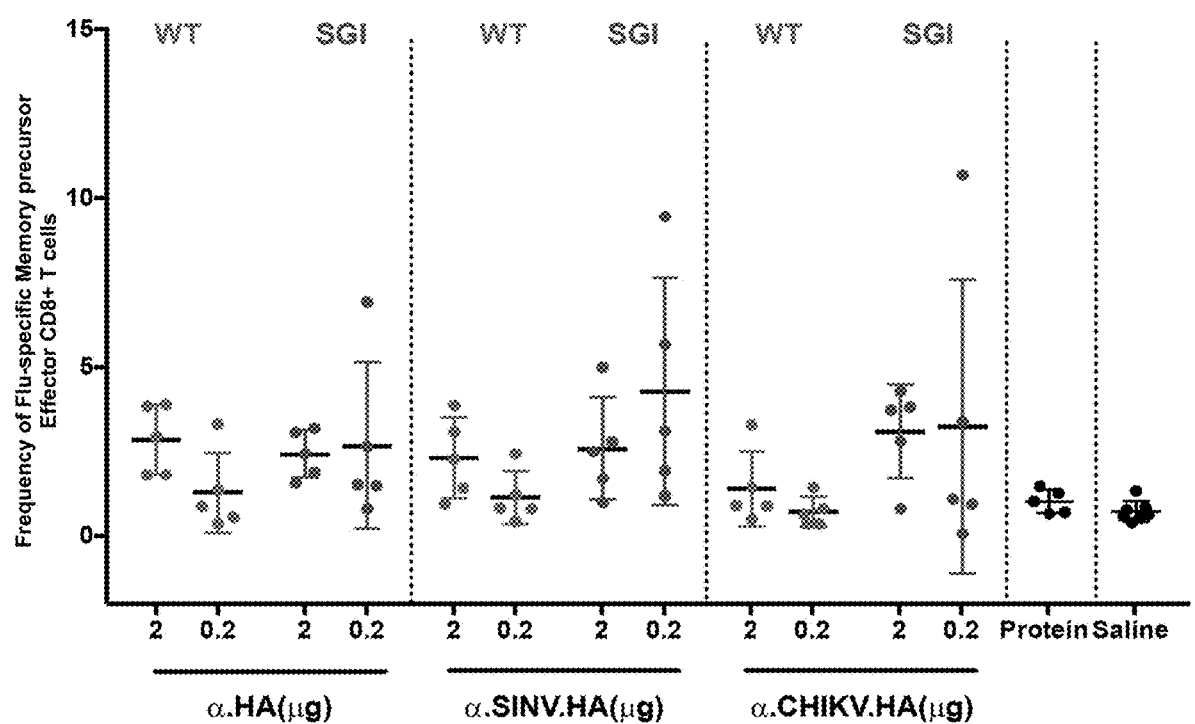

In contrast, analysis of the short-lived effector and memory precursor effector CD8+ T cells showed no difference in the frequency of HA specific cells between the different replicons tested (FIGS. 5A and 5B). FIG. 5A shows similar frequency of HA specific short-lived effector CD8+ T cells between the wild type, VEEV/SINV nsP3, and VEEV/CHIKV nsP3 RNA replicons. FIG. 5B shows a similar result for memory effector CD8+ T cells.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Other embodiments are within the following claims.

We claim:

1. An RNA replicon comprising
   (i) an RNA sequence encoding a heterologous protein or peptide;
   (ii) 5' and 3' alphavirus untranslated regions;
   (iii) RNA sequences encoding amino acid sequences derived from New World alphavirus nonstructural proteins nsP1, nsP2, and nsP4; and
   (iv) an RNA sequence encoding a nonstructural nsP3, wherein said nsP3 comprises (a) an amino acid sequence derived from an alphavirus nsP3 macro domain;
   (b) an RNA sequence encoding an amino acid sequence derived from an alphavirus nsP3 central domain; and
   (c) an RNA sequence encoding an amino acid sequence derived from an alphavirus nsP3 hypervariable domain (HVD) comprising at least a portion of an Old World alphavirus nsP3 HVD comprising a FGDF (SEQ ID NO: 18) or a FGSF (SEQ ID NO: 19) motif, wherein said alphavirus nsP3HVD comprises:

an amino acid sequence derived from an Old World alphavirus nsP3 HVD comprising said portion of the Old World alphavirus nsP3 HVD; or
   an amino acid sequence comprising a portion derived from a New World alphavirus nsP3 HVD, and said portion derived from the Old World alphavirus nsP3 HVD; and wherein the replicon does not encode at least protein C.

2. The RNA replicon of claim 1, wherein the Old World alphavirus is selected from the group consisting of: Sindbis virus (SINV), Chickungunya virus (CHIKV), Semliki Forest Virus (SFV), Ross River Virus (RRV), Sagiyama virus (SAGV), Getah virus (GETV), Middleburg virus (MIDV), Bebaru (BEBV), O'nyong nyong virus (ONNV), Ndumu (NDUV), and Barmah Forest virus (BFV).

3. The RNA replicon of claim 2, wherein the Old World alphavirus is selected from the group consisting of: CHIKV, SINV, and SFV.

4. The RNA replicon of claim 1, wherein the New World alphavirus is selected from the group consisting of: a Venezuelan equine encephalitis virus (VEEV), a western equine encephalitis virus (WEEV), and an eastern equine encephalitis virus (EEEV).

5. The RNA replicon of claim 1, wherein the portion derived from the Old World alphavirus nsP3 HVD comprises a repeat selected from the group consisting of: an FGDF/FGDF (SEQ ID NO: 20) repeat, an FGSF/FGSF (SEQ ID NO: 21) repeat, an FGDF/FGSF (SEQ ID NO: 22) repeat, and an FGSF/FGDF (SEQ ID NO: 23) repeat; and further wherein the repeat sequences are separated by at least 10 but not more than 25 amino acids.

6. The RNA replicon of claim 5, wherein the repeat sequence is separated by an amino acid sequence selected from the group consisting of: NEGEIESLSSELLT (SEQ ID NO: 6), SDGEIDELSRRVTTESEPVL (SEQ ID NO: 7), or DEHEVDALASGIT (SEQ ID NO: 8).

7. The RNA replicon of claim 1, wherein the alphavirus nsP3 HVD comprises a portion derived from the Old World alphavirus nsP3 HVD having:
   a. amino acids 479-482 or 497-500 or 479-500 or 335-517 of CHIKV nsP3 HVD;
   b. amino acids 451-454 or 468-471 or 451-471 of SFV nsP3 HVD; or
   c. amino acids 490-493 or 513-516 or 490-516 or 335-538 of SINV nsP3 HVD.

8. The RNA replicon of claim 7, wherein the portion derived from the Old World alphavirus nsP3 HVD comprises amino acids 335-517 of CHIKV nsP3 HVD or amino acids 335-538 of SINV HVD.

9. The RNA replicon of claim 1, wherein the alphavirus nsP3 HVD comprises a portion derived from:
   a. the New World alphavirus VEEV nsP3 HVD, but does not comprise amino acids 478-518 of the VEEV nsP3 HVD;
   b. the New World alphavirus VEEV nsP3 HVD, but does not comprise amino acids 478-545 of the VEEV nsP3 HVD;
   c. the New World alphavirus VEEV nsP3 HVD, but does not comprise amino acids 335-518 of the VEEV nsP3 HVD;
   d. the New World alphavirus VEEV nsP3 HVD, but does not comprise amino acids 335-538 of the VEEV nsP3 HVD;
   e. the New World alphavirus EEEV nsP3 HVD, but does not comprise amino acids 531-547 of the EEEV nsP3 HVD; or
   f. the New World alphavirus WEEV nsP3 HVD, but does not comprise amino acids 504-520 of the WEEV nsP3 HVD.

10. The RNA replicon of claim 9, wherein
   a. the New World alphavirus is EEEV, and the alphavirus nsP3 HVD comprises a portion derived from the New World alphavirus nsP3 HVD not comprising amino acids 531-547 of the EEEV nsP3 HVD, and comprises a portion derived from the Old World alphavirus nsP3 HVD comprising amino acids 479-500 of CHIKV nsP3 HVD, amino acids 451-471 of SFV nsP3 HVD, or amino acids 490-516 of SINV nsP3 HVD;
   b. the New World alphavirus is WEEV, and the alphavirus nsP3 HVD comprises a portion derived from the New World alphavirus nsP3 HVD not comprising amino acids 504-520 of the WEEV nsP3 HVD, and comprises a portion derived from the Old World alphavirus nsP3 HVD comprising amino acids 479-500 of CHIKV nsP3 HVD, amino acids 451-471 of SFV nsP3 HVD, or amino acids 490-516 of SINV nsP3 HVD; or
   c. the New World alphavirus is VEEV, and the alphavirus nsP3 HVD comprises a portion derived from the New World alphavirus nsP3 HVD not comprising amino acids 335-518 of the VEEV nsP3 HVD, and comprises a portion derived from the Old World alphavirus nsP3 HVD comprising amino acids 490-493, 513-516, 490-516, or 335-538 of SINV nsP3 HVD.

11. The RNA replicon of claim 1, further comprising a sub-genomic promoter that is operably linked to and regulates translation of the RNA sequence encoding the heterologous protein.

12. The RNA replicon of claim 1, further comprising a 5' cap and a 3' poly-A tail.

13. The RNA replicon of claim 1, wherein the replicon comprises positive sense, single-stranded RNA.

14. The RNA replicon of claim 1, wherein the replicon comprises 9-11 kb of RNA and has a diameter of 30-50 nm.

15. The RNA replicon of claim 1, wherein the heterologous protein is
   a. a biotherapeutic protein or peptide; or
   b. an antibody.

16. An RNA replicon comprising
   (i) an RNA sequence encoding a heterologous protein or peptide;
   (ii) RNA sequences encoding amino acid sequences derived from New World alphavirus nonstructural proteins nsP1, nsP2, and nsP4; and
   (iii) an RNA sequence encoding an amino acid sequence derived from an Old World alphavirus nsP3 protein, wherein the first 1-6 amino acids on the N-terminal and/or C-terminal side of the nsP3 protein are derived from a New World alphavirus sequence;
   wherein the replicon does not encode at least protein C.

17. A method of administering a heterologous protein or peptide to a mammal comprising administering to the mammal a pharmaceutical composition comprising the RNA replicon of claim 1, wherein the heterologous protein or peptide is expressed within the mammal.

18. An alphavirus replicon RNA, comprising: in order from 5' to 3' end,
   (i) an alphavirus 5' untranslated sequence for directing replication of the alphavirus replicon;
   (ii) an RNA sequence encoding alphaviral nonstructural proteins nsP1, nsP2, nsP3, and nsP4;
   (iii) an alphavirus subgenomic promoter sequence;
   (iv) an RNA sequence encoding one or more heterologous proteins or peptides; and
   (v) an alphavirus 3' untranslated sequence;
wherein the nsP1, nsP2 and nsP4 are from one or more New World alphaviruses, wherein the nsP3 comprises, in order from amino-terminus to carboxyl terminus: an alphavirus nsP3 macro domain, an alphavirus nsP3 central domain, and an alphavirus nsP3 hypervariable domain (HVD),
wherein the macro domain and the central domain are from one or more New World alphaviruses and/or Old World alphaviruses,
wherein the HVD comprises at least a portion of an Old World alphavirus HVD comprising a repeat selected from the group consisting of: an FGDF/FGDF (SEQ ID NO: 20) repeat, an FGSF/FGSF (SEQ ID NO: 21) repeat, an FGDF/FGSF (SEQ ID NO: 22) repeat, and an FGSF/FGDF (SEQ ID NO: 23) repeat; and further wherein the repeat sequences are separated by at least 10 but not more than 25 amino acids; wherein the HVD comprises the Old World alphavirus HVD comprising said portion of the Old World alphavirus HVD, or the HVD comprises a portion of an HVD from a New World alphavirus and said portion of an HVD from the Old World alphavirus;

wherein the New World alphavirus is selected from the group consisting of: a Venezuelan equine encephalitis virus (VEEV), a western equine encephalitis virus (WEEV), and an eastern equine encephalitis virus (EEEV); and the Old World alphavirus is selected from the group consisting of: Sindbis virus (SINV), Chickungunya virus (CHIKV), Semliki Forest Virus (SFV), Ross River Virus (RRV), Sagiyama virus (SAGV), Getah virus (GETV), Middleburg virus (MIDV), Bebaru virus (BEBV), O'nyong nyong virus (ONNV), Ndumu (NDUV), and Barmah Forest virus (BFV); and wherein the replicon does not encode at least protein C.

19. The alphavirus replicon RNA of claim 18, wherein the nsP1, nsP2, nsP4, nsP3 macro domain, and nsP3 central domain are from VEEV, and the nsP3 HVD comprises a portion of an HVD from VEEV and a portion of an HVD from an Old World alphavirus selected from the group consisting of SINV, CHIKV and SFV.

20. The RNA replicon of claim 19, wherein the heterologous protein is a biotherapeutic protein or peptide.

* * * * *

SEQUENCE LISTING

```
<160> NUMBER OF SEQ ID NOS: 31

<210> SEQ ID NO 1
<211> LENGTH: 2492
<212> TYPE: PRT
<213> ORGANISM: Venezuelan equine encephalitis virus

<400> SEQUENCE: 1

Met Glu Lys Val His Val Asp Ile Glu Glu Asp Ser Pro Phe Leu Arg
1               5                   10                  15

Ala Leu Gln Arg Ser Phe Pro Gln Phe Glu Val Glu Ala Lys Gln Val
            20                  25                  30

Thr Asp Asn Asp His Ala Asn Ala Arg Ala Phe Ser His Leu Ala Ser
        35                  40                  45

Lys Leu Ile Glu Thr Glu Val Asp Pro Ser Asp Thr Ile Leu Asp Ile
    50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Asp Glu Ser Cys Arg Tyr Glu
    130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
            180                 185                 190

Pro Ser Tyr Ser Thr Asn Trp Ala Asp Glu Thr Val Leu Thr Ala Arg
```

```
            195                 200                 205
Asn Ile Gly Leu Cys Ser Ser Asp Val Met Glu Arg Ser Arg Gly
            210                 215                 220
Met Ser Ile Leu Arg Lys Lys Tyr Leu Lys Pro Ser Asn Asn Val Leu
225                 230                 235                 240
Phe Ser Val Gly Ser Thr Ile Tyr His Glu Lys Arg Asp Leu Leu Arg
                245                 250                 255
Ser Trp His Leu Pro Ser Val Phe His Leu Arg Gly Lys Gln Asn Tyr
            260                 265                 270
Thr Cys Arg Cys Glu Thr Ile Val Ser Cys Asp Gly Tyr Val Val Lys
            275                 280                 285
Arg Ile Ala Ile Ser Pro Gly Leu Tyr Gly Lys Pro Ser Gly Tyr Ala
290                 295                 300
Ala Thr Met His Arg Glu Gly Phe Leu Cys Cys Lys Val Thr Asp Thr
305                 310                 315                 320
Leu Asn Gly Glu Arg Val Ser Phe Pro Val Cys Thr Tyr Val Pro Ala
                325                 330                 335
Thr Leu Cys Asp Gln Met Thr Gly Ile Leu Ala Thr Asp Val Ser Ala
                340                 345                 350
Asp Asp Ala Gln Lys Leu Leu Val Gly Leu Asn Gln Arg Ile Val Val
            355                 360                 365
Asn Gly Arg Thr Gln Arg Asn Thr Asn Thr Met Lys Asn Tyr Leu Leu
            370                 375                 380
Pro Val Val Ala Gln Ala Phe Ala Arg Trp Ala Lys Glu Tyr Lys Glu
385                 390                 395                 400
Asp Gln Glu Asp Glu Arg Pro Leu Gly Leu Arg Asp Arg Gln Leu Val
                405                 410                 415
Met Gly Cys Cys Trp Ala Phe Arg Arg His Lys Ile Thr Ser Ile Tyr
                420                 425                 430
Lys Arg Pro Asp Thr Gln Thr Ile Ile Lys Val Asn Ser Asp Phe His
            435                 440                 445
Ser Phe Val Leu Pro Arg Ile Gly Ser Asn Thr Leu Glu Ile Gly Leu
            450                 455                 460
Arg Thr Arg Ile Arg Lys Met Leu Glu Glu His Lys Glu Pro Ser Pro
465                 470                 475                 480
Leu Ile Thr Ala Glu Asp Val Gln Glu Ala Lys Cys Ala Ala Asp Glu
                485                 490                 495
Ala Lys Glu Val Arg Glu Ala Glu Glu Leu Arg Ala Ala Leu Pro Pro
            500                 505                 510
Leu Ala Ala Asp Val Glu Glu Pro Thr Leu Glu Ala Asp Val Asp Leu
            515                 520                 525
Met Leu Gln Glu Ala Gly Ala Gly Ser Val Glu Thr Pro Arg Gly Leu
            530                 535                 540
Ile Lys Val Thr Ser Tyr Ala Gly Glu Asp Lys Ile Gly Ser Tyr Ala
545                 550                 555                 560
Val Leu Ser Pro Gln Ala Val Leu Lys Ser Glu Lys Leu Ser Cys Ile
                565                 570                 575
His Pro Leu Ala Glu Gln Val Ile Val Ile Thr His Ser Gly Arg Lys
            580                 585                 590
Gly Arg Tyr Ala Val Glu Pro Tyr His Gly Lys Val Val Pro Glu
            595                 600                 605
Gly His Ala Ile Pro Val Gln Asp Phe Gln Ala Leu Ser Glu Ser Ala
            610                 615                 620
```

-continued

```
Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Tyr Tyr Lys
        645                 650                 655

Thr Val Lys Pro Ser Glu His Asp Gly Glu Tyr Leu Tyr Asp Ile Asp
            660                 665                 670

Arg Lys Gln Cys Val Lys Glu Leu Val Thr Gly Leu Gly Leu Thr
        675                 680                 685

Gly Glu Leu Val Asp Pro Pro Phe His Glu Phe Ala Tyr Glu Ser Leu
690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
            725                 730                 735

Lys Lys Asp Leu Val Val Ser Ala Lys Lys Glu Asn Cys Ala Glu Ile
        740                 745                 750

Ile Arg Asp Val Lys Lys Met Lys Gly Leu Asp Val Asn Ala Arg Thr
        755                 760                 765

Val Asp Ser Val Leu Leu Asn Gly Cys Lys His Pro Val Glu Thr Leu
770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
            805                 810                 815

Gln Cys Gly Phe Phe Asn Met Met Cys Leu Lys Val His Phe Asn His
            820                 825                 830

Glu Ile Cys Thr Gln Val Phe His Lys Ser Ile Ser Arg Arg Cys Thr
        835                 840                 845

Lys Ser Val Thr Ser Val Ser Thr Leu Phe Tyr Asp Lys Lys Met
850                 855                 860

Arg Thr Thr Asn Pro Lys Glu Thr Lys Ile Val Ile Asp Thr Thr Gly
865                 870                 875                 880

Ser Thr Lys Pro Lys Gln Asp Asp Leu Ile Leu Thr Cys Phe Arg Gly
            885                 890                 895

Trp Val Lys Gln Leu Gln Ile Asp Tyr Lys Gly Asn Glu Ile Met Thr
        900                 905                 910

Ala Ala Ala Ser Gln Gly Leu Thr Arg Lys Gly Val Tyr Ala Val Arg
        915                 920                 925

Tyr Lys Val Asn Glu Asn Pro Leu Tyr Ala Pro Thr Ser Glu His Val
        930                 935                 940

Asn Val Leu Leu Thr Arg Thr Glu Asp Arg Ile Val Trp Lys Thr Leu
945                 950                 955                 960

Ala Gly Asp Pro Trp Ile Lys Thr Leu Thr Ala Lys Tyr Pro Gly Asn
            965                 970                 975

Phe Thr Ala Thr Ile Glu Glu Trp Gln Ala Glu His Asp Ala Ile Met
        980                 985                 990

Arg His Ile Leu Glu Arg Pro Asp Pro Thr Asp Val Phe Gln Asn Lys
        995                 1000                1005

Ala Asn Val Cys Trp Ala Lys Ala Leu Val Pro Val Leu Lys Thr
    1010                1015                1020

Ala Gly Ile Asp Met Thr Thr Glu Gln Trp Asn Thr Val Asp Tyr
    1025                1030                1035
```

```
Phe Glu Thr Asp Lys Ala His Ser Ala Glu Ile Val Leu Asn Gln
    1040            1045                1050

Leu Cys Val Arg Phe Gly Leu Asp Leu Asp Ser Gly Leu Phe
    1055            1060                1065

Ser Ala Pro Thr Val Pro Leu Ser Ile Arg Asn Asn His Trp Asp
    1070            1075                1080

Asn Ser Pro Ser Pro Asn Met Tyr Gly Leu Asn Lys Glu Val Val
    1085            1090                1095

Arg Gln Leu Ser Arg Arg Tyr Pro Gln Leu Pro Arg Ala Val Ala
    1100            1105                1110

Thr Gly Arg Val Tyr Asp Met Asn Thr Gly Thr Leu Arg Asn Tyr
    1115            1120                1125

Asp Pro Arg Ile Asn Leu Val Pro Val Asn Arg Arg Leu Pro His
    1130            1135                1140

Ala Leu Val Leu His His Asn Glu His Pro Gln Ser Asp Phe Ser
    1145            1150                1155

Ser Phe Val Ser Lys Leu Lys Gly Arg Thr Val Leu Val Val Gly
    1160            1165                1170

Glu Lys Leu Ser Val Pro Gly Lys Met Val Asp Trp Leu Ser Asp
    1175            1180                1185

Arg Pro Glu Ala Thr Phe Arg Ala Arg Leu Asp Leu Gly Ile Pro
    1190            1195                1200

Gly Asp Val Pro Lys Tyr Asp Ile Ile Phe Val Asn Val Arg Thr
    1205            1210                1215

Pro Tyr Lys Tyr His His Tyr Gln Gln Cys Glu Asp His Ala Ile
    1220            1225                1230

Lys Leu Ser Met Leu Thr Lys Lys Ala Cys Leu His Leu Asn Pro
    1235            1240                1245

Gly Gly Thr Cys Val Ser Ile Gly Tyr Gly Tyr Ala Asp Arg Ala
    1250            1255                1260

Ser Glu Ser Ile Ile Gly Ala Ile Ala Arg Gln Phe Lys Phe Ser
    1265            1270                1275

Arg Val Cys Lys Pro Lys Ser Ser Leu Glu Glu Thr Glu Val Leu
    1280            1285                1290

Phe Val Phe Ile Gly Tyr Asp Arg Lys Ala Arg Thr His Asn Pro
    1295            1300                1305

Tyr Lys Leu Ser Ser Thr Leu Thr Asn Ile Tyr Thr Gly Ser Arg
    1310            1315                1320

Leu His Glu Ala Gly Cys Ala Pro Ser Tyr His Val Val Arg Gly
    1325            1330                1335

Asp Ile Ala Thr Ala Thr Glu Gly Val Ile Ile Asn Ala Ala Asn
    1340            1345                1350

Ser Lys Gly Gln Pro Gly Gly Gly Val Cys Gly Ala Leu Tyr Lys
    1355            1360                1365

Lys Phe Pro Glu Ser Phe Asp Leu Gln Pro Ile Glu Val Gly Lys
    1370            1375                1380

Ala Arg Leu Val Lys Gly Ala Ala Lys His Ile Ile His Ala Val
    1385            1390                1395

Gly Pro Asn Phe Asn Lys Val Ser Glu Val Glu Gly Asp Lys Gln
    1400            1405                1410

Leu Ala Glu Ala Tyr Glu Ser Ile Ala Lys Ile Val Asn Asp Asn
    1415            1420                1425

Asn Tyr Lys Ser Val Ala Ile Pro Leu Leu Ser Thr Gly Ile Phe
```

```
                1430                1435                1440
Ser Gly Asn Lys Asp Arg Leu Thr Gln Ser Leu Asn His Leu Leu
                1445                1450                1455
Thr Ala Leu Asp Thr Thr Asp Ala Asp Val Ala Ile Tyr Cys Arg
                1460                1465                1470
Asp Lys Lys Trp Glu Met Thr Leu Lys Glu Ala Val Ala Arg Arg
                1475                1480                1485
Glu Ala Val Glu Glu Ile Cys Ile Ser Asp Asp Ser Ser Val Thr
                1490                1495                1500
Glu Pro Asp Ala Glu Leu Val Arg Val His Pro Lys Ser Ser Leu
                1505                1510                1515
Ala Gly Arg Lys Gly Tyr Ser Thr Ser Asp Gly Lys Thr Phe Ser
                1520                1525                1530
Tyr Leu Glu Gly Thr Lys Phe His Gln Ala Ala Lys Asp Ile Ala
                1535                1540                1545
Glu Ile Asn Ala Met Trp Pro Val Ala Thr Glu Ala Asn Glu Gln
                1550                1555                1560
Val Cys Met Tyr Ile Leu Gly Glu Ser Met Ser Ser Ile Arg Ser
                1565                1570                1575
Lys Cys Pro Val Glu Glu Ser Glu Ala Ser Thr Pro Pro Ser Thr
                1580                1585                1590
Leu Pro Cys Leu Cys Ile His Ala Met Thr Pro Glu Arg Val Gln
                1595                1600                1605
Arg Leu Lys Ala Ser Arg Pro Glu Gln Ile Thr Val Cys Ser Ser
                1610                1615                1620
Phe Pro Leu Pro Lys Tyr Arg Ile Thr Gly Val Gln Lys Ile Gln
                1625                1630                1635
Cys Ser Gln Pro Ile Leu Phe Ser Pro Lys Val Pro Ala Tyr Ile
                1640                1645                1650
His Pro Arg Lys Tyr Leu Val Glu Thr Pro Pro Val Asp Glu Thr
                1655                1660                1665
Pro Glu Pro Ser Ala Glu Asn Gln Ser Thr Glu Gly Thr Pro Glu
                1670                1675                1680
Gln Pro Pro Leu Ile Thr Glu Asp Glu Thr Arg Thr Arg Thr Pro
                1685                1690                1695
Glu Pro Ile Ile Ile Glu Glu Glu Glu Asp Ser Ile Ser Leu
                1700                1705                1710
Leu Ser Asp Gly Pro Thr His Gln Val Leu Gln Val Glu Ala Asp
                1715                1720                1725
Ile His Gly Pro Pro Ser Val Ser Ser Ser Ser Trp Ser Ile Pro
                1730                1735                1740
His Ala Ser Asp Phe Asp Val Asp Ser Leu Ser Ile Leu Asp Thr
                1745                1750                1755
Leu Glu Gly Ala Ser Val Thr Ser Gly Ala Thr Ser Ala Glu Thr
                1760                1765                1770
Asn Ser Tyr Phe Ala Lys Ser Met Glu Phe Leu Ala Arg Pro Val
                1775                1780                1785
Pro Ala Pro Arg Thr Val Phe Arg Asn Pro Pro His Pro Ala Pro
                1790                1795                1800
Arg Thr Arg Thr Pro Ser Leu Ala Pro Ser Arg Ala Cys Ser Arg
                1805                1810                1815
Thr Ser Leu Val Ser Thr Pro Pro Gly Val Asn Arg Val Ile Thr
                1820                1825                1830
```

```
Arg Glu Glu Leu Glu Ala Leu Thr Pro Ser Arg Thr Pro Ser Arg
    1835                1840                1845

Ser Val Ser Arg Thr Ser Leu Val Ser Asn Pro Pro Gly Val Asn
    1850                1855                1860

Arg Val Ile Thr Arg Glu Glu Phe Glu Ala Phe Val Ala Gln Gln
    1865                1870                1875

Gln Arg Phe Asp Ala Gly Ala Tyr Ile Phe Ser Ser Asp Thr Gly
    1880                1885                1890

Gln Gly His Leu Gln Gln Lys Ser Val Arg Gln Thr Val Leu Ser
    1895                1900                1905

Glu Val Val Leu Glu Arg Thr Glu Leu Glu Ile Ser Tyr Ala Pro
    1910                1915                1920

Arg Leu Asp Gln Glu Lys Glu Leu Leu Arg Lys Lys Leu Gln
    1925                1930                1935

Leu Asn Pro Thr Pro Ala Asn Arg Ser Arg Tyr Gln Ser Arg Lys
    1940                1945                1950

Val Glu Asn Met Lys Ala Ile Thr Ala Arg Arg Ile Leu Gln Gly
    1955                1960                1965

Leu Gly His Tyr Leu Lys Ala Glu Gly Lys Val Glu Cys Tyr Arg
    1970                1975                1980

Thr Leu His Pro Val Pro Leu Tyr Ser Ser Ser Val Asn Arg Ala
    1985                1990                1995

Phe Ser Ser Pro Lys Val Ala Val Glu Ala Cys Asn Ala Met Leu
    2000                2005                2010

Lys Glu Asn Phe Pro Thr Val Ala Ser Tyr Cys Ile Ile Pro Glu
    2015                2020                2025

Tyr Asp Ala Tyr Leu Asp Met Val Asp Gly Ala Ser Cys Cys Leu
    2030                2035                2040

Asp Thr Ala Ser Phe Cys Pro Ala Lys Leu Arg Ser Phe Pro Lys
    2045                2050                2055

Lys His Ser Tyr Leu Glu Pro Thr Ile Arg Ser Ala Val Pro Ser
    2060                2065                2070

Ala Ile Gln Asn Thr Leu Gln Asn Val Leu Ala Ala Ala Thr Lys
    2075                2080                2085

Arg Asn Cys Asn Val Thr Gln Met Arg Glu Leu Pro Val Leu Asp
    2090                2095                2100

Ser Ala Ala Phe Asn Val Glu Cys Phe Lys Lys Tyr Ala Cys Asn
    2105                2110                2115

Asn Glu Tyr Trp Glu Thr Phe Lys Glu Asn Pro Ile Arg Leu Thr
    2120                2125                2130

Glu Glu Asn Val Val Asn Tyr Ile Thr Lys Leu Lys Gly Pro Lys
    2135                2140                2145

Ala Ala Ala Leu Phe Ala Lys Thr His Asn Leu Asn Met Leu Gln
    2150                2155                2160

Asp Ile Pro Met Asp Arg Phe Val Met Asp Leu Lys Arg Asp Val
    2165                2170                2175

Lys Val Thr Pro Gly Thr Lys His Thr Glu Glu Arg Pro Lys Val
    2180                2185                2190

Gln Val Ile Gln Ala Ala Asp Pro Leu Ala Thr Ala Tyr Leu Cys
    2195                2200                2205

Gly Ile His Arg Glu Leu Val Arg Arg Leu Asn Ala Val Leu Leu
    2210                2215                2220
```

```
Pro Asn Ile His Thr Leu Phe Asp Met Ser Ala Glu Asp Phe Asp
    2225                2230                2235

Ala Ile Ile Ala Glu His Phe Gln Pro Gly Asp Cys Val Leu Glu
    2240                2245                2250

Thr Asp Ile Ala Ser Phe Asp Lys Ser Glu Asp Ala Met Ala
    2255                2260                2265

Leu Thr Ala Leu Met Ile Leu Glu Asp Leu Gly Val Asp Ala Glu
    2270                2275                2280

Leu Leu Thr Leu Ile Glu Ala Ala Phe Gly Glu Ile Ser Ser Ile
    2285                2290                2295

His Leu Pro Thr Lys Thr Lys Phe Lys Phe Gly Ala Met Met Lys
    2300                2305                2310

Ser Gly Met Phe Leu Thr Leu Phe Val Asn Thr Val Ile Asn Ile
    2315                2320                2325

Val Ile Ala Ser Arg Val Leu Arg Glu Arg Leu Thr Gly Ser Pro
    2330                2335                2340

Cys Ala Ala Phe Ile Gly Asp Asp Asn Ile Val Lys Gly Val Lys
    2345                2350                2355

Ser Asp Lys Leu Met Ala Asp Arg Cys Ala Thr Trp Leu Asn Met
    2360                2365                2370

Glu Val Lys Ile Ile Asp Ala Val Val Gly Glu Lys Ala Pro Tyr
    2375                2380                2385

Phe Cys Gly Gly Phe Ile Leu Cys Asp Ser Val Thr Gly Thr Ala
    2390                2395                2400

Cys Arg Val Ala Asp Pro Leu Lys Arg Leu Phe Lys Leu Gly Lys
    2405                2410                2415

Pro Leu Ala Ala Asp Asp Glu His Asp Asp Asp Arg Arg Arg Ala
    2420                2425                2430

Leu His Glu Glu Ser Thr Arg Trp Asn Arg Val Gly Ile Leu Ser
    2435                2440                2445

Glu Leu Cys Lys Ala Val Glu Ser Arg Tyr Glu Thr Val Gly Thr
    2450                2455                2460

Ser Ile Ile Val Met Ala Met Thr Thr Leu Ala Ser Ser Val Lys
    2465                2470                2475

Ser Phe Ser Tyr Leu Arg Gly Ala Pro Ile Thr Leu Tyr Gly
    2480                2485                2490

<210> SEQ ID NO 2
<211> LENGTH: 2493
<212> TYPE: PRT
<213> ORGANISM: Eastern equine encephalomyelitis virus

<400> SEQUENCE: 2

Met Glu Lys Val His Val Asp Leu Asp Ala Asp Ser Pro Phe Val Lys
1               5                   10                  15

Ser Leu Gln Arg Cys Phe Pro His Phe Glu Ile Glu Ala Thr Gln Val
                20                  25                  30

Thr Asp Asn Asp His Ala Asn Ala Arg Ala Phe Ser His Leu Ala Thr
            35                  40                  45

Lys Leu Ile Glu Gly Gly Val Asp Thr Asp Gln Val Ile Leu Asp Ile
        50                  55                  60

Gly Ser Ala Pro Val Arg His Thr His Ser Lys His Lys Tyr His Cys
65                  70                  75                  80

Ile Cys Pro Met Lys Ser Ala Glu Asp Pro Asp Arg Leu Tyr Arg Tyr
                85                  90                  95
```

```
Ala Asp Lys Leu Arg Lys Ser Asp Val Thr Asp Lys Cys Ile Ala Ser
            100                 105                 110

Lys Ala Ala Asp Leu Leu Thr Val Met Ser Thr Pro Asp Ala Glu Thr
            115                 120                 125

Pro Ser Leu Cys Met His Thr Asp Ser Thr Cys Arg Tyr His Gly Ser
            130                 135                 140

Val Ala Val Tyr Gln Asp Val Tyr Ala Val His Ala Pro Thr Ser Ile
145                 150                 155                 160

Tyr Tyr Gln Ala Leu Lys Gly Val Arg Thr Ile Tyr Trp Ile Gly Phe
                165                 170                 175

Asp Thr Thr Pro Phe Met Tyr Lys Asn Met Ala Gly Ala Tyr Pro Thr
            180                 185                 190

Tyr Asn Thr Asn Trp Ala Asp Glu Ser Val Leu Glu Ala Arg Asn Ile
            195                 200                 205

Gly Leu Gly Ser Ser Asp Leu His Glu Lys Ser Phe Gly Lys Val Ser
            210                 215                 220

Ile Met Arg Lys Lys Lys Leu Gln Pro Thr Asn Lys Val Ile Phe Ser
225                 230                 235                 240

Val Gly Ser Thr Ile Tyr Thr Glu Glu Arg Ile Leu Leu Arg Ser Trp
                245                 250                 255

His Leu Pro Asn Val Phe His Leu Lys Gly Lys Thr Ser Phe Thr Gly
            260                 265                 270

Arg Cys Asn Thr Ile Val Ser Cys Glu Gly Tyr Val Lys Lys Ile
            275                 280                 285

Thr Leu Ser Pro Gly Ile Tyr Gly Lys Val Asp Asn Leu Ala Ser Thr
            290                 295                 300

Met His Arg Glu Gly Phe Leu Ser Cys Lys Val Thr Asp Thr Leu Arg
305                 310                 315                 320

Gly Glu Arg Val Ser Phe Pro Val Cys Thr Tyr Val Pro Ala Thr Leu
                325                 330                 335

Cys Asp Gln Met Thr Gly Ile Leu Ala Thr Asp Val Ser Val Asp Asp
            340                 345                 350

Ala Gln Lys Leu Leu Val Gly Leu Asn Gln Arg Ile Val Val Asn Gly
            355                 360                 365

Arg Thr Gln Arg Asn Thr Asn Thr Met Gln Asn Tyr Leu Leu Pro Val
            370                 375                 380

Val Ala Gln Ala Phe Ser Arg Trp Ala Arg Glu His Arg Ala Asp Leu
385                 390                 395                 400

Glu Asp Glu Lys Gly Leu Gly Val Arg Glu Arg Ser Leu Val Met Gly
                405                 410                 415

Cys Cys Trp Ala Phe Lys Thr His Lys Ile Thr Ser Ile Tyr Lys Arg
            420                 425                 430

Pro Gly Thr Gln Thr Ile Lys Lys Val Pro Ala Val Phe Asn Ser Phe
            435                 440                 445

Val Ile Pro Gln Pro Thr Ser Tyr Gly Leu Asp Ile Gly Leu Arg Arg
450                 455                 460

Arg Ile Lys Met Leu Phe Asp Ala Lys Lys Ala Pro Ala Pro Ile Ile
465                 470                 475                 480

Thr Glu Ala Asp Val Ala His Leu Lys Gly Leu Gln Asp Glu Ala Glu
                485                 490                 495

Ala Val Ala Glu Ala Glu Ala Val Arg Ala Ala Leu Pro Pro Leu Leu
            500                 505                 510
```

-continued

```
Pro Glu Val Asp Lys Glu Thr Val Glu Ala Asp Ile Asp Leu Ile Met
            515                 520                 525
Gln Glu Ala Gly Ala Gly Ser Val Glu Thr Pro Arg Arg His Ile Lys
530                 535                 540
Val Thr Thr Tyr Pro Gly Glu Glu Met Ile Gly Ser Tyr Ala Val Leu
545                 550                 555                 560
Ser Pro Gln Ala Val Leu Asn Ser Glu Lys Leu Ala Cys Ile His Pro
                565                 570                 575
Leu Ala Glu Gln Val Leu Val Met Thr His Lys Gly Arg Ala Gly Arg
            580                 585                 590
Tyr Lys Val Glu Pro Tyr His Gly Arg Val Ile Val Pro Ser Gly Thr
        595                 600                 605
Ala Ile Pro Ile Leu Asp Phe Gln Ala Leu Ser Glu Ser Ala Thr Ile
    610                 615                 620
Val Phe Asn Glu Arg Glu Phe Val Asn Arg Tyr Leu His His Ile Ala
625                 630                 635                 640
Val Asn Gly Gly Ala Leu Asn Thr Asp Glu Glu Tyr Tyr Lys Val Val
                645                 650                 655
Lys Ser Thr Glu Thr Asp Ser Glu Tyr Val Phe Asp Ile Asp Ala Lys
            660                 665                 670
Lys Cys Val Lys Lys Gly Asp Ala Gly Pro Met Cys Leu Val Gly Glu
        675                 680                 685
Leu Val Asp Pro Pro Phe His Glu Phe Ala Tyr Glu Ser Leu Lys Thr
    690                 695                 700
Arg Pro Ala Ala Pro His Lys Val Pro Thr Ile Gly Val Tyr Gly Val
705                 710                 715                 720
Pro Gly Ser Gly Lys Ser Gly Ile Ile Lys Ser Ala Val Thr Lys Arg
                725                 730                 735
Asp Leu Val Val Ser Ala Lys Lys Glu Asn Cys Met Glu Ile Ile Lys
            740                 745                 750
Asp Val Lys Arg Met Arg Gly Met Asp Ile Ala Ala Arg Thr Val Asp
        755                 760                 765
Ser Val Leu Leu Asn Gly Val Lys His Ser Val Asp Thr Leu Tyr Ile
    770                 775                 780
Asp Glu Ala Phe Ala Cys His Ala Gly Thr Leu Leu Ala Leu Ile Ala
785                 790                 795                 800
Ile Val Lys Pro Lys Lys Val Val Leu Cys Gly Asp Pro Lys Gln Cys
                805                 810                 815
Gly Phe Phe Asn Met Met Cys Leu Lys Val His Phe Asn His Glu Ile
            820                 825                 830
Cys Thr Glu Val Tyr His Lys Ser Ile Ser Arg Arg Cys Thr Lys Thr
        835                 840                 845
Val Thr Ser Ile Val Ser Thr Leu Phe Tyr Asp Lys Arg Met Arg Thr
    850                 855                 860
Val Asn Pro Cys Asn Asp Lys Ile Ile Ile Asp Thr Thr Ser Thr Thr
865                 870                 875                 880
Lys Pro Leu Lys Asp Asp Ile Ile Leu Thr Cys Phe Arg Gly Trp Val
                885                 890                 895
Lys Gln Leu Gln Ile Asp Tyr Lys Asn His Glu Ile Met Thr Ala Ala
            900                 905                 910
Ala Ser Gln Gly Leu Thr Arg Lys Gly Val Tyr Ala Val Arg Tyr Lys
        915                 920                 925
Val Asn Glu Asn Pro Leu Tyr Ala Gln Thr Ser Glu His Val Asn Val
```

```
                930             935             940
Leu Leu Thr Arg Thr Glu Lys Arg Ile Val Trp Lys Thr Leu Ala Gly
945                 950             955                 960

Asp Pro Trp Ile Lys Thr Leu Thr Ala Ser Tyr Pro Gly Asn Phe Thr
                965             970             975

Ala Thr Leu Glu Glu Trp Gln Ala Glu His Asp Ala Ile Met Ala Lys
                980             985             990

Ile Leu Glu Thr Pro Ala Ser Ser Asp Val Phe Gln Asn Lys Val Asn
        995             1000            1005

Val Cys Trp Ala Lys Ala Leu Glu Pro Val Leu Ala Thr Ala Asn
    1010            1015            1020

Ile Thr Leu Thr Arg Ser Gln Trp Glu Thr Ile Pro Ala Phe Lys
    1025            1030            1035

Asp Asp Lys Ala Tyr Ser Pro Glu Met Ala Leu Asn Phe Phe Cys
    1040            1045            1050

Thr Arg Phe Phe Gly Val Asp Ile Asp Ser Gly Leu Phe Ser Ala
    1055            1060            1065

Pro Thr Val Pro Leu Thr Tyr Thr Asn Glu His Trp Asp Asn Ser
    1070            1075            1080

Pro Gly Pro Asn Met Tyr Gly Leu Cys Met Arg Thr Ala Lys Glu
    1085            1090            1095

Leu Ala Arg Arg Tyr Pro Cys Ile Leu Lys Ala Val Asp Thr Gly
    1100            1105            1110

Arg Val Ala Asp Val Arg Thr Asp Thr Ile Lys Asp Tyr Asn Pro
    1115            1120            1125

Leu Ile Asn Val Val Pro Leu Asn Arg Arg Leu Pro His Ser Leu
    1130            1135            1140

Val Val Thr His Arg Tyr Thr Gly Asn Gly Asp Tyr Ser Gln Leu
    1145            1150            1155

Val Thr Lys Met Thr Gly Lys Thr Val Leu Val Gly Thr Pro
    1160            1165            1170

Met Asn Ile Pro Gly Lys Arg Val Glu Thr Leu Gly Pro Ser Pro
    1175            1180            1185

Gln Cys Thr Tyr Lys Ala Glu Leu Asp Leu Gly Ile Pro Ala Ala
    1190            1195            1200

Leu Gly Lys Tyr Asp Ile Ile Phe Ile Asn Val Arg Thr Pro Tyr
    1205            1210            1215

Arg His His His Tyr Gln Gln Cys Glu Asp His Ala Ile His His
    1220            1225            1230

Ser Met Leu Thr Arg Lys Ala Val Asp His Leu Asn Lys Gly Gly
    1235            1240            1245

Thr Cys Ile Ala Leu Gly Tyr Gly Thr Ala Asp Arg Ala Thr Glu
    1250            1255            1260

Asn Ile Ile Ser Ala Val Ala Arg Ser Phe Arg Phe Ser Arg Val
    1265            1270            1275

Cys Gln Pro Lys Cys Ala Trp Glu Asn Thr Glu Val Ala Phe Val
    1280            1285            1290

Phe Phe Gly Lys Asp Asn Gly Asn His Leu Gln Asp Gln Asp Arg
    1295            1300            1305

Leu Ser Val Val Leu Asn Asn Ile Tyr Gln Gly Ser Thr Gln His
    1310            1315            1320

Glu Ala Gly Arg Ala Pro Ala Tyr Arg Val Val Arg Gly Asp Ile
    1325            1330            1335
```

```
Thr Lys Ser Asn Asp Glu Val Ile Val Asn Ala Ala Asn Asn Lys
    1340            1345            1350

Gly Gln Pro Gly Ser Gly Val Cys Gly Ala Leu Tyr Arg Lys Trp
    1355            1360            1365

Pro Gly Ala Phe Asp Lys Gln Pro Val Ala Thr Gly Lys Ala His
    1370            1375            1380

Leu Val Lys His Ser Pro Asn Val Ile His Ala Val Gly Pro Asn
    1385            1390            1395

Phe Ser Arg Leu Ser Glu Asn Glu Gly Asp Gln Lys Leu Ser Glu
    1400            1405            1410

Val Tyr Met Asp Ile Ala Arg Ile Ile Asn Asn Glu Arg Phe Thr
    1415            1420            1425

Lys Val Ser Ile Pro Leu Leu Ser Thr Gly Ile Tyr Ala Gly Gly
    1430            1435            1440

Lys Asp Arg Val Met Gln Ser Leu Asn His Leu Phe Thr Ala Met
    1445            1450            1455

Asp Thr Thr Asp Ala Asp Ile Thr Ile Tyr Cys Leu Asp Lys Gln
    1460            1465            1470

Trp Glu Ser Arg Ile Lys Glu Ala Ile Thr Arg Lys Glu Ser Val
    1475            1480            1485

Glu Glu Leu Thr Glu Asp Asp Arg Pro Val Asp Ile Glu Leu Val
    1490            1495            1500

Arg Val His Pro Leu Ser Ser Leu Ala Gly Arg Pro Gly Tyr Ser
    1505            1510            1515

Thr Thr Glu Gly Lys Val Tyr Ser Tyr Leu Glu Gly Thr Arg Phe
    1520            1525            1530

His Gln Thr Ala Lys Asp Ile Ala Glu Ile Tyr Ala Met Trp Pro
    1535            1540            1545

Asn Lys Gln Glu Ala Asn Glu Gln Ile Cys Leu Tyr Val Leu Gly
    1550            1555            1560

Glu Ser Met Asn Ser Ile Arg Ser Lys Cys Pro Val Glu Glu Ser
    1565            1570            1575

Glu Ala Ser Ser Pro Pro His Thr Ile Pro Cys Leu Cys Asn Tyr
    1580            1585            1590

Ala Met Thr Ala Glu Arg Val Tyr Arg Leu Arg Met Ala Lys Asn
    1595            1600            1605

Glu Gln Phe Ala Val Cys Ser Ser Phe Gln Leu Pro Lys Tyr Arg
    1610            1615            1620

Ile Thr Gly Val Gln Lys Ile Gln Cys Ser Lys Pro Val Ile Phe
    1625            1630            1635

Ser Gly Thr Val Pro Pro Ala Ile His Pro Arg Lys Phe Ala Ser
    1640            1645            1650

Val Thr Val Glu Asp Thr Pro Val Val Gln Pro Glu Arg Leu Val
    1655            1660            1665

Pro Arg Arg Pro Ala Pro Pro Val Pro Val Pro Ala Arg Ile Pro
    1670            1675            1680

Ser Pro Pro Cys Thr Ser Thr Asn Gly Ser Thr Thr Ser Ile Gln
    1685            1690            1695

Ser Leu Gly Glu Asp Gln Ser Ala Ser Ala Ser Ser Gly Ala Glu
    1700            1705            1710

Ile Ser Val Asp Gln Val Ser Leu Trp Ser Ile Pro Ser Ala Thr
    1715            1720            1725
```

```
Gly Phe Asp Val Arg Thr Ser Ser Leu Ser Leu Glu Gln Pro
1730            1735            1740

Thr Phe Pro Thr Met Val Val Glu Ala Glu Ile His Ala Ser Gln
1745            1750            1755

Gly Ser Leu Trp Ser Ile Pro Ser Ile Thr Gly Ser Glu Thr Arg
1760            1765            1770

Ala Pro Ser Pro Pro Ser Gln Asp Ser Arg Pro Ser Thr Pro Ser
1775            1780            1785

Ala Ser Gly Ser His Thr Ser Val Asp Leu Ile Thr Phe Asp Ser
1790            1795            1800

Val Ala Glu Ile Leu Glu Asp Phe Ser Arg Ser Pro Phe Gln Phe
1805            1810            1815

Leu Ser Glu Ile Lys Pro Ile Pro Ala Pro Arg Thr Arg Val Asn
1820            1825            1830

Asn Met Ser Arg Ser Ala Asp Thr Ile Lys Pro Ile Pro Lys Pro
1835            1840            1845

Arg Lys Cys Gln Val Lys Tyr Thr Gln Pro Pro Gly Val Ala Arg
1850            1855            1860

Val Ile Ser Ala Ala Glu Phe Asp Glu Phe Val Arg Arg His Ser
1865            1870            1875

Asn Arg Tyr Glu Ala Gly Ala Tyr Ile Phe Ser Ser Glu Thr Gly
1880            1885            1890

Gln Gly His Leu Gln Gln Lys Ser Thr Arg Gln Cys Lys Leu Gln
1895            1900            1905

Tyr Pro Ile Leu Glu Arg Ser Val His Glu Lys Phe Tyr Ala Pro
1910            1915            1920

Arg Leu Asp Leu Glu Arg Glu Lys Leu Leu Gln Lys Lys Leu Gln
1925            1930            1935

Leu Cys Ala Ser Glu Gly Asn Arg Ser Arg Tyr Gln Ser Arg Lys
1940            1945            1950

Val Glu Asn Met Lys Ala Ile Thr Val Glu Arg Leu Leu Gln Gly
1955            1960            1965

Ile Gly Ser Tyr Leu Ser Ala Glu Pro Gln Pro Val Glu Cys Tyr
1970            1975            1980

Lys Val Thr Tyr Pro Ala Pro Met Tyr Ser Ser Thr Ala Ser Asn
1985            1990            1995

Ser Phe Ser Ser Ala Glu Val Ala Val Lys Val Cys Asn Leu Val
2000            2005            2010

Leu Gln Glu Asn Phe Pro Thr Val Ala Ser Tyr Asn Ile Thr Asp
2015            2020            2025

Glu Tyr Asp Ala Tyr Leu Asp Met Val Asp Gly Ala Ser Cys Cys
2030            2035            2040

Leu Asp Thr Ala Thr Phe Cys Pro Ala Lys Leu Arg Ser Phe Pro
2045            2050            2055

Lys Lys His Ser Tyr Leu Arg Pro Glu Ile Arg Ser Ala Val Pro
2060            2065            2070

Ser Pro Ile Gln Asn Thr Leu Gln Asn Val Leu Ala Ala Ala Thr
2075            2080            2085

Lys Arg Asn Cys Asn Val Thr Gln Met Arg Glu Leu Pro Val Leu
2090            2095            2100

Asp Ser Ala Ala Phe Asn Val Glu Cys Phe Lys Lys Tyr Ala Cys
2105            2110            2115

Asn Asp Glu Tyr Trp Asp Phe Tyr Lys Thr Asn Pro Ile Arg Leu
```

```
                2120                2125                 2130

Thr Ala Glu Asn Val Thr Gln Tyr Val Thr Lys Leu Lys Gly Pro
            2135                2140                 2145

Lys Ala Ala Ala Leu Phe Ala Lys Thr His Asn Leu Gln Pro Leu
            2150                2155                 2160

His Glu Ile Pro Met Asp Arg Phe Val Met Asp Leu Lys Arg Asp
            2165                2170                 2175

Val Lys Val Thr Pro Gly Thr Lys His Thr Glu Glu Arg Pro Lys
            2180                2185                 2190

Val Gln Val Ile Gln Ala Ala Asp Pro Leu Ala Thr Ala Tyr Leu
            2195                2200                 2205

Cys Gly Ile His Arg Glu Leu Val Arg Arg Leu Asn Ala Val Leu
            2210                2215                 2220

Leu Pro Asn Ile His Thr Leu Phe Asp Met Ser Ala Glu Asp Phe
            2225                2230                 2235

Asp Ala Ile Ile Ala Glu His Phe Gln Phe Gly Asp Ala Val Leu
            2240                2245                 2250

Glu Thr Asp Ile Ala Ser Phe Asp Lys Ser Glu Asp Asp Ala Ile
            2255                2260                 2265

Ala Met Ser Ala Leu Met Ile Leu Glu Asp Leu Gly Val Asp Gln
            2270                2275                 2280

Ala Leu Leu Asn Leu Ile Glu Ala Ala Phe Gly Asn Ile Thr Ser
            2285                2290                 2295

Val His Leu Pro Thr Gly Thr Arg Phe Lys Phe Gly Ala Met Met
            2300                2305                 2310

Lys Ser Gly Met Phe Leu Thr Leu Phe Ile Asn Thr Val Val Asn
            2315                2320                 2325

Ile Met Ile Ala Ser Arg Val Leu Arg Glu Arg Leu Thr Thr Ser
            2330                2335                 2340

Pro Cys Ala Ala Phe Ile Gly Asp Asp Asn Ile Val Lys Gly Val
            2345                2350                 2355

Thr Ser Asp Ala Leu Met Ala Glu Arg Cys Ala Thr Trp Leu Asn
            2360                2365                 2370

Met Glu Val Lys Ile Ile Asp Ala Val Val Gly Val Lys Ala Pro
            2375                2380                 2385

Tyr Phe Cys Gly Gly Phe Ile Val Val Asp Gln Ile Thr Gly Thr
            2390                2395                 2400

Ala Cys Arg Val Ala Asp Pro Leu Lys Arg Leu Phe Lys Leu Gly
            2405                2410                 2415

Lys Pro Leu Pro Leu Asp Asp Asp Gln Asp Val Asp Arg Arg Arg
            2420                2425                 2430

Ala Leu His Asp Glu Ala Ala Arg Trp Asn Arg Ile Gly Ile Thr
            2435                2440                 2445

Glu Glu Leu Val Lys Ala Val Glu Ser Arg Tyr Glu Val Asn Tyr
            2450                2455                 2460

Val Ser Leu Ile Ile Thr Ala Leu Thr Thr Leu Ala Ser Ser Val
            2465                2470                 2475

Ser Asn Phe Lys His Ile Arg Gly His Pro Ile Thr Leu Tyr Gly
            2480                2485                 2490

<210> SEQ ID NO 3
<211> LENGTH: 2431
<212> TYPE: PRT
<213> ORGANISM: Semliki Forest virus
```

```
<400> SEQUENCE: 3

Met Ala Ala Lys Val His Val Asp Ile Glu Ala Asp Ser Pro Phe Ile
1               5                   10                  15

Lys Ser Leu Gln Lys Ala Phe Pro Ser Phe Glu Val Glu Ser Leu Gln
            20                  25                  30

Val Thr Pro Asn Asp His Ala Asn Ala Arg Ala Phe Ser His Leu Ala
            35                  40                  45

Thr Lys Leu Ile Glu Gln Glu Thr Asp Lys Asp Thr Leu Ile Leu Asp
50                  55                  60

Ile Gly Ser Ala Pro Ser Arg Arg Met Met Ser Thr His Lys Tyr His
65                  70                  75                  80

Cys Val Cys Pro Met Arg Ser Ala Glu Asp Pro Glu Arg Leu Asp Ser
                85                  90                  95

Tyr Ala Lys Lys Leu Ala Ala Ala Ser Gly Lys Val Leu Asp Arg Glu
            100                 105                 110

Ile Ala Gly Lys Ile Thr Asp Leu Gln Thr Val Met Ala Thr Pro Asp
            115                 120                 125

Ala Glu Ser Pro Thr Phe Cys Leu His Thr Asp Val Thr Cys Arg Thr
145                 135                 140

Ala Ala Glu Val Ala Val Tyr Gln Asp Val Tyr Ala Val His Ala Pro
145                 150                 155                 160

Thr Ser Leu Tyr His Gln Ala Met Lys Gly Val Arg Thr Ala Tyr Trp
                165                 170                 175

Ile Gly Phe Asp Thr Thr Pro Phe Met Phe Asp Ala Leu Ala Gly Ala
            180                 185                 190

Tyr Pro Thr Tyr Ala Thr Asn Trp Ala Asp Glu Gln Val Leu Gln Ala
            195                 200                 205

Arg Asn Ile Gly Leu Cys Ala Ala Ser Leu Thr Glu Gly Arg Leu Gly
            210                 215                 220

Lys Leu Ser Ile Leu Arg Lys Lys Gln Leu Lys Pro Cys Asp Thr Val
225                 230                 235                 240

Met Phe Ser Val Gly Ser Thr Leu Tyr Thr Glu Ser Arg Lys Leu Leu
                245                 250                 255

Arg Ser Trp His Leu Pro Ser Val Phe His Leu Lys Gly Lys Gln Ser
                260                 265                 270

Phe Thr Cys Arg Cys Asp Thr Ile Val Ser Cys Glu Gly Tyr Val Val
            275                 280                 285

Lys Lys Ile Thr Met Cys Pro Gly Leu Tyr Gly Lys Thr Val Gly Tyr
            290                 295                 300

Ala Val Thr Tyr His Ala Glu Gly Phe Leu Val Cys Lys Thr Thr Asp
305                 310                 315                 320

Thr Val Lys Gly Glu Arg Val Ser Phe Pro Val Cys Thr Tyr Val Pro
                325                 330                 335

Ser Thr Ile Cys Asp Gln Met Thr Gly Ile Leu Ala Thr Asp Val Thr
            340                 345                 350

Pro Glu Asp Ala Gln Lys Leu Leu Val Gly Leu Asn Gln Arg Ile Val
            355                 360                 365

Val Asn Gly Arg Thr Gln Arg Asn Thr Asn Thr Met Lys Asn Tyr Leu
            370                 375                 380

Leu Pro Ile Val Ala Val Ala Phe Ser Lys Trp Ala Arg Glu Tyr Lys
385                 390                 395                 400

Ala Asp Leu Asp Asp Glu Lys Pro Leu Gly Val Arg Glu Arg Ser Leu
```

-continued

```
                405                 410                 415
Thr Cys Cys Cys Leu Trp Ala Phe Lys Thr Arg Lys Met His Thr Met
            420                 425                 430

Tyr Lys Lys Pro Asp Thr Gln Thr Ile Val Lys Val Pro Ser Glu Phe
            435                 440                 445

Asn Ser Phe Val Ile Pro Ser Leu Trp Ser Thr Gly Leu Ala Ile Pro
        450                 455                 460

Val Arg Ser Arg Ile Lys Met Leu Leu Ala Lys Lys Thr Lys Arg Glu
465                 470                 475                 480

Leu Ile Pro Val Leu Asp Ala Ser Ser Ala Arg Asp Ala Glu Gln Glu
            485                 490                 495

Glu Lys Glu Arg Leu Glu Ala Glu Leu Thr Arg Glu Ala Leu Pro Pro
            500                 505                 510

Leu Val Pro Ile Ala Pro Ala Glu Thr Gly Val Val Asp Val Asp Val
            515                 520                 525

Glu Glu Leu Glu Tyr His Ala Gly Ala Gly Val Val Glu Thr Pro Arg
            530                 535                 540

Ser Ala Leu Lys Val Thr Ala Gln Pro Asn Asp Val Leu Leu Gly Asn
545                 550                 555                 560

Tyr Val Val Leu Ser Pro Gln Thr Val Leu Lys Ser Ser Lys Leu Ala
                565                 570                 575

Pro Val His Pro Leu Ala Glu Gln Val Lys Ile Ile Thr His Asn Gly
            580                 585                 590

Arg Ala Gly Gly Tyr Gln Val Asp Gly Tyr Asp Gly Arg Val Leu Leu
            595                 600                 605

Pro Cys Gly Ser Ala Ile Pro Val Pro Glu Phe Gln Ala Leu Ser Glu
            610                 615                 620

Ser Ala Thr Met Val Tyr Asn Glu Arg Glu Phe Val Asn Arg Lys Leu
625                 630                 635                 640

Tyr His Ile Ala Val His Gly Pro Ser Leu Asn Thr Asp Glu Glu Asn
                645                 650                 655

Tyr Glu Lys Val Arg Ala Glu Arg Thr Asp Ala Glu Tyr Val Phe Asp
            660                 665                 670

Val Asp Lys Lys Cys Cys Val Lys Arg Glu Glu Ala Ser Gly Leu Val
            675                 680                 685

Leu Val Gly Glu Leu Thr Asn Pro Pro Phe His Glu Phe Ala Tyr Glu
            690                 695                 700

Gly Leu Lys Ile Arg Pro Ser Ala Pro Tyr Lys Thr Thr Val Val Gly
705                 710                 715                 720

Val Phe Gly Val Pro Gly Ser Gly Lys Ser Ala Ile Ile Lys Ser Leu
                725                 730                 735

Val Thr Lys His Asp Leu Val Thr Ser Gly Lys Lys Glu Asn Cys Gln
            740                 745                 750

Glu Ile Val Asn Asp Val Lys Lys His Arg Gly Lys Gly Thr Ser Arg
            755                 760                 765

Glu Asn Ser Asp Ser Ile Leu Leu Asn Gly Cys Arg Arg Ala Val Asp
            770                 775                 780

Ile Leu Tyr Val Asp Glu Ala Phe Ala Cys His Ser Gly Thr Leu Leu
785                 790                 795                 800

Ala Leu Ile Ala Leu Val Lys Pro Arg Ser Lys Val Val Leu Cys Gly
                805                 810                 815

Asp Pro Lys Gln Cys Gly Phe Phe Asn Met Met Gln Leu Lys Val Asn
            820                 825                 830
```

-continued

```
Phe Asn His Asn Ile Cys Thr Glu Val Cys His Lys Ser Ile Ser Arg
        835                 840                 845

Arg Cys Thr Arg Pro Val Thr Ala Ile Val Ser Thr Leu His Tyr Gly
    850                 855                 860

Gly Lys Met Arg Thr Thr Asn Pro Cys Asn Lys Pro Ile Ile Ile Asp
865                 870                 875                 880

Thr Thr Gly Gln Thr Lys Pro Lys Pro Gly Asp Ile Val Leu Thr Cys
                885                 890                 895

Phe Arg Gly Trp Ala Lys Gln Leu Gln Leu Asp Tyr Arg Gly His Glu
        900                 905                 910

Val Met Thr Ala Ala Ser Gln Gly Leu Thr Arg Lys Gly Val Tyr
        915                 920                 925

Ala Val Arg Gln Lys Val Asn Glu Asn Pro Leu Tyr Ala Pro Ala Ser
    930                 935                 940

Glu His Val Asn Val Leu Leu Thr Arg Thr Glu Asp Arg Leu Val Trp
945                 950                 955                 960

Lys Thr Leu Ala Gly Asp Pro Trp Ile Lys Val Leu Ser Asn Ile Pro
                965                 970                 975

Gln Gly Asn Phe Thr Ala Thr Leu Glu Glu Trp Gln Glu Glu His Asp
        980                 985                 990

Lys Ile Met Lys Val Ile Glu Gly  Pro Ala Ala Pro Val  Asp Ala Phe
        995                 1000                1005

Gln Asn  Lys Ala Asn Val Cys  Trp Ala Lys Ser Leu  Val Pro Val
    1010                1015                1020

Leu Asp  Thr Ala Gly Ile Arg  Leu Thr Ala Glu Glu  Trp Ser Thr
    1025                1030                1035

Ile Ile  Thr Ala Phe Lys Glu  Asp Arg Ala Tyr Ser  Pro Val Val
    1040                1045                1050

Ala Leu  Asn Glu Ile Cys Thr  Lys Tyr Tyr Gly Val  Asp Leu Asp
    1055                1060                1065

Ser Gly  Leu Phe Ser Ala Pro  Lys Val Ser Leu Tyr  Tyr Glu Asn
    1070                1075                1080

Asn His  Trp Asp Asn Arg Pro  Gly Gly Arg Met Tyr  Gly Phe Asn
    1085                1090                1095

Ala Ala  Thr Ala Ala Arg Leu  Glu Ala Arg His Thr  Phe Leu Lys
    1100                1105                1110

Gly Gln  Trp His Thr Gly Lys  Gln Ala Val Ile Ala  Glu Arg Lys
    1115                1120                1125

Ile Gln  Pro Leu Ser Val Leu  Asp Asn Val Ile Pro  Ile Asn Arg
    1130                1135                1140

Arg Leu  Pro His Ala Leu Val  Ala Glu Tyr Lys Thr  Val Lys Gly
    1145                1150                1155

Ser Arg  Val Glu Trp Leu Val  Asn Lys Val Arg Gly  Tyr His Val
    1160                1165                1170

Leu Leu  Val Ser Glu Tyr Asn  Leu Ala Leu Pro Arg  Arg Arg Val
    1175                1180                1185

Thr Trp  Leu Ser Pro Leu Asn  Val Thr Gly Ala Asp  Arg Cys Tyr
    1190                1195                1200

Asp Leu  Ser Leu Gly Leu Pro  Ala Asp Ala Gly Arg  Phe Asp Leu
    1205                1210                1215

Val Phe  Val Asn Ile His Thr  Glu Phe Arg Ile His  His Tyr Gln
    1220                1225                1230
```

```
Gln Cys Val Asp His Ala Met Lys Leu Gln Met Leu Gly Gly Asp
1235                1240                1245

Ala Leu Arg Leu Leu Lys Pro Gly Gly Ile Leu Met Arg Ala Tyr
1250                1255                1260

Gly Tyr Ala Asp Lys Ile Ser Glu Ala Val Val Ser Ser Leu Ser
1265                1270                1275

Arg Lys Phe Ser Ser Ala Arg Val Leu Arg Pro Asp Cys Val Thr
1280                1285                1290

Ser Asn Thr Glu Val Phe Leu Leu Phe Ser Asn Phe Asp Asn Gly
1295                1300                1305

Lys Arg Pro Ser Thr Leu His Gln Met Asn Thr Lys Leu Ser Ala
1310                1315                1320

Val Tyr Ala Gly Glu Ala Met His Thr Ala Gly Cys Ala Pro Ser
1325                1330                1335

Tyr Arg Val Lys Arg Ala Asp Ile Ala Thr Cys Thr Glu Ala Ala
1340                1345                1350

Val Val Asn Ala Ala Asn Ala Arg Gly Thr Val Gly Asp Gly Val
1355                1360                1365

Cys Arg Ala Val Ala Lys Lys Trp Pro Ser Ala Phe Lys Gly Ala
1370                1375                1380

Ala Thr Pro Val Gly Thr Ile Lys Thr Val Met Cys Gly Ser Tyr
1385                1390                1395

Pro Val Ile His Ala Val Ala Pro Asn Phe Ser Ala Thr Thr Glu
1400                1405                1410

Ala Glu Gly Asp Arg Glu Leu Ala Ala Val Tyr Arg Ala Val Ala
1415                1420                1425

Ala Glu Val Asn Arg Leu Ser Leu Ser Ser Val Ala Ile Pro Leu
1430                1435                1440

Leu Ser Thr Gly Val Phe Ser Gly Gly Arg Asp Arg Leu Gln Gln
1445                1450                1455

Ser Leu Asn His Leu Phe Thr Ala Met Asp Ala Thr Asp Ala Asp
1460                1465                1470

Val Thr Ile Tyr Cys Arg Asp Lys Ser Trp Glu Lys Lys Ile Gln
1475                1480                1485

Glu Ala Ile Asp Met Arg Thr Ala Val Glu Leu Leu Asn Asp Asp
1490                1495                1500

Val Glu Leu Thr Thr Asp Leu Val Arg Val His Pro Asp Ser Ser
1505                1510                1515

Leu Val Gly Arg Lys Gly Tyr Ser Thr Thr Asp Gly Ser Leu Tyr
1520                1525                1530

Ser Tyr Phe Glu Gly Thr Lys Phe Asn Gln Ala Ala Ile Asp Met
1535                1540                1545

Ala Glu Ile Leu Thr Leu Trp Pro Arg Leu Gln Glu Ala Asn Glu
1550                1555                1560

Arg Ile Cys Leu Tyr Ala Leu Gly Glu Thr Met Asp Asn Ile Gly
1565                1570                1575

Ser Lys Cys Pro Val Asn Asp Ser Asp Ser Ser Thr Pro Pro Arg
1580                1585                1590

Thr Val Pro Cys Leu Cys Arg Tyr Ala Met Thr Ala Glu Arg Ile
1595                1600                1605

Ala Arg Leu Arg Ser His Gln Val Lys Ser Met Val Val Cys Ser
1610                1615                1620

Ser Phe Pro Leu Pro Lys Tyr His Val Asp Gly Val Gln Lys Val
```

```
            1625                1630                1635
Lys Cys Glu Lys Val Leu Leu Phe Asp Pro Thr Val Pro Ser Val
            1640                1645                1650

Val Ser Pro Arg Lys Tyr Ala Ala Ser Thr Thr Asp His Ser Asp
            1655                1660                1665

Arg Ser Leu Arg Gly Phe Asp Leu Asp Trp Thr Thr Asp Ser Ser
            1670                1675                1680

Ser Thr Ala Ser Asp Thr Met Ser Leu Pro Ser Leu Gln Ser Cys
            1685                1690                1695

Asp Ile Asp Ser Ile Tyr Glu Pro Met Ala Pro Ile Val Val Thr
            1700                1705                1710

Ala Asp Val His Pro Glu Pro Ala Gly Ile Ala Asp Leu Ala Ala
            1715                1720                1725

Asp Val His Pro Glu Pro Ala Asp His Val Asp Leu Glu Asn Pro
            1730                1735                1740

Ile Pro Pro Pro Arg Pro Lys Arg Ala Ala Tyr Leu Ala Ser Arg
            1745                1750                1755

Ala Ala Glu Arg Pro Val Pro Ala Pro Arg Lys Pro Thr Pro Ala
            1760                1765                1770

Pro Arg Thr Ala Phe Arg Asn Lys Leu Pro Leu Thr Phe Gly Asp
            1775                1780                1785

Phe Asp Glu His Glu Val Asp Ala Leu Ala Ser Gly Ile Thr Phe
            1790                1795                1800

Gly Asp Phe Asp Asp Val Leu Arg Leu Gly Arg Ala Gly Ala Tyr
            1805                1810                1815

Ile Phe Ser Ser Asp Thr Gly Ser Gly His Leu Gln Gln Lys Ser
            1820                1825                1830

Val Arg Gln His Asn Leu Gln Cys Ala Gln Leu Asp Ala Val Gln
            1835                1840                1845

Glu Glu Lys Met Tyr Pro Pro Lys Leu Asp Thr Glu Arg Glu Lys
            1850                1855                1860

Leu Leu Leu Leu Lys Met Gln Met His Pro Ser Glu Ala Asn Lys
            1865                1870                1875

Ser Arg Tyr Gln Ser Arg Lys Val Glu Asn Met Lys Ala Thr Val
            1880                1885                1890

Val Asp Arg Leu Thr Ser Gly Ala Arg Leu Tyr Thr Gly Ala Asp
            1895                1900                1905

Val Gly Arg Ile Pro Thr Tyr Ala Val Arg Tyr Pro Arg Pro Val
            1910                1915                1920

Tyr Ser Pro Thr Val Ile Glu Arg Phe Ser Ser Pro Asp Val Ala
            1925                1930                1935

Ile Ala Ala Cys Asn Glu Tyr Leu Ser Arg Asn Tyr Pro Thr Val
            1940                1945                1950

Ala Ser Tyr Gln Ile Thr Asp Glu Tyr Asp Ala Tyr Leu Asp Met
            1955                1960                1965

Val Asp Gly Ser Asp Ser Cys Leu Asp Arg Ala Thr Phe Cys Pro
            1970                1975                1980

Ala Lys Leu Arg Cys Tyr Pro Lys His His Ala Tyr His Gln Pro
            1985                1990                1995

Thr Val Arg Ser Ala Val Pro Ser Pro Phe Gln Asn Thr Leu Gln
            2000                2005                2010

Asn Val Leu Ala Ala Ala Thr Lys Arg Asn Cys Asn Val Thr Gln
            2015                2020                2025
```

Met Arg Glu Leu Pro Thr Met Asp Ser Ala Val Phe Asn Val Glu
2030                2035                2040

Cys Phe Lys Arg Tyr Ala Cys Ser Gly Glu Tyr Trp Glu Glu Tyr
2045                2050                2055

Ala Lys Gln Pro Ile Arg Ile Thr Thr Glu Asn Ile Thr Thr Tyr
2060                2065                2070

Val Thr Lys Leu Lys Gly Pro Lys Ala Ala Ala Leu Phe Ala Lys
2075                2080                2085

Thr His Asn Leu Val Pro Leu Gln Glu Val Pro Met Asp Arg Phe
2090                2095                2100

Thr Val Asp Met Lys Arg Asp Val Lys Val Thr Pro Gly Thr Lys
2105                2110                2115

His Thr Glu Glu Arg Pro Lys Val Gln Val Ile Gln Ala Ala Glu
2120                2125                2130

Pro Leu Ala Thr Ala Tyr Leu Cys Gly Ile His Arg Glu Leu Val
2135                2140                2145

Arg Arg Leu Asn Ala Val Leu Arg Pro Asn Val His Thr Leu Phe
2150                2155                2160

Asp Met Ser Ala Glu Asp Phe Asp Ala Ile Ile Ala Ser His Phe
2165                2170                2175

His Pro Gly Asp Pro Val Leu Glu Thr Asp Ile Ala Ser Phe Asp
2180                2185                2190

Lys Ser Gln Asp Asp Ser Leu Ala Leu Thr Gly Leu Met Ile Leu
2195                2200                2205

Glu Asp Leu Gly Val Asp Gln Tyr Leu Leu Asp Leu Ile Glu Ala
2210                2215                2220

Ala Phe Gly Glu Ile Ser Ser Cys His Leu Pro Thr Gly Thr Arg
2225                2230                2235

Phe Lys Phe Gly Ala Met Met Lys Ser Gly Met Phe Leu Thr Leu
2240                2245                2250

Phe Ile Asn Thr Val Leu Asn Ile Thr Ile Ala Ser Arg Val Leu
2255                2260                2265

Glu Gln Arg Leu Thr Asp Ser Ala Cys Ala Ala Phe Ile Gly Asp
2270                2275                2280

Asp Asn Ile Val His Gly Val Ile Ser Asp Lys Leu Met Ala Glu
2285                2290                2295

Arg Cys Ala Ser Trp Val Asn Met Glu Val Lys Ile Ile Asp Ala
2300                2305                2310

Val Met Gly Glu Lys Pro Pro Tyr Phe Cys Gly Gly Phe Ile Val
2315                2320                2325

Phe Asp Ser Val Thr Gln Thr Ala Cys Arg Val Ser Asp Pro Leu
2330                2335                2340

Lys Arg Leu Phe Lys Leu Gly Lys Pro Leu Thr Ala Glu Asp Lys
2345                2350                2355

Gln Asp Glu Asp Arg Arg Arg Ala Leu Ser Asp Glu Val Ser Lys
2360                2365                2370

Trp Phe Arg Thr Gly Leu Gly Ala Glu Leu Glu Val Ala Leu Thr
2375                2380                2385

Ser Arg Tyr Glu Val Glu Gly Cys Lys Ser Ile Leu Ile Ala Met
2390                2395                2400

Thr Thr Leu Ala Arg Asp Ile Lys Ala Phe Lys Lys Leu Arg Gly
2405                2410                2415

```
Pro Val Ile His Leu Tyr Gly  Gly Pro Arg Leu Val  Arg
    2420                2425             2430
```

<210> SEQ ID NO 4
<211> LENGTH: 2512
<212> TYPE: PRT
<213> ORGANISM: Sindbis virus

<400> SEQUENCE: 4

```
Met Glu Lys Pro Val Val Asn Val Asp Val Pro Gln Ser Pro Phe
1               5                   10                  15

Val Val Gln Leu Gln Lys Ser Phe Pro Gln Phe Glu Val Val Ala Gln
                20                  25                  30

Gln Val Thr Pro Asn Asp His Ala Asn Ala Arg Ala Phe Ser His Leu
            35                  40                  45

Ala Ser Lys Leu Ile Glu Leu Glu Val Pro Thr Thr Ala Thr Ile Leu
    50                  55                  60

Asp Ile Gly Ser Ala Pro Ala Arg Arg Met Phe Ser Glu His Gln Tyr
65                  70                  75                  80

His Cys Val Cys Pro Met Arg Ser Pro Glu Asp Pro Asp Arg Met Met
                85                  90                  95

Lys Tyr Ala Ser Lys Leu Ala Glu Lys Ala Cys Lys Ile Thr Asn Lys
                100                 105                 110

Asn Leu His Glu Lys Ile Lys Asp Leu Arg Thr Val Leu Asp Thr Pro
            115                 120                 125

Asp Ala Glu Thr Pro Ser Leu Cys Phe His Asn Asp Val Thr Cys Asn
    130                 135                 140

Met Arg Ala Glu Tyr Ser Val Met Gln Asp Val Tyr Ile Asn Ala Pro
145                 150                 155                 160

Gly Thr Ile Tyr His Gln Ala Met Lys Gly Val Arg Thr Leu Tyr Trp
                165                 170                 175

Ile Gly Phe Asp Thr Thr Gln Phe Met Phe Ser Ala Met Ala Gly Ser
                180                 185                 190

Tyr Pro Ala Tyr Asn Thr Asn Trp Ala Asp Glu Lys Val Leu Glu Ala
            195                 200                 205

Arg Asn Ile Gly Leu Cys Ser Thr Lys Leu Ser Glu Gly Arg Thr Gly
    210                 215                 220

Lys Leu Ser Ile Met Arg Lys Lys Glu Leu Lys Pro Gly Ser Arg Val
225                 230                 235                 240

Tyr Phe Ser Val Gly Ser Thr Leu Tyr Pro Glu His Arg Ala Ser Leu
                245                 250                 255

Gln Ser Trp His Leu Pro Ser Val Phe His Leu Asn Gly Lys Gln Ser
                260                 265                 270

Tyr Thr Cys Arg Cys Asp Thr Val Val Ser Cys Glu Gly Tyr Val Val
            275                 280                 285

Lys Lys Ile Thr Ile Ser Pro Gly Ile Thr Gly Glu Thr Val Gly Tyr
    290                 295                 300

Ala Val Thr His Asn Ser Glu Gly Phe Leu Leu Cys Lys Val Thr Asp
305                 310                 315                 320

Thr Val Lys Gly Glu Arg Val Ser Phe Pro Val Cys Thr Tyr Ile Pro
                325                 330                 335

Ala Thr Ile Cys Asp Gln Met Thr Gly Ile Met Ala Thr Asp Ile Ser
                340                 345                 350

Pro Asp Asp Ala Gln Lys Leu Leu Val Gly Leu Asn Gln Arg Ile Val
            355                 360                 365
```

```
Ile Asn Gly Arg Thr Asn Arg Asn Thr Asn Thr Met Gln Asn Tyr Leu
    370                 375                 380

Leu Pro Ile Ile Ala Gln Gly Phe Ser Lys Trp Ala Lys Glu Arg Lys
385                 390                 395                 400

Asp Asp Leu Asp Asn Glu Lys Met Leu Gly Thr Arg Glu Arg Lys Leu
                405                 410                 415

Thr Tyr Gly Cys Leu Trp Ala Phe Arg Thr Lys Lys Val His Ser Phe
            420                 425                 430

Tyr Arg Pro Pro Gly Thr Gln Thr Cys Val Lys Val Pro Ala Ser Phe
        435                 440                 445

Ser Ala Phe Pro Met Ser Ser Val Trp Thr Thr Ser Leu Pro Met Ser
450                 455                 460

Leu Arg Gln Lys Leu Lys Leu Ala Leu Gln Pro Lys Lys Glu Lys
465                 470                 475                 480

Leu Leu Gln Val Ser Glu Glu Leu Val Met Glu Ala Lys Ala Phe
                485                 490                 495

Glu Asp Ala Gln Glu Glu Ala Arg Ala Glu Lys Leu Arg Glu Ala Leu
                500                 505                 510

Pro Pro Leu Val Ala Asp Lys Gly Ile Glu Ala Ala Ala Glu Val Val
                515                 520                 525

Cys Glu Val Glu Gly Leu Gln Ala Asp Ile Gly Ala Ala Leu Val Glu
530                 535                 540

Thr Pro Arg Gly His Val Arg Ile Ile Pro Gln Ala Asn Asp Arg Met
545                 550                 555                 560

Ile Gly Gln Tyr Ile Val Val Ser Pro Asn Ser Val Leu Lys Asn Ala
                565                 570                 575

Lys Leu Ala Pro Ala His Pro Leu Ala Asp Gln Val Lys Ile Ile Thr
            580                 585                 590

His Ser Gly Arg Ser Gly Arg Tyr Ala Val Glu Pro Tyr Asp Ala Lys
        595                 600                 605

Val Leu Met Pro Ala Gly Gly Ala Val Pro Trp Pro Glu Phe Leu Ala
610                 615                 620

Leu Ser Glu Ser Ala Thr Leu Val Tyr Asn Glu Arg Glu Phe Val Asn
625                 630                 635                 640

Arg Lys Leu Tyr His Ile Ala Met His Gly Pro Ala Lys Asn Thr Glu
                645                 650                 655

Glu Glu Gln Tyr Lys Val Thr Lys Ala Glu Leu Ala Glu Thr Glu Tyr
            660                 665                 670

Val Phe Asp Val Asp Lys Lys Arg Cys Val Lys Lys Glu Glu Ala Ser
        675                 680                 685

Gly Leu Val Leu Ser Gly Glu Leu Thr Asn Pro Pro Tyr His Glu Leu
690                 695                 700

Ala Leu Glu Gly Leu Lys Thr Arg Pro Ala Val Pro Tyr Lys Val Glu
705                 710                 715                 720

Thr Ile Gly Val Ile Gly Thr Pro Gly Ser Gly Lys Ser Ala Ile Ile
                725                 730                 735

Lys Ser Thr Val Thr Ala Arg Asp Leu Val Thr Ser Gly Lys Lys Glu
            740                 745                 750

Asn Cys Arg Glu Ile Glu Ala Asp Val Leu Arg Leu Arg Gly Met Gln
        755                 760                 765

Ile Thr Ser Lys Thr Val Asp Ser Val Met Leu Asn Gly Cys His Lys
770                 775                 780
```

```
Ala Val Glu Val Leu Tyr Val Asp Glu Ala Phe Ala Cys His Ala Gly
785                 790                 795                 800

Ala Leu Leu Ala Leu Ile Ala Ile Val Arg Pro Arg Lys Lys Val Val
            805                 810                 815

Leu Cys Gly Asp Pro Met Gln Cys Gly Phe Phe Asn Met Met Gln Leu
                820                 825                 830

Lys Val His Phe Asn His Pro Glu Lys Asp Ile Cys Thr Lys Thr Phe
            835                 840                 845

Tyr Lys Tyr Ile Ser Arg Arg Cys Thr Gln Pro Val Thr Ala Ile Val
            850                 855                 860

Ser Thr Leu His Tyr Asp Gly Lys Met Lys Thr Thr Asn Pro Cys Lys
865                 870                 875                 880

Lys Asn Ile Glu Ile Asp Ile Thr Gly Ala Thr Lys Pro Lys Pro Gly
                885                 890                 895

Asp Ile Ile Leu Thr Cys Phe Arg Gly Trp Val Lys Gln Leu Gln Ile
                900                 905                 910

Asp Tyr Pro Gly His Glu Val Met Thr Ala Ala Ala Ser Gln Gly Leu
            915                 920                 925

Thr Arg Lys Gly Val Tyr Ala Val Arg Gln Lys Val Asn Glu Asn Pro
            930                 935                 940

Leu Tyr Ala Ile Thr Ser Glu His Val Asn Val Leu Leu Thr Arg Thr
945                 950                 955                 960

Glu Asp Arg Leu Val Trp Lys Thr Leu Gln Gly Asp Pro Trp Ile Lys
                965                 970                 975

Gln Pro Thr Asn Ile Pro Lys Gly Asn Phe Gln Ala Thr Ile Glu Asp
            980                 985                 990

Trp Glu Ala Glu His Lys Gly Ile Ile Ala Ala Ile Asn Ser Pro Thr
            995                 1000                1005

Pro Arg Ala Asn Pro Phe Ser  Cys Lys Thr Asn Val  Cys Trp Ala
    1010                1015                 1020

Lys Ala Leu Glu Pro Ile Leu  Ala Thr Ala Gly Ile  Val Leu Thr
    1025                1030                 1035

Gly Cys Gln Trp Ser Glu Leu  Phe Pro Gln Phe Ala  Asp Asp Lys
    1040                1045                 1050

Pro His Ser Ala Ile Tyr Ala  Leu Asp Val Ile Cys  Ile Lys Phe
    1055                1060                 1065

Phe Gly Met Asp Leu Thr Ser  Gly Leu Phe Ser Lys  Gln Ser Ile
    1070                1075                 1080

Pro Leu Thr Tyr His Pro Ala  Asp Ser Ala Arg Pro  Val Ala His
    1085                1090                 1095

Trp Asp Asn Ser Pro Gly Thr  Arg Lys Tyr Gly Tyr  Asp His Ala
    1100                1105                 1110

Ile Ala Ala Glu Leu Ser Arg  Arg Phe Pro Val Phe  Gln Leu Ala
    1115                1120                 1125

Gly Lys Gly Thr Gln Leu Asp  Leu Gln Thr Gly Arg  Thr Arg Val
    1130                1135                 1140

Ile Ser Ala Gln His Asn Leu  Val Pro Val Asn Arg  Asn Leu Pro
    1145                1150                 1155

His Ala Leu Val Pro Glu Tyr  Lys Glu Lys Gln Pro  Gly Pro Val
    1160                1165                 1170

Lys Lys Phe Leu Asn Gln Phe  Lys His His Ser Val  Leu Val Val
    1175                1180                 1185

Ser Glu Glu Lys Ile Glu Ala  Pro Arg Lys Arg Ile  Glu Trp Ile
```

```
            1190                1195                1200
Ala Pro Ile Gly Ile Ala Gly Ala Asp Lys Asn Tyr  Asn Leu Ala
    1205                1210                1215
Phe Gly Phe Pro Pro Gln Ala Arg Tyr Asp Leu Val  Phe Ile Asn
    1220                1225                1230
Ile Gly Thr Lys Tyr Arg Asn His His Phe Gln Gln  Cys Glu Asp
    1235                1240                1245
His Ala Ala Thr Leu Lys Thr Leu Ser Arg Ser Ala  Leu Asn Cys
    1250                1255                1260
Leu Asn Pro Gly Gly Thr Leu Val Val Lys Ser Tyr  Gly Tyr Ala
    1265                1270                1275
Asp Arg Asn Ser Glu Asp Val Val Thr Ala Leu Ala  Arg Lys Phe
    1280                1285                1290
Val Arg Val Ser Ala Ala Arg Pro Asp Cys Val Ser  Ser Asn Thr
    1295                1300                1305
Glu Met Tyr Leu Ile Phe Arg Gln Leu Asp Asn Ser  Arg Thr Arg
    1310                1315                1320
Gln Phe Thr Pro His His Leu Asn Cys Val Ile Ser  Ser Val Tyr
    1325                1330                1335
Glu Gly Thr Arg Asp Gly Val Gly Ala Ala Pro Ser  Tyr Arg Thr
    1340                1345                1350
Lys Arg Glu Asn Ile Ala Asp Cys Gln Glu Glu Ala  Val Val Asn
    1355                1360                1365
Ala Ala Asn Pro Leu Gly Arg Pro Gly Glu Gly Val  Cys Arg Ala
    1370                1375                1380
Ile Tyr Lys Arg Trp Pro Thr Ser Phe Thr Asp Ser  Ala Thr Glu
    1385                1390                1395
Thr Gly Thr Ala Arg Met Thr Val Cys Leu Gly Lys  Lys Val Ile
    1400                1405                1410
His Ala Val Gly Pro Asp Phe Arg Lys His Pro Glu  Ala Glu Ala
    1415                1420                1425
Leu Lys Leu Leu Gln Asn Ala Tyr His Ala Val Ala  Asp Leu Val
    1430                1435                1440
Asn Glu His Asn Ile Lys Ser Val Ala Ile Pro Leu  Leu Ser Thr
    1445                1450                1455
Gly Ile Tyr Ala Ala Gly Lys Asp Arg Leu Glu Val  Ser Leu Asn
    1460                1465                1470
Cys Leu Thr Thr Ala Leu Asp Arg Thr Asp Ala Asp  Val Thr Ile
    1475                1480                1485
Tyr Cys Leu Asp Lys Lys Trp Lys Glu Arg Ile Asp  Ala Ala Leu
    1490                1495                1500
Gln Leu Lys Glu Ser Val Thr Glu Leu Lys Asp Glu  Asp Met Glu
    1505                1510                1515
Ile Asp Asp Glu Leu Val Trp Ile His Pro Asp Ser  Cys Leu Lys
    1520                1525                1530
Gly Arg Lys Gly Phe Ser Thr Thr Lys Gly Lys Leu  Tyr Ser Tyr
    1535                1540                1545
Phe Glu Gly Thr Lys Phe His Gln Ala Ala Lys Asp  Met Ala Glu
    1550                1555                1560
Ile Lys Val Leu Phe Pro Asn Asp Gln Glu Ser Asn  Glu Gln Leu
    1565                1570                1575
Cys Ala Tyr Ile Leu Gly Glu Thr Met Glu Ala Ile  Arg Glu Lys
    1580                1585                1590
```

```
Cys Pro Val Asp His Asn Pro Ser Ser Pro Pro Lys Thr Leu
    1595                1600            1605
Pro Cys Leu Cys Met Tyr Ala Met Thr Pro Glu Arg Val His Arg
    1610            1615            1620
Leu Arg Ser Asn Asn Val Lys Glu Val Thr Val Cys Ser Ser Thr
    1625            1630            1635
Pro Leu Pro Lys His Lys Ile Lys Asn Val Gln Lys Val Gln Cys
    1640            1645            1650
Thr Lys Val Val Leu Phe Asn Pro His Thr Pro Ala Phe Val Pro
    1655            1660            1665
Ala Arg Lys Tyr Ile Glu Val Pro Glu Gln Pro Thr Ala Pro Pro
    1670            1675            1680
Ala Gln Ala Glu Glu Ala Pro Glu Val Val Ala Thr Pro Ser Pro
    1685            1690            1695
Ser Thr Ala Asp Asn Thr Ser Leu Asp Val Thr Asp Ile Ser Leu
    1700            1705            1710
Asp Met Asp Asp Ser Ser Glu Gly Ser Leu Phe Ser Ser Phe Ser
    1715            1720            1725
Gly Ser Asp Asn Ser Ile Thr Ser Met Asp Ser Trp Ser Ser Gly
    1730            1735            1740
Pro Ser Ser Leu Glu Ile Val Asp Arg Arg Gln Val Val Val Ala
    1745            1750            1755
Asp Val His Ala Val Gln Glu Pro Ala Pro Ile Pro Pro Pro Arg
    1760            1765            1770
Leu Lys Lys Met Ala Arg Leu Ala Ala Ala Arg Lys Glu Pro Thr
    1775            1780            1785
Pro Pro Ala Ser Asn Ser Ser Glu Ser Leu His Leu Ser Phe Gly
    1790            1795            1800
Gly Val Ser Met Ser Leu Gly Ser Ile Phe Asp Gly Glu Thr Ala
    1805            1810            1815
Arg Gln Ala Ala Val Gln Pro Leu Ala Thr Gly Pro Thr Asp Val
    1820            1825            1830
Pro Met Ser Phe Gly Ser Phe Ser Asp Gly Glu Ile Asp Glu Leu
    1835            1840            1845
Ser Arg Arg Val Thr Glu Ser Glu Pro Val Leu Phe Gly Ser Phe
    1850            1855            1860
Glu Pro Gly Glu Val Asn Ser Ile Ile Ser Ser Arg Ser Ala Val
    1865            1870            1875
Ser Phe Pro Leu Arg Lys Gln Arg Arg Arg Arg Ser Arg Arg
    1880            1885            1890
Thr Glu Tyr Leu Thr Gly Val Gly Gly Tyr Ile Phe Ser Thr Asp
    1895            1900            1905
Thr Gly Pro Gly His Leu Gln Lys Lys Ser Val Leu Gln Asn Gln
    1910            1915            1920
Leu Thr Glu Pro Thr Leu Glu Arg Asn Val Leu Glu Arg Ile His
    1925            1930            1935
Ala Pro Val Leu Asp Thr Ser Lys Glu Glu Gln Leu Lys Leu Arg
    1940            1945            1950
Tyr Gln Met Met Pro Thr Glu Ala Asn Lys Ser Arg Tyr Gln Ser
    1955            1960            1965
Arg Lys Val Glu Asn Gln Lys Ala Ile Thr Thr Glu Arg Leu Leu
    1970            1975            1980
```

-continued

Ser Gly Leu Arg Leu Tyr Asn Ser Ala Thr Asp Gln Pro Glu Cys
1985                     1990                1995

Tyr Lys Ile Thr Tyr Pro Lys Pro Leu Tyr Ser Ser Val Pro
2000                     2005                2010

Ala Asn Tyr Ser Asp Pro Gln Phe Ala Val Ala Val Cys Asn Asn
2015                     2020                2025

Tyr Leu His Glu Asn Tyr Pro Thr Val Ala Ser Tyr Gln Ile Thr
2030                     2035                2040

Asp Glu Tyr Asp Ala Tyr Leu Asp Met Val Asp Gly Thr Val Ala
2045                     2050                2055

Cys Leu Asp Thr Ala Thr Phe Cys Pro Ala Lys Leu Arg Ser Tyr
2060                     2065                2070

Pro Lys Lys His Glu Tyr Arg Ala Pro Asn Ile Arg Ser Ala Val
2075                     2080                2085

Pro Ser Ala Met Gln Asn Thr Leu Gln Asn Val Leu Ile Ala Ala
2090                     2095                2100

Thr Lys Arg Asn Cys Asn Val Thr Gln Met Arg Glu Leu Pro Thr
2105                     2110                2115

Leu Asp Ser Ala Thr Phe Asn Val Glu Cys Phe Arg Lys Tyr Ala
2120                     2125                2130

Cys Asn Asp Glu Tyr Trp Glu Glu Phe Ala Arg Lys Pro Ile Arg
2135                     2140                2145

Ile Thr Thr Glu Phe Val Thr Ala Tyr Val Ala Arg Leu Lys Gly
2150                     2155                2160

Pro Lys Ala Ala Ala Leu Phe Ala Lys Thr Tyr Asn Leu Val Pro
2165                     2170                2175

Leu Gln Glu Val Pro Met Asp Arg Phe Val Met Asp Met Lys Arg
2180                     2185                2190

Asp Val Lys Val Thr Pro Gly Thr Lys His Thr Glu Glu Arg Pro
2195                     2200                2205

Lys Val Gln Val Ile Gln Ala Ala Glu Pro Leu Ala Thr Ala Tyr
2210                     2215                2220

Leu Cys Gly Ile His Arg Glu Leu Val Arg Arg Leu Thr Ala Val
2225                     2230                2235

Leu Leu Pro Asn Ile His Thr Leu Phe Asp Met Ser Ala Glu Asp
2240                     2245                2250

Phe Asp Ala Ile Ile Ala Glu His Phe Lys Gln Gly Asp Pro Val
2255                     2260                2265

Leu Glu Thr Asp Ile Ala Ser Phe Asp Lys Ser Gln Asp Asp Ala
2270                     2275                2280

Met Ala Leu Thr Gly Leu Met Ile Leu Glu Asp Leu Gly Val Asp
2285                     2290                2295

Gln Pro Leu Leu Asp Leu Ile Glu Cys Ala Phe Gly Glu Ile Ser
2300                     2305                2310

Ser Thr His Leu Pro Thr Gly Thr Arg Phe Lys Phe Gly Ala Met
2315                     2320                2325

Met Lys Ser Gly Met Phe Leu Thr Leu Phe Val Asn Thr Val Leu
2330                     2335                2340

Asn Val Val Ile Ala Ser Arg Val Leu Glu Glu Arg Leu Lys Thr
2345                     2350                2355

Ser Arg Cys Ala Ala Phe Ile Gly Asp Asp Asn Ile Ile His Gly
2360                     2365                2370

Val Val Ser Asp Lys Glu Met Ala Glu Arg Cys Ala Thr Trp Leu 2375 2380 2385

Asn Met Glu Val Lys Ile Ile Asp Ala Val Ile Gly Glu Arg Pro
2390 2395 2400

Pro Tyr Phe Cys Gly Gly Phe Ile Leu Gln Asp Ser Val Thr Ser
2405 2410 2415

Thr Ala Cys Arg Val Ala Asp Pro Leu Lys Arg Leu Phe Lys Leu
2420 2425 2430

Gly Lys Pro Leu Pro Ala Asp Asp Glu Gln Asp Glu Asp Arg Arg
2435 2440 2445

Arg Ala Leu Leu Asp Glu Thr Lys Ala Trp Phe Arg Val Gly Ile
2450 2455 2460

Thr Gly Thr Leu Ala Val Ala Val Thr Thr Arg Tyr Glu Val Asp
2465 2470 2475

Asn Ile Thr Pro Val Leu Leu Ala Leu Arg Thr Phe Ala Gln Ser
2480 2485 2490

Lys Arg Ala Phe Gln Ala Ile Arg Gly Glu Ile Lys His Leu Tyr
2495 2500 2505

Gly Gly Pro Lys
2510

<210> SEQ ID NO 5
<211> LENGTH: 2474
<212> TYPE: PRT
<213> ORGANISM: Chikungunya virus

<400> SEQUENCE: 5

Met Asp Pro Val Tyr Val Asp Ile Asp Ala Asp Ser Ala Phe Leu Lys
1 5 10 15

Ala Leu Gln Arg Ala Tyr Pro Met Phe Glu Val Glu Pro Arg Gln Val
20 25 30

Thr Pro Asn Asp His Ala Asn Ala Arg Ala Phe Ser His Leu Ala Ile
35 40 45

Lys Leu Ile Glu Gln Glu Ile Asp Pro Asp Ser Thr Ile Leu Asp Ile
50 55 60

Gly Ser Ala Pro Ala Arg Arg Met Met Ser Asp Arg Lys Tyr His Cys
65 70 75 80

Val Cys Pro Met Arg Ser Ala Glu Asp Pro Glu Arg Leu Ala Asn Tyr
85 90 95

Ala Arg Lys Leu Ala Ser Ala Ala Gly Lys Val Leu Asp Arg Asn Ile
100 105 110

Ser Gly Lys Ile Gly Asp Leu Gln Ala Val Met Ala Val Pro Asp Thr
115 120 125

Glu Thr Pro Thr Phe Cys Leu His Thr Asp Val Ser Cys Arg Gln Arg
130 135 140

Ala Asp Val Ala Ile Tyr Gln Asp Val Tyr Ala Val His Ala Pro Thr
145 150 155 160

Ser Leu Tyr His Gln Ala Ile Lys Gly Val Arg Leu Ala Tyr Trp Val
165 170 175

Gly Phe Asp Thr Thr Pro Phe Met Tyr Asn Ala Met Ala Gly Ala Tyr
180 185 190

Pro Ser Tyr Ser Thr Asn Trp Ala Asp Glu Gln Val Leu Lys Ala Lys
195 200 205

Asn Ile Gly Leu Cys Ser Thr Asp Leu Thr Glu Gly Arg Arg Gly Lys
210 215 220

```
Leu Ser Ile Met Arg Gly Lys Lys Leu Glu Pro Cys Asp Arg Val Leu
225                 230                 235                 240

Phe Ser Val Gly Ser Thr Leu Tyr Pro Glu Ser Arg Lys Leu Leu Lys
            245                 250                 255

Ser Trp His Leu Pro Ser Val Phe His Leu Lys Gly Lys Leu Ser Phe
        260                 265                 270

Thr Cys Arg Cys Asp Thr Val Ser Cys Glu Gly Tyr Val Val Lys
    275                 280                 285

Arg Ile Thr Met Ser Pro Gly Leu Tyr Gly Lys Thr Thr Gly Tyr Ala
290                 295                 300

Val Thr His His Ala Asp Gly Phe Leu Met Cys Lys Thr Thr Asp Thr
305             310                 315                 320

Val Asp Gly Glu Arg Val Ser Phe Ser Val Cys Thr Tyr Val Pro Ala
                325                 330                 335

Thr Ile Cys Asp Gln Met Thr Gly Ile Leu Ala Thr Glu Val Thr Pro
            340                 345                 350

Glu Asp Ala Gln Lys Leu Leu Val Gly Leu Asn Gln Arg Ile Val Val
            355                 360                 365

Asn Gly Arg Thr Gln Arg Asn Thr Asn Thr Met Lys Asn Tyr Met Ile
370                 375                 380

Pro Val Val Ala Gln Ala Phe Ser Lys Trp Ala Lys Glu Cys Arg Lys
385                 390                 395                 400

Asp Met Glu Asp Glu Lys Leu Leu Gly Val Arg Glu Arg Thr Leu Thr
                405                 410                 415

Cys Cys Cys Leu Trp Ala Phe Lys Lys Gln Lys Thr His Thr Val Tyr
            420                 425                 430

Lys Arg Pro Asp Thr Gln Ser Ile Gln Lys Val Gln Ala Glu Phe Asp
        435                 440                 445

Ser Phe Val Val Pro Ser Leu Trp Ser Ser Gly Leu Ser Ile Pro Leu
        450                 455                 460

Arg Thr Arg Ile Lys Trp Leu Leu Ser Lys Val Pro Lys Thr Asp Leu
465                 470                 475                 480

Thr Pro Tyr Ser Gly Asp Ala Gln Glu Ala Arg Asp Ala Glu Lys Glu
                485                 490                 495

Ala Glu Glu Glu Arg Glu Ala Glu Leu Thr Leu Glu Ala Leu Pro Pro
            500                 505                 510

Leu Gln Ala Ala Gln Glu Asp Val Gln Val Glu Ile Asp Val Glu Gln
        515                 520                 525

Leu Glu Asp Arg Ala Gly Ala Gly Ile Ile Glu Thr Pro Arg Gly Ala
530                 535                 540

Ile Lys Val Thr Ala Gln Pro Thr Asp His Val Val Gly Glu Tyr Leu
545                 550                 555                 560

Val Leu Ser Pro Gln Thr Val Leu Arg Ser Gln Lys Leu Ser Leu Ile
            565                 570                 575

His Ala Leu Ala Glu Gln Val Lys Thr Cys Thr His Ser Gly Arg Ala
            580                 585                 590

Gly Arg Tyr Ala Val Glu Ala Tyr Asp Gly Arg Val Leu Val Pro Ser
        595                 600                 605

Gly Tyr Ala Ile Ser Pro Glu Asp Phe Gln Ser Leu Ser Glu Ser Ala
        610                 615                 620

Thr Met Val Tyr Asn Glu Arg Glu Phe Val Asn Arg Lys Leu His His
625                 630                 635                 640

Ile Ala Met His Gly Pro Ala Leu Asn Thr Asp Glu Glu Ser Tyr Glu
```

-continued

```
                645                 650                 655
Leu Val Arg Ala Glu Arg Thr Glu His Glu Tyr Val Tyr Asp Val Asp
                660                 665                 670
Gln Arg Arg Cys Cys Lys Lys Glu Glu Ala Ala Gly Leu Val Leu Val
                675                 680                 685
Gly Asp Leu Thr Asn Pro Pro Tyr His Glu Phe Ala Tyr Glu Gly Leu
                690                 695                 700
Lys Ile Arg Pro Ala Cys Pro Tyr Lys Ile Ala Val Ile Gly Val Phe
705                 710                 715                 720
Gly Val Pro Gly Ser Gly Lys Ser Ala Ile Ile Lys Asn Leu Val Thr
                725                 730                 735
Arg Gln Asp Leu Val Thr Ser Gly Lys Lys Glu Asn Cys Gln Glu Ile
                740                 745                 750
Thr Thr Asp Val Met Arg Gln Arg Gly Leu Glu Ile Ser Ala Arg Thr
                755                 760                 765
Val Asp Ser Leu Leu Leu Asn Gly Cys Asn Arg Pro Val Asp Val Leu
                770                 775                 780
Tyr Val Asp Glu Ala Phe Ala Cys His Ser Gly Thr Leu Leu Ala Leu
785                 790                 795                 800
Ile Ala Leu Val Arg Pro Arg Gln Lys Val Val Leu Cys Gly Asp Pro
                805                 810                 815
Lys Gln Cys Gly Phe Phe Asn Met Met Gln Met Lys Val Asn Tyr Asn
                820                 825                 830
His Asn Ile Cys Thr Gln Val Tyr His Lys Ser Ile Ser Arg Arg Cys
                835                 840                 845
Thr Leu Pro Val Thr Ala Ile Val Ser Ser Leu His Tyr Glu Gly Lys
                850                 855                 860
Met Arg Thr Thr Asn Glu Tyr Asn Lys Pro Ile Val Val Asp Thr Thr
865                 870                 875                 880
Gly Ser Thr Lys Pro Asp Pro Gly Asp Leu Val Leu Thr Cys Phe Arg
                885                 890                 895
Gly Trp Val Lys Gln Leu Gln Ile Asp Tyr Arg Gly His Glu Val Met
                900                 905                 910
Thr Ala Ala Ala Ser Gln Gly Leu Thr Arg Lys Gly Val Tyr Ala Val
                915                 920                 925
Arg Gln Lys Val Asn Glu Asn Pro Leu Tyr Ala Ser Thr Ser Glu His
                930                 935                 940
Val Asn Val Leu Leu Thr Arg Thr Glu Gly Lys Leu Val Trp Lys Thr
945                 950                 955                 960
Leu Ser Gly Asp Pro Trp Ile Lys Thr Leu Gln Asn Pro Pro Lys Gly
                965                 970                 975
Asn Phe Lys Ala Thr Ile Lys Glu Trp Glu Val Glu His Ala Ser Ile
                980                 985                 990
Met Ala Gly Ile Cys Ser His Gln Met Thr Phe Asp Thr Phe Gln Asn
                995                 1000                1005
Lys Ala Asn Val Cys Trp Ala Lys Ser Leu Val Pro Ile Leu Glu
        1010                1015                1020
Thr Ala Gly Ile Lys Leu Asn Asp Arg Gln Trp Ser Gln Ile Ile
        1025                1030                1035
Gln Ala Phe Lys Glu Asp Lys Ala Tyr Ser Pro Glu Val Ala Leu
        1040                1045                1050
Asn Glu Ile Cys Thr Arg Met Tyr Gly Val Asp Leu Asp Ser Gly
        1055                1060                1065
```

```
Leu Phe Ser Lys Pro Leu Val Ser Val Tyr Tyr Ala Asp Asn His
    1070                1075                1080

Trp Asp Asn Arg Pro Gly Gly Lys Met Phe Gly Phe Asn Pro Glu
    1085                1090                1095

Ala Ala Ser Ile Leu Glu Arg Lys Tyr Pro Phe Thr Lys Gly Lys
    1100                1105                1110

Trp Asn Ile Asn Lys Gln Ile Cys Val Thr Thr Arg Arg Ile Glu
    1115                1120                1125

Asp Phe Asn Pro Thr Thr Asn Ile Ile Pro Ala Asn Arg Arg Leu
    1130                1135                1140

Pro His Ser Leu Val Ala Glu His Arg Pro Val Lys Gly Glu Arg
    1145                1150                1155

Met Glu Trp Leu Val Asn Lys Ile Asn Gly His His Val Leu Leu
    1160                1165                1170

Val Ser Gly Cys Ser Leu Ala Leu Pro Thr Lys Arg Val Thr Trp
    1175                1180                1185

Val Ala Pro Leu Gly Val Arg Gly Ala Asp Tyr Thr Tyr Asn Leu
    1190                1195                1200

Glu Leu Gly Leu Pro Ala Thr Leu Gly Arg Tyr Asp Leu Val Val
    1205                1210                1215

Ile Asn Ile His Thr Pro Phe Arg Ile His His Tyr Gln Gln Cys
    1220                1225                1230

Val Asp His Ala Met Lys Leu Gln Met Leu Gly Gly Asp Ser Leu
    1235                1240                1245

Arg Leu Leu Lys Pro Gly Gly Ser Leu Leu Ile Arg Ala Tyr Gly
    1250                1255                1260

Tyr Ala Asp Arg Thr Ser Glu Arg Val Ile Cys Val Leu Gly Arg
    1265                1270                1275

Lys Phe Arg Ser Ser Arg Ala Leu Lys Pro Pro Cys Val Thr Ser
    1280                1285                1290

Asn Thr Glu Met Phe Phe Leu Phe Ser Asn Phe Asp Asn Gly Arg
    1295                1300                1305

Arg Asn Phe Thr Thr His Val Met Asn Asn Gln Leu Asn Ala Ala
    1310                1315                1320

Phe Val Gly Gln Ala Thr Arg Ala Gly Cys Ala Pro Ser Tyr Arg
    1325                1330                1335

Val Lys Arg Met Asp Ile Ala Lys Asn Asp Glu Glu Cys Val Val
    1340                1345                1350

Asn Ala Ala Asn Pro Arg Gly Leu Pro Gly Asp Gly Val Cys Lys
    1355                1360                1365

Ala Val Tyr Lys Lys Trp Pro Glu Ser Phe Lys Asn Ser Ala Thr
    1370                1375                1380

Pro Val Gly Thr Ala Lys Thr Val Met Cys Gly Thr Tyr Pro Val
    1385                1390                1395

Ile His Ala Val Gly Pro Asn Phe Ser Asn Tyr Ser Glu Ser Glu
    1400                1405                1410

Gly Asp Arg Glu Leu Ala Ala Ala Tyr Arg Glu Val Ala Lys Glu
    1415                1420                1425

Val Thr Arg Leu Gly Val Asn Ser Val Ala Ile Pro Leu Leu Ser
    1430                1435                1440

Thr Gly Val Tyr Ser Gly Gly Lys Asp Arg Leu Thr Gln Ser Leu
    1445                1450                1455
```

```
Asn His Leu Phe Thr Ala Met Asp Ser Thr Asp Ala Asp Val Val
1460                1465                1470

Ile Tyr Cys Arg Asp Lys Glu Trp Glu Lys Lys Ile Ser Glu Ala
1475                1480                1485

Ile Gln Met Arg Thr Gln Val Glu Leu Leu Asp Glu His Ile Ser
1490                1495                1500

Ile Asp Cys Asp Val Val Arg Val His Pro Asp Ser Ser Leu Ala
1505                1510                1515

Gly Arg Lys Gly Tyr Ser Thr Thr Glu Gly Ala Leu Tyr Ser Tyr
1520                1525                1530

Leu Glu Gly Thr Arg Phe His Gln Thr Ala Val Asp Met Ala Glu
1535                1540                1545

Ile Tyr Thr Met Trp Pro Lys Gln Thr Glu Ala Asn Glu Gln Val
1550                1555                1560

Cys Leu Tyr Ala Leu Gly Glu Ser Ile Glu Ser Ile Arg Gln Lys
1565                1570                1575

Cys Pro Val Asp Asp Ala Asp Ala Ser Ser Pro Pro Lys Thr Val
1580                1585                1590

Pro Cys Leu Cys Arg Tyr Ala Met Thr Pro Glu Arg Val Thr Arg
1595                1600                1605

Leu Arg Met Asn His Val Thr Ser Ile Ile Val Cys Ser Ser Phe
1610                1615                1620

Pro Leu Pro Lys Tyr Lys Ile Glu Gly Val Gln Lys Val Lys Cys
1625                1630                1635

Ser Lys Val Met Leu Phe Asp His Asn Val Pro Ser Arg Val Ser
1640                1645                1650

Pro Arg Glu Tyr Arg Pro Ser Gln Glu Ser Val Gln Glu Ala Ser
1655                1660                1665

Thr Thr Thr Ser Leu Thr His Ser Gln Phe Asp Leu Ser Val Asp
1670                1675                1680

Gly Lys Ile Leu Pro Val Pro Ser Asp Leu Asp Ala Asp Ala Pro
1685                1690                1695

Ala Leu Glu Pro Ala Leu Asp Asp Gly Ala Ile His Thr Leu Pro
1700                1705                1710

Ser Ala Thr Gly Asn Leu Ala Ala Val Ser Asp Trp Val Met Ser
1715                1720                1725

Thr Val Pro Val Ala Pro Pro Arg Arg Arg Arg Gly Arg Asn Leu
1730                1735                1740

Thr Val Thr Cys Asp Glu Arg Glu Gly Asn Ile Thr Pro Met Ala
1745                1750                1755

Ser Val Arg Phe Phe Arg Ala Glu Leu Cys Pro Val Val Gln Glu
1760                1765                1770

Thr Ala Glu Thr Arg Asp Thr Ala Met Ser Leu Gln Ala Pro Pro
1775                1780                1785

Ser Thr Ala Thr Glu Leu Ser His Pro Pro Ile Ser Phe Gly Ala
1790                1795                1800

Pro Ser Glu Thr Phe Pro Ile Thr Phe Gly Asp Phe Asn Glu Gly
1805                1810                1815

Glu Ile Glu Ser Leu Ser Ser Glu Leu Leu Thr Phe Gly Asp Phe
1820                1825                1830

Leu Pro Gly Glu Val Asp Asp Leu Thr Asp Ser Asp Trp Ser Thr
1835                1840                1845

Cys Ser Asp Thr Asp Asp Glu Leu Arg Leu Asp Arg Ala Gly Gly
```

-continued

```
                1850                1855                1860
Tyr Ile Phe Ser Ser Asp Thr Gly Pro Gly His Leu Gln Gln Lys
                1865                1870                1875

Ser Val Arg Gln Ser Val Leu Pro Val Asn Thr Leu Glu Glu Val
                1880                1885                1890

His Glu Glu Lys Cys Tyr Pro Pro Lys Leu Asp Glu Ala Lys Glu
                1895                1900                1905

Gln Leu Leu Leu Lys Lys Leu Gln Glu Ser Ala Ser Met Ala Asn
                1910                1915                1920

Arg Ser Arg Tyr Gln Ser Arg Lys Val Glu Asn Met Lys Ala Thr
                1925                1930                1935

Ile Ile Gln Arg Leu Lys Arg Gly Cys Arg Leu Tyr Leu Met Ser
                1940                1945                1950

Glu Thr Pro Lys Val Pro Thr Tyr Arg Thr Thr Tyr Pro Ala Pro
                1955                1960                1965

Val Tyr Ser Pro Pro Ile Asn Val Arg Leu Ser Asn Pro Glu Ser
                1970                1975                1980

Ala Val Ala Ala Cys Asn Glu Phe Leu Ala Arg Asn Tyr Pro Thr
                1985                1990                1995

Val Ser Ser Tyr Gln Ile Thr Asp Glu Tyr Asp Ala Tyr Leu Asp
                2000                2005                2010

Met Val Asp Gly Ser Glu Ser Cys Leu Asp Arg Ala Thr Phe Asn
                2015                2020                2025

Pro Ser Lys Leu Arg Ser Tyr Pro Lys Gln His Ala Tyr His Ala
                2030                2035                2040

Pro Ser Ile Arg Ser Ala Val Pro Ser Pro Phe Gln Asn Thr Leu
                2045                2050                2055

Gln Asn Val Leu Ala Ala Ala Thr Lys Arg Asn Cys Asn Val Thr
                2060                2065                2070

Gln Met Arg Glu Leu Pro Thr Leu Asp Ser Ala Val Phe Asn Val
                2075                2080                2085

Glu Cys Phe Lys Lys Phe Ala Cys Asn Gln Glu Tyr Trp Glu Glu
                2090                2095                2100

Phe Ala Ala Ser Pro Ile Arg Ile Thr Thr Glu Asn Leu Thr Thr
                2105                2110                2115

Tyr Val Thr Lys Leu Lys Gly Pro Lys Ala Ala Ala Leu Phe Ala
                2120                2125                2130

Lys Thr His Asn Leu Leu Pro Leu Gln Glu Val Pro Met Asp Arg
                2135                2140                2145

Phe Thr Val Asp Met Lys Arg Asp Val Lys Val Thr Pro Gly Thr
                2150                2155                2160

Lys His Thr Glu Glu Arg Pro Lys Val Gln Val Ile Gln Ala Ala
                2165                2170                2175

Glu Pro Leu Ala Thr Ala Tyr Leu Cys Gly Ile His Arg Glu Leu
                2180                2185                2190

Val Arg Arg Leu Asn Ala Val Leu Leu Pro Asn Val His Thr Leu
                2195                2200                2205

Phe Asp Met Ser Ala Glu Asp Phe Asp Ala Ile Ile Ala Ala His
                2210                2215                2220

Phe Lys Pro Gly Asp Thr Val Leu Glu Thr Asp Ile Ala Ser Phe
                2225                2230                2235

Asp Lys Ser Gln Asp Asp Ser Leu Ala Leu Thr Ala Leu Met Leu
                2240                2245                2250
```

-continued

```
Leu Glu Asp Leu Gly Val Asp His Ser Leu Leu Asp Leu Ile Glu
    2255                2260                2265

Ala Ala Phe Gly Glu Ile Ser Ser Cys His Leu Pro Thr Gly Thr
    2270                2275                2280

Arg Phe Lys Phe Gly Ala Met Met Lys Ser Gly Met Phe Leu Thr
    2285                2290                2295

Leu Phe Val Asn Thr Leu Leu Asn Ile Thr Ile Ala Ser Arg Val
    2300                2305                2310

Leu Glu Asp Arg Leu Thr Lys Ser Ala Cys Ala Ala Phe Ile Gly
    2315                2320                2325

Asp Asp Asn Ile Ile His Gly Val Val Ser Asp Glu Leu Met Ala
    2330                2335                2340

Ala Arg Cys Ala Thr Trp Met Asn Met Glu Val Lys Ile Ile Asp
    2345                2350                2355

Ala Val Val Ser Gln Lys Ala Pro Tyr Phe Cys Gly Gly Phe Ile
    2360                2365                2370

Leu His Asp Ile Val Thr Gly Thr Ala Cys Arg Val Ala Asp Pro
    2375                2380                2385

Leu Lys Arg Leu Phe Lys Leu Gly Lys Pro Leu Ala Ala Gly Asp
    2390                2395                2400

Glu Gln Asp Glu Asp Arg Arg Arg Ala Leu Ala Asp Glu Val Val
    2405                2410                2415

Arg Trp Gln Arg Thr Gly Leu Ile Asp Glu Leu Glu Lys Ala Val
    2420                2425                2430

Tyr Ser Arg Tyr Glu Val Gln Gly Ile Ser Val Val Val Met Ser
    2435                2440                2445

Met Ala Thr Phe Ala Ser Ser Arg Ser Asn Phe Glu Lys Leu Arg
    2450                2455                2460

Gly Pro Val Val Thr Leu Tyr Gly Gly Pro Lys
    2465                2470

<210> SEQ ID NO 6
<211> LENGTH: 14
<212> TYPE: PRT
<213> ORGANISM: Chikungunya virus

<400> SEQUENCE: 6

Asn Glu Gly Glu Ile Glu Ser Leu Ser Ser Glu Leu Leu Thr
1               5                   10

<210> SEQ ID NO 7
<211> LENGTH: 20
<212> TYPE: PRT
<213> ORGANISM: Sindbis virus

<400> SEQUENCE: 7

Ser Asp Gly Glu Ile Asp Glu Leu Ser Arg Arg Val Thr Thr Glu Ser
1               5                   10                  15

Glu Pro Val Leu
            20

<210> SEQ ID NO 8
<211> LENGTH: 13
<212> TYPE: PRT
<213> ORGANISM: Semliki Forest virus

<400> SEQUENCE: 8
```

Asp Glu His Glu Val Asp Ala Leu Ala Ser Gly Ile Thr
1               5                   10

<210> SEQ ID NO 9
<211> LENGTH: 30
<212> TYPE: PRT
<213> ORGANISM: Chikungunya virus

<400> SEQUENCE: 9

Leu Pro Gly Glu Val Asp Asp Leu Thr Asp Ser Asp Trp Ser Thr Cys
1               5                   10                  15

Ser Asp Thr Asp Asp Glu Leu Arg Leu Asp Arg Ala Gly Gly
            20                  25                  30

<210> SEQ ID NO 10
<211> LENGTH: 33
<212> TYPE: PRT
<213> ORGANISM: Sindbis virus

<400> SEQUENCE: 10

Glu Pro Gly Glu Val Asn Ser Ile Ile Ser Ser Arg Ser Ala Val Ser
1               5                   10                  15

Phe Pro Leu Arg Lys Gln Arg Arg Arg Arg Ser Arg Arg Thr Glu
            20                  25                  30

Tyr

<210> SEQ ID NO 11
<211> LENGTH: 11
<212> TYPE: PRT
<213> ORGANISM: Semliki Forest virus

<400> SEQUENCE: 11

Asp Asp Val Leu Arg Leu Gly Arg Ala Gly Ala
1               5                   10

<210> SEQ ID NO 12
<211> LENGTH: 10
<212> TYPE: PRT
<213> ORGANISM: Venezuelan equine encephalitis virus

<400> SEQUENCE: 12

Leu His Glu Ala Gly Cys Ala Pro Ser Tyr
1               5                   10

<210> SEQ ID NO 13
<211> LENGTH: 10
<212> TYPE: PRT
<213> ORGANISM: Venezuelan equine encephalitis virus

<400> SEQUENCE: 13

Arg Phe Asp Ala Gly Ala Tyr Ile Phe Ser
1               5                   10

<210> SEQ ID NO 14
<211> LENGTH: 10
<212> TYPE: PRT
<213> ORGANISM: Eastern equine encephalomyelitis virus

<400> SEQUENCE: 14

Gln His Glu Ala Gly Arg Ala Pro Ala Tyr
1               5                   10

<210> SEQ ID NO 15

```
<211> LENGTH: 10
<212> TYPE: PRT
<213> ORGANISM: Eastern equine encephalomyelitis virus

<400> SEQUENCE: 15

Arg Tyr Glu Ala Gly Ala Tyr Ile Phe Ser
1               5                   10

<210> SEQ ID NO 16
<211> LENGTH: 10
<212> TYPE: PRT
<213> ORGANISM: Western equine encephalomyelitis virus

<400> SEQUENCE: 16

Arg Tyr Glu Ala Gly Arg Ala Pro Ala Tyr
1               5                   10

<210> SEQ ID NO 17
<211> LENGTH: 10
<212> TYPE: PRT
<213> ORGANISM: Western equine encephalomyelitis virus

<400> SEQUENCE: 17

Arg Tyr Glu Ala Gly Ala Tyr Ile Phe Ser
1               5                   10

<210> SEQ ID NO 18
<211> LENGTH: 4
<212> TYPE: PRT
<213> ORGANISM: Artificial Sequence
<220> FEATURE:
<223> OTHER INFORMATION: OW repeat motif

<400> SEQUENCE: 18

Phe Gly Asp Phe
1

<210> SEQ ID NO 19
<211> LENGTH: 4
<212> TYPE: PRT
<213> ORGANISM: Artificial Sequence
<220> FEATURE:
<223> OTHER INFORMATION: OW repeat motif

<400> SEQUENCE: 19

Phe Gly Ser Phe
1

<210> SEQ ID NO 20
<211> LENGTH: 8
<212> TYPE: PRT
<213> ORGANISM: Artificial Sequence
<220> FEATURE:
<223> OTHER INFORMATION: OW repeat motif

<400> SEQUENCE: 20

Phe Gly Asp Phe Phe Gly Asp Phe
1               5

<210> SEQ ID NO 21
<211> LENGTH: 8
<212> TYPE: PRT
<213> ORGANISM: Artificial Sequence
<220> FEATURE:
<223> OTHER INFORMATION: OW repeat motif

<400> SEQUENCE: 21
```

Phe Gly Ser Phe Phe Gly Ser Phe
1 5

<210> SEQ ID NO 22
<211> LENGTH: 8
<212> TYPE: PRT
<213> ORGANISM: Artificial Sequence
<220> FEATURE:
<223> OTHER INFORMATION: OW repeat motif

<400> SEQUENCE: 22

Phe Gly Asp Phe Phe Gly Ser Phe
1 5

<210> SEQ ID NO 23
<211> LENGTH: 8
<212> TYPE: PRT
<213> ORGANISM: Artificial Sequence
<220> FEATURE:
<223> OTHER INFORMATION: OW repeat motif

<400> SEQUENCE: 23

Phe Gly Ser Phe Phe Gly Asp Phe
1 5

<210> SEQ ID NO 24
<211> LENGTH: 482
<212> TYPE: PRT
<213> ORGANISM: Semliki Forest virus

<400> SEQUENCE: 24

Ala Pro Ser Tyr Arg Val Lys Arg Ala Asp Ile Ala Thr Cys Thr Glu
1 5 10 15

Ala Ala Val Val Asn Ala Ala Asn Ala Arg Gly Thr Val Gly Asp Gly
20 25 30

Val Cys Arg Ala Val Ala Lys Lys Trp Pro Ser Ala Phe Lys Gly Ala
35 40 45

Ala Thr Pro Val Gly Thr Ile Lys Thr Val Met Cys Gly Ser Tyr Pro
50 55 60

Val Ile His Ala Val Ala Pro Asn Phe Ser Ala Thr Thr Glu Ala Glu
65 70 75 80

Gly Asp Arg Glu Leu Ala Ala Val Tyr Arg Ala Val Ala Ala Glu Val
85 90 95

Asn Arg Leu Ser Leu Ser Ser Val Ala Ile Pro Leu Leu Ser Thr Gly
100 105 110

Val Phe Ser Gly Gly Arg Asp Arg Leu Gln Gln Ser Leu Asn His Leu
115 120 125

Phe Thr Ala Met Asp Ala Thr Asp Ala Asp Val Thr Ile Tyr Cys Arg
130 135 140

Asp Lys Ser Trp Glu Lys Lys Ile Gln Glu Ala Ile Asp Met Arg Thr
145 150 155 160

Ala Val Glu Leu Leu Asn Asp Asp Val Glu Leu Thr Thr Asp Leu Val
165 170 175

Arg Val His Pro Asp Ser Ser Leu Val Gly Arg Lys Gly Tyr Ser Thr
180 185 190

Thr Asp Gly Ser Leu Tyr Ser Tyr Phe Glu Gly Thr Lys Phe Asn Gln
195 200 205

Ala Ala Ile Asp Met Ala Glu Ile Leu Thr Leu Trp Pro Arg Leu Gln
210 215 220

Glu Ala Asn Glu Arg Ile Cys Leu Tyr Ala Leu Gly Glu Thr Met Asp
225 230 235 240

Asn Ile Gly Ser Lys Cys Pro Val Asn Asp Ser Asp Ser Ser Thr Pro
245 250 255

Pro Arg Thr Val Pro Cys Leu Cys Arg Tyr Ala Met Thr Ala Glu Arg
260 265 270

Ile Ala Arg Leu Arg Ser His Gln Val Lys Ser Met Val Val Cys Ser
275 280 285

Ser Phe Pro Leu Pro Lys Tyr His Val Asp Gly Val Gln Lys Val Lys
290 295 300

Cys Glu Lys Val Leu Leu Phe Asp Pro Thr Val Pro Ser Val Val Ser
305 310 315 320

Pro Arg Lys Tyr Ala Ala Ser Thr Thr Asp His Ser Asp Arg Ser Leu
325 330 335

Arg Gly Phe Asp Leu Asp Trp Thr Thr Asp Ser Ser Ser Thr Ala Ser
340 345 350

Asp Thr Met Ser Leu Pro Ser Leu Gln Ser Cys Asp Ile Asp Ser Ile
355 360 365

Tyr Glu Pro Met Ala Pro Ile Val Val Thr Ala Asp Val His Pro Glu
370 375 380

Pro Ala Gly Ile Ala Asp Leu Ala Ala Asp Val His Pro Glu Pro Ala
385 390 395 400

Asp His Val Asp Leu Glu Asn Pro Ile Pro Pro Pro Arg Pro Lys Arg
405 410 415

Ala Ala Tyr Leu Ala Ser Arg Ala Ala Glu Arg Pro Val Pro Ala Pro
420 425 430

Arg Lys Pro Thr Pro Ala Pro Arg Thr Ala Phe Arg Asn Lys Leu Pro
435 440 445

Leu Thr Phe Gly Asp Phe Asp Glu His Glu Val Asp Ala Leu Ala Ser
450 455 460

Gly Ile Thr Phe Gly Asp Phe Asp Asp Val Leu Arg Leu Gly Arg Ala
465 470 475 480

Gly Ala

<210> SEQ ID NO 25
<211> LENGTH: 549
<212> TYPE: PRT
<213> ORGANISM: Sindbis virus

<400> SEQUENCE: 25

Ala Pro Ser Tyr Arg Thr Lys Arg Glu Asn Ile Ala Asp Cys Gln Glu
1 5 10 15

Glu Ala Val Val Asn Ala Ala Asn Pro Leu Gly Arg Pro Gly Glu Gly
20 25 30

Val Cys Arg Ala Ile Tyr Lys Arg Trp Pro Thr Ser Phe Thr Asp Ser
35 40 45

Ala Thr Glu Thr Gly Thr Ala Arg Met Thr Val Cys Leu Gly Lys Lys
50 55 60

Val Ile His Ala Val Gly Pro Asp Phe Arg Lys His Pro Glu Ala Glu
65 70 75 80

Ala Leu Lys Leu Leu Gln Asn Ala Tyr His Ala Val Ala Asp Leu Val
85 90 95

Asn Glu His Asn Ile Lys Ser Val Ala Ile Pro Leu Leu Ser Thr Gly
100 105 110

```
Ile Tyr Ala Ala Gly Lys Asp Arg Leu Glu Val Ser Leu Asn Cys Leu
            115                 120                 125

Thr Thr Ala Leu Asp Arg Thr Asp Ala Asp Val Thr Ile Tyr Cys Leu
130                 135                 140

Asp Lys Lys Trp Lys Glu Arg Ile Asp Ala Ala Leu Gln Leu Lys Glu
145                 150                 155                 160

Ser Val Thr Glu Leu Lys Asp Glu Asp Met Glu Ile Asp Asp Glu Leu
                165                 170                 175

Val Trp Ile His Pro Asp Ser Cys Leu Lys Gly Arg Lys Gly Phe Ser
            180                 185                 190

Thr Thr Lys Gly Lys Leu Tyr Ser Tyr Phe Glu Gly Thr Lys Phe His
            195                 200                 205

Gln Ala Ala Lys Asp Met Ala Glu Ile Lys Val Leu Phe Pro Asn Asp
            210                 215                 220

Gln Glu Ser Asn Glu Gln Leu Cys Ala Tyr Ile Leu Gly Glu Thr Met
225                 230                 235                 240

Glu Ala Ile Arg Glu Lys Cys Pro Val Asp His Asn Pro Ser Ser Ser
                245                 250                 255

Pro Pro Lys Thr Leu Pro Cys Leu Cys Met Tyr Ala Met Thr Pro Glu
            260                 265                 270

Arg Val His Arg Leu Arg Ser Asn Asn Val Lys Glu Val Thr Val Cys
            275                 280                 285

Ser Ser Thr Pro Leu Pro Lys His Lys Ile Lys Asn Val Gln Lys Val
            290                 295                 300

Gln Cys Thr Lys Val Val Leu Phe Asn Pro His Thr Pro Ala Phe Val
305                 310                 315                 320

Pro Ala Arg Lys Tyr Ile Glu Val Pro Glu Gln Pro Thr Ala Pro Pro
                325                 330                 335

Ala Gln Ala Glu Glu Ala Pro Glu Val Val Ala Thr Pro Ser Pro Ser
            340                 345                 350

Thr Ala Asp Asn Thr Ser Leu Asp Val Thr Asp Ile Ser Leu Asp Met
            355                 360                 365

Asp Asp Ser Ser Glu Gly Ser Leu Phe Ser Ser Phe Ser Gly Ser Asp
            370                 375                 380

Asn Ser Ile Thr Ser Met Asp Ser Trp Ser Ser Gly Pro Ser Ser Leu
385                 390                 395                 400

Glu Ile Val Asp Arg Arg Gln Val Val Ala Asp Val His Ala Val
                405                 410                 415

Gln Glu Pro Ala Pro Ile Pro Pro Arg Leu Lys Lys Met Ala Arg
            420                 425                 430

Leu Ala Ala Ala Arg Lys Glu Pro Thr Pro Pro Ala Ser Asn Ser Ser
            435                 440                 445

Glu Ser Leu His Leu Ser Phe Gly Gly Val Ser Met Ser Leu Gly Ser
            450                 455                 460

Ile Phe Asp Gly Glu Thr Ala Arg Gln Ala Ala Val Gln Pro Leu Ala
465                 470                 475                 480

Thr Gly Pro Thr Asp Val Pro Met Ser Phe Gly Ser Phe Ser Asp Gly
                485                 490                 495

Glu Ile Asp Glu Leu Ser Arg Arg Val Thr Glu Ser Glu Pro Val Leu
            500                 505                 510

Phe Gly Ser Phe Glu Pro Gly Val Asn Ser Ile Ile Ser Ser Arg
            515                 520                 525
```

-continued

Ser Ala Val Ser Phe Pro Leu Arg Lys Gln Arg Arg Arg Arg Ser
            530                 535                 540

Arg Arg Thr Glu Tyr
545

<210> SEQ ID NO 26
<211> LENGTH: 530
<212> TYPE: PRT
<213> ORGANISM: Chikungunya virus

<400> SEQUENCE: 26

Ala Pro Ser Tyr Arg Val Lys Arg Met Asp Ile Ala Lys Asn Asp Glu
1               5                   10                  15

Glu Cys Val Val Asn Ala Ala Asn Pro Arg Gly Leu Pro Gly Asp Gly
            20                  25                  30

Val Cys Lys Ala Val Tyr Lys Lys Trp Pro Glu Ser Phe Lys Asn Ser
        35                  40                  45

Ala Thr Pro Val Gly Thr Ala Lys Thr Val Met Cys Gly Thr Tyr Pro
    50                  55                  60

Val Ile His Ala Val Gly Pro Asn Phe Ser Asn Tyr Ser Glu Ser Glu
65                  70                  75                  80

Gly Asp Arg Glu Leu Ala Ala Ala Tyr Arg Glu Val Ala Lys Glu Val
                85                  90                  95

Thr Arg Leu Gly Val Asn Ser Val Ala Ile Pro Leu Leu Ser Thr Gly
            100                 105                 110

Val Tyr Ser Gly Gly Lys Asp Arg Leu Thr Gln Ser Leu Asn His Leu
        115                 120                 125

Phe Thr Ala Met Asp Ser Thr Asp Ala Asp Val Val Ile Tyr Cys Arg
    130                 135                 140

Asp Lys Glu Trp Glu Lys Lys Ile Ser Glu Ala Ile Gln Met Arg Thr
145                 150                 155                 160

Gln Val Glu Leu Leu Asp Glu His Ile Ser Ile Asp Cys Asp Val Val
                165                 170                 175

Arg Val His Pro Asp Ser Ser Leu Ala Gly Arg Lys Gly Tyr Ser Thr
            180                 185                 190

Thr Glu Gly Ala Leu Tyr Ser Tyr Leu Glu Gly Thr Arg Phe His Gln
        195                 200                 205

Thr Ala Val Asp Met Ala Glu Ile Tyr Thr Met Trp Pro Lys Gln Thr
    210                 215                 220

Glu Ala Asn Glu Gln Val Cys Leu Tyr Ala Leu Gly Glu Ser Ile Glu
225                 230                 235                 240

Ser Ile Arg Gln Lys Cys Pro Val Asp Asp Ala Asp Ala Ser Ser Pro
                245                 250                 255

Pro Lys Thr Val Pro Cys Leu Cys Arg Tyr Ala Met Thr Pro Glu Arg
            260                 265                 270

Val Thr Arg Leu Arg Met Asn His Val Thr Ser Ile Ile Val Cys Ser
        275                 280                 285

Ser Phe Pro Leu Pro Lys Tyr Lys Ile Glu Gly Val Gln Lys Val Lys
    290                 295                 300

Cys Ser Lys Val Met Leu Phe Asp His Asn Val Pro Ser Arg Val Ser
305                 310                 315                 320

Pro Arg Glu Tyr Arg Pro Ser Gln Glu Ser Val Gln Glu Ala Ser Thr
                325                 330                 335

Thr Thr Ser Leu Thr His Ser Gln Phe Asp Leu Ser Val Asp Gly Lys
            340                 345                 350

```
Ile Leu Pro Val Pro Ser Asp Leu Asp Ala Asp Ala Pro Ala Leu Glu
            355                 360                 365

Pro Ala Leu Asp Asp Gly Ala Ile His Thr Leu Pro Ser Ala Thr Gly
    370                 375                 380

Asn Leu Ala Ala Val Ser Asp Trp Val Met Ser Thr Val Pro Val Ala
385                 390                 395                 400

Pro Pro Arg Arg Arg Gly Arg Asn Leu Thr Val Thr Cys Asp Glu
            405                 410                 415

Arg Glu Gly Asn Ile Thr Pro Met Ala Ser Val Arg Phe Phe Arg Ala
            420                 425                 430

Glu Leu Cys Pro Val Val Gln Glu Thr Ala Thr Arg Asp Thr Ala
            435                 440                 445

Met Ser Leu Gln Ala Pro Pro Ser Thr Ala Thr Glu Leu Ser His Pro
    450                 455                 460

Pro Ile Ser Phe Gly Ala Pro Ser Glu Thr Phe Pro Ile Thr Phe Gly
465                 470                 475                 480

Asp Phe Asn Glu Gly Glu Ile Glu Ser Leu Ser Ser Glu Leu Leu Thr
                485                 490                 495

Phe Gly Asp Phe Leu Pro Gly Glu Val Asp Asp Leu Thr Asp Ser Asp
            500                 505                 510

Trp Ser Thr Cys Ser Asp Thr Asp Asp Glu Leu Arg Leu Asp Arg Ala
            515                 520                 525

Gly Gly
    530

<210> SEQ ID NO 27
<211> LENGTH: 556
<212> TYPE: PRT
<213> ORGANISM: Venezuelan equine encephalitis virus

<400> SEQUENCE: 27

Ala Pro Ser Tyr His Val Val Arg Gly Asp Ile Ala Thr Ala Thr Glu
1               5                   10                  15

Gly Val Ile Ile Asn Ala Ala Asn Ser Lys Gly Gln Pro Gly Gly Gly
            20                  25                  30

Val Cys Gly Ala Leu Tyr Lys Lys Phe Pro Glu Ser Phe Asp Leu Gln
            35                  40                  45

Pro Ile Glu Val Gly Lys Ala Arg Leu Val Lys Gly Ala Ala Lys His
    50                  55                  60

Ile Ile His Ala Val Gly Pro Asn Phe Asn Lys Val Ser Glu Val Glu
65                  70                  75                  80

Gly Asp Lys Gln Leu Ala Glu Ala Tyr Glu Ser Ile Ala Lys Ile Val
                85                  90                  95

Asn Asp Asn Asn Tyr Lys Ser Val Ala Ile Pro Leu Leu Ser Thr Gly
            100                 105                 110

Ile Phe Ser Gly Asn Lys Asp Arg Leu Thr Gln Ser Leu Asn His Leu
            115                 120                 125

Leu Thr Ala Leu Asp Thr Thr Asp Ala Asp Val Ala Ile Tyr Cys Arg
    130                 135                 140

Asp Lys Lys Trp Glu Met Thr Leu Lys Glu Ala Val Ala Arg Arg Glu
145                 150                 155                 160

Ala Val Glu Glu Ile Cys Ile Ser Asp Asp Ser Ser Val Thr Glu Pro
                165                 170                 175

Asp Ala Glu Leu Val Arg Val His Pro Lys Ser Ser Leu Ala Gly Arg
```

180                 185                 190
Lys Gly Tyr Ser Thr Ser Asp Gly Lys Thr Phe Ser Tyr Leu Glu Gly
            195                 200                 205

Thr Lys Phe His Gln Ala Ala Lys Asp Ile Ala Glu Ile Asn Ala Met
        210                 215                 220

Trp Pro Val Ala Thr Glu Ala Asn Glu Gln Val Cys Met Tyr Ile Leu
225                 230                 235                 240

Gly Glu Ser Met Ser Ser Ile Arg Ser Lys Cys Pro Val Glu Ser
            245                 250                 255

Glu Ala Ser Thr Pro Pro Ser Thr Leu Pro Cys Leu Cys Ile His Ala
        260                 265                 270

Met Thr Pro Glu Arg Val Gln Arg Leu Lys Ala Ser Arg Pro Glu Gln
        275                 280                 285

Ile Thr Val Cys Ser Ser Phe Pro Leu Pro Lys Tyr Arg Ile Thr Gly
        290                 295                 300

Val Gln Lys Ile Gln Cys Ser Gln Pro Ile Leu Phe Ser Pro Lys Val
305                 310                 315                 320

Pro Ala Tyr Ile His Pro Arg Lys Tyr Leu Val Glu Thr Pro Pro Val
            325                 330                 335

Asp Glu Thr Pro Glu Pro Ser Ala Glu Asn Gln Ser Thr Glu Gly Thr
        340                 345                 350

Pro Glu Gln Pro Pro Leu Ile Thr Glu Asp Glu Thr Arg Thr Arg Thr
        355                 360                 365

Pro Glu Pro Ile Ile Ile Glu Glu Glu Glu Asp Ser Ile Ser Leu
        370                 375                 380

Leu Ser Asp Gly Pro Thr His Gln Val Leu Gln Val Glu Ala Asp Ile
385                 390                 395                 400

His Gly Pro Pro Ser Val Ser Ser Ser Trp Ser Ile Pro His Ala
            405                 410                 415

Ser Asp Phe Asp Val Asp Ser Leu Ser Ile Leu Asp Thr Leu Glu Gly
        420                 425                 430

Ala Ser Val Thr Ser Gly Ala Thr Ser Ala Glu Thr Asn Ser Tyr Phe
        435                 440                 445

Ala Lys Ser Met Glu Phe Leu Ala Arg Pro Val Pro Ala Pro Arg Thr
        450                 455                 460

Val Phe Arg Asn Pro Pro His Pro Ala Pro Arg Thr Arg Thr Pro Ser
465                 470                 475                 480

Leu Ala Pro Ser Arg Ala Cys Ser Arg Thr Ser Leu Val Ser Thr Pro
            485                 490                 495

Pro Gly Val Asn Arg Val Ile Thr Arg Glu Glu Leu Glu Ala Leu Thr
        500                 505                 510

Pro Ser Arg Thr Pro Ser Arg Ser Val Ser Arg Thr Ser Leu Val Ser
        515                 520                 525

Asn Pro Pro Gly Val Asn Arg Val Ile Thr Arg Glu Glu Phe Glu Ala
        530                 535                 540

Phe Val Ala Gln Gln Gln Arg Phe Asp Ala Gly Ala
545                 550                 555

<210> SEQ ID NO 28
<211> LENGTH: 552
<212> TYPE: PRT
<213> ORGANISM: Eastern equine encephalomyelitis virus

<400> SEQUENCE: 28

```
Ala Pro Ala Tyr Arg Val Val Arg Gly Asp Ile Thr Lys Ser Asn Asp
 1               5                  10                 15

Glu Val Ile Val Asn Ala Ala Asn Asn Lys Gly Gln Pro Gly Ser Gly
                20                  25                 30

Val Cys Gly Ala Leu Tyr Arg Lys Trp Pro Gly Ala Phe Asp Lys Gln
            35                  40                  45

Pro Val Ala Thr Gly Lys Ala His Leu Val Lys His Ser Pro Asn Val
        50                  55                  60

Ile His Ala Val Gly Pro Asn Phe Ser Arg Leu Ser Glu Asn Glu Gly
 65                 70                  75                  80

Asp Gln Lys Leu Ser Glu Val Tyr Met Asp Ile Ala Arg Ile Ile Asn
                85                  90                  95

Asn Glu Arg Phe Thr Lys Val Ser Ile Pro Leu Leu Ser Thr Gly Ile
               100                 105                 110

Tyr Ala Gly Gly Lys Asp Arg Val Met Gln Ser Leu Asn His Leu Phe
            115                 120                 125

Thr Ala Met Asp Thr Thr Asp Ala Asp Ile Thr Ile Tyr Cys Leu Asp
        130                 135                 140

Lys Gln Trp Glu Ser Arg Ile Lys Glu Ala Ile Thr Arg Lys Glu Ser
145                 150                 155                 160

Val Glu Glu Leu Thr Glu Asp Arg Pro Val Asp Ile Glu Leu Val
                165                 170                 175

Arg Val His Pro Leu Ser Ser Leu Ala Gly Arg Pro Gly Tyr Ser Thr
                180                 185                 190

Thr Glu Gly Lys Val Tyr Ser Tyr Leu Glu Gly Thr Arg Phe His Gln
            195                 200                 205

Thr Ala Lys Asp Ile Ala Glu Ile Tyr Ala Met Trp Pro Asn Lys Gln
        210                 215                 220

Glu Ala Asn Glu Gln Ile Cys Leu Tyr Val Leu Gly Glu Ser Met Asn
225                 230                 235                 240

Ser Ile Arg Ser Lys Cys Pro Val Glu Ser Glu Ala Ser Ser Pro
                245                 250                 255

Pro His Thr Ile Pro Cys Leu Cys Asn Tyr Ala Met Thr Ala Glu Arg
            260                 265                 270

Val Tyr Arg Leu Arg Met Ala Lys Asn Glu Gln Phe Ala Val Cys Ser
        275                 280                 285

Ser Phe Gln Leu Pro Lys Tyr Arg Ile Thr Gly Val Gln Lys Ile Gln
            290                 295                 300

Cys Ser Lys Pro Val Ile Phe Ser Gly Thr Val Pro Ala Ile His
305                 310                 315                 320

Pro Arg Lys Phe Ala Ser Val Thr Val Glu Asp Thr Pro Val Val Gln
                325                 330                 335

Pro Glu Arg Leu Val Pro Arg Arg Pro Ala Pro Pro Val Pro
                340                 345                 350

Ala Arg Ile Pro Ser Pro Cys Thr Ser Thr Asn Gly Ser Thr Thr
                355                 360                 365

Ser Ile Gln Ser Leu Gly Glu Asp Gln Ser Ala Ser Ala Ser Ser Gly
    370                 375                 380

Ala Glu Ile Ser Val Asp Gln Val Ser Leu Trp Ser Ile Pro Ser Ala
385                 390                 395                 400

Thr Gly Phe Asp Val Arg Thr Ser Ser Ser Leu Ser Leu Glu Gln Pro
                405                 410                 415

Thr Phe Pro Thr Met Val Val Glu Ala Glu Ile His Ala Ser Gln Gly
```

```
              420                 425                 430
Ser Leu Trp Ser Ile Pro Ser Ile Thr Gly Ser Glu Thr Arg Ala Pro
        435                 440                 445

Ser Pro Pro Ser Gln Asp Ser Arg Pro Ser Thr Pro Ser Ala Ser Gly
    450                 455                 460

Ser His Thr Ser Val Asp Leu Ile Thr Phe Asp Ser Val Ala Glu Ile
465                 470                 475                 480

Leu Glu Asp Phe Ser Arg Ser Pro Phe Gln Phe Leu Ser Glu Ile Lys
                485                 490                 495

Pro Ile Pro Ala Pro Arg Thr Arg Val Asn Asn Met Ser Arg Ser Ala
            500                 505                 510

Asp Thr Ile Lys Pro Ile Pro Lys Pro Arg Lys Cys Gln Val Lys Tyr
        515                 520                 525

Thr Gln Pro Pro Gly Val Ala Arg Val Ile Ser Ala Ala Glu Phe Asp
    530                 535                 540

Glu Phe Val Arg Arg His Ser Asn
545                 550

<210> SEQ ID NO 29
<211> LENGTH: 532
<212> TYPE: PRT
<213> ORGANISM: Western equine encephalomyelitis virus
<220> FEATURE:
<221> NAME/KEY: misc_feature
<222> LOCATION: (526)..(526)
<223> OTHER INFORMATION: Xaa can be any naturally occurring amino acid

<400> SEQUENCE: 29

Ala Pro Ala Tyr Arg Val Ile Arg Gly Asp Ile Ser Lys Ser Ala Asp
1               5                   10                  15

Gln Ala Ile Val Asn Ala Ala Asn Ser Lys Gly Gln Pro Gly Ser Gly
            20                  25                  30

Val Cys Gly Ala Leu Tyr Arg Lys Trp Pro Ala Ala Phe Asp Arg Gln
        35                  40                  45

Pro Ile Ala Val Gly Thr Ala Arg Leu Val Lys His Glu Pro Leu Ile
    50                  55                  60

Ile His Ala Val Gly Pro Asn Phe Ser Lys Met Pro Glu Pro Glu Gly
65                  70                  75                  80

Asp Leu Lys Leu Ala Ala Ala Tyr Met Ser Ile Ala Ser Ile Val Asn
                85                  90                  95

Ala Glu Arg Ile Thr Lys Ile Ser Val Pro Leu Leu Ser Thr Gly Ile
            100                 105                 110

Tyr Ser Gly Gly Lys Asp Arg Val Met Gln Ser Leu His His Leu Phe
        115                 120                 125

Thr Ala Phe Asp Thr Thr Asp Ala Asp Val Thr Ile Tyr Cys Leu Asp
    130                 135                 140

Lys Gln Trp Glu Thr Arg Ile Ile Glu Ala Ile His Arg Lys Glu Ser
145                 150                 155                 160

Val Glu Ile Leu Asp Asp Asp Lys Pro Val Asp Ile Asp Leu Val Arg
                165                 170                 175

Val His Pro Asn Ser Ser Leu Ala Gly Arg Pro Gly Tyr Ser Val Asn
            180                 185                 190

Glu Gly Lys Leu Tyr Ser Tyr Leu Glu Gly Thr Arg Phe His Gln Thr
        195                 200                 205

Ala Lys Asp Ile Ala Glu Ile His Ala Met Trp Pro Asn Lys Ser Glu
    210                 215                 220
```

Ala Asn Glu Gln Ile Cys Leu Tyr Ile Leu Gly Glu Ser Met Ser Ser
225                 230                 235                 240

Ile Arg Ser Lys Cys Pro Val Glu Glu Ser Glu Ala Ser Ala Pro Pro
                245                 250                 255

His Thr Leu Pro Cys Leu Cys Asn Tyr Ala Met Thr Ala Glu Arg Val
                260                 265                 270

Tyr Arg Leu Arg Ser Ala Lys Lys Glu Gln Phe Ala Val Cys Ser Ser
                275                 280                 285

Phe Leu Leu Pro Lys Tyr Arg Ile Thr Gly Val Gln Lys Leu Gln Cys
                290                 295                 300

Ser Lys Pro Val Leu Phe Ser Gly Val Val Pro Ala Val His Pro
305                 310                 315                 320

Arg Lys Tyr Ala Glu Ile Ile Leu Glu Thr Pro Pro Pro Ala Thr
                325                 330                 335

Thr Thr Val Ile Cys Glu Pro Thr Val Pro Glu Arg Ile Pro Ser Pro
                340                 345                 350

Val Ile Ser Arg Ala Pro Ser Ala Glu Ser Leu Leu Ser Leu Gly Gly
                355                 360                 365

Val Ser Phe Ser Ser Ala Thr Arg Ser Ser Thr Ala Trp Ser Asp
370                 375                 380

Tyr Asp Arg Arg Phe Val Val Thr Ala Asp Val His Gln Ala Asn Thr
385                 390                 395                 400

Ser Thr Trp Ser Ile Pro Ser Ala Pro Gly Leu Asp Val Gln Leu Pro
                405                 410                 415

Ser Asp Val Thr Asp Ser His Trp Ser Ile Pro Ser Ala Ser Gly Phe
                420                 425                 430

Glu Val Arg Thr Pro Ser Val Gln Asp Leu Thr Ala Glu Cys Ala Lys
                435                 440                 445

Pro Arg Gly Leu Ala Glu Ile Met Gln Asp Phe Asn Thr Ala Pro Phe
                450                 455                 460

Gln Phe Leu Ser Asp Tyr Arg Pro Val Pro Ala Pro Arg Arg Arg Pro
465                 470                 475                 480

Ile Pro Ser Pro Arg Ser Thr Ala Ser Ala Pro Pro Val Pro Lys Pro
                485                 490                 495

Arg Arg Thr Lys Tyr Gln Gln Pro Pro Gly Val Ala Arg Ala Ile Ser
                500                 505                 510

Glu Ala Glu Leu Asp Glu Tyr Ile Arg Gln His Ser Asn Xaa Arg Tyr
                515                 520                 525

Glu Ala Gly Ala
                530

<210> SEQ ID NO 30
<211> LENGTH: 555
<212> TYPE: PRT
<213> ORGANISM: Artificial Sequence
<220> FEATURE:
<223> OTHER INFORMATION: VEEV/CHIKV nsP3 chimera

<400> SEQUENCE: 30

Ala Pro Ser Tyr His Val Val Arg Gly Asp Ile Ala Thr Ala Thr Glu
1               5                   10                  15

Gly Val Ile Ile Asn Ala Ala Asn Ser Lys Gly Gln Pro Gly Gly Gly
                20                  25                  30

Val Cys Gly Ala Leu Tyr Lys Lys Phe Pro Glu Ser Phe Asp Leu Gln
                35                  40                  45

-continued

```
Pro Ile Glu Val Gly Lys Ala Arg Leu Val Lys Gly Ala Ala Lys His
    50                  55                  60
Ile Ile His Ala Val Gly Pro Asn Phe Asn Lys Val Ser Glu Val Glu
65                  70                  75                  80
Gly Asp Lys Gln Leu Ala Glu Ala Tyr Glu Ser Ile Ala Lys Ile Val
                85                  90                  95
Asn Asp Asn Asn Tyr Lys Ser Val Ala Ile Pro Leu Leu Ser Thr Gly
                100                 105                 110
Ile Phe Ser Gly Asn Lys Asp Arg Leu Thr Gln Ser Leu Asn His Leu
            115                 120                 125
Leu Thr Ala Leu Asp Thr Thr Asp Ala Asp Val Ala Ile Tyr Cys Arg
    130                 135                 140
Asp Lys Lys Trp Glu Met Thr Leu Lys Glu Ala Val Ala Arg Arg Glu
145                 150                 155                 160
Ala Val Glu Glu Ile Cys Ile Ser Asp Asp Ser Val Thr Glu Pro
                165                 170                 175
Asp Ala Glu Leu Val Arg Val His Pro Lys Ser Ser Leu Ala Gly Arg
            180                 185                 190
Lys Gly Tyr Ser Thr Ser Asp Gly Lys Thr Phe Ser Tyr Leu Glu Gly
    195                 200                 205
Thr Lys Phe His Gln Ala Ala Lys Asp Ile Ala Glu Ile Asn Ala Met
    210                 215                 220
Trp Pro Val Ala Thr Glu Ala Asn Glu Gln Val Cys Met Tyr Ile Leu
225                 230                 235                 240
Gly Glu Ser Met Ser Ser Ile Arg Ser Lys Cys Pro Val Glu Glu Ser
                245                 250                 255
Glu Ala Ser Thr Pro Pro Ser Thr Leu Pro Cys Leu Cys Ile His Ala
                260                 265                 270
Met Thr Pro Glu Arg Val Gln Arg Leu Lys Ala Ser Arg Pro Glu Gln
            275                 280                 285
Ile Thr Val Cys Ser Ser Phe Pro Leu Pro Lys Tyr Arg Ile Thr Gly
    290                 295                 300
Val Gln Lys Ile Gln Cys Ser Gln Pro Ile Leu Phe Ser Pro Lys Val
305                 310                 315                 320
Pro Ala Tyr Ile His Pro Arg Lys Tyr Leu Val Glu Thr Pro Ser Thr
                325                 330                 335
Thr Thr Ser Leu Thr His Ser Gln Phe Asp Leu Ser Val Asp Gly Lys
            340                 345                 350
Ile Leu Pro Val Pro Ser Asp Leu Asp Ala Asp Ala Pro Ala Leu Glu
    355                 360                 365
Pro Ala Leu Asp Asp Gly Ala Ile His Thr Leu Pro Ser Ala Thr Gly
    370                 375                 380
Asn Leu Ala Ala Val Ser Asp Trp Val Met Ser Thr Val Pro Val Ala
385                 390                 395                 400
Pro Pro Arg Arg Arg Gly Arg Asn Leu Thr Val Thr Cys Asp Glu
                405                 410                 415
Arg Glu Gly Asn Ile Thr Pro Met Ala Ser Val Arg Phe Phe Arg Ala
            420                 425                 430
Glu Leu Cys Pro Val Val Gln Glu Thr Ala Glu Thr Arg Asp Thr Ala
    435                 440                 445
Met Ser Leu Gln Ala Pro Pro Ser Thr Ala Thr Glu Leu Ser His Pro
    450                 455                 460
```

```
Pro Ile Ser Phe Gly Ala Pro Ser Glu Thr Phe Pro Ile Thr Phe Gly
465                 470                 475                 480

Asp Phe Asn Glu Gly Glu Ile Glu Ser Leu Ser Ser Glu Leu Leu Thr
            485                 490                 495

Phe Gly Asp Phe Leu Pro Gly Glu Val Asp Asp Leu Thr Asp Ser Asp
            500                 505                 510

Trp Ser Thr Cys Ser Arg Ser Val Ser Arg Thr Ser Leu Val Ser Asn
            515                 520                 525

Pro Pro Gly Val Asn Arg Val Ile Thr Arg Glu Glu Phe Glu Ala Phe
            530                 535                 540

Val Ala Gln Gln Gln Arg Phe Asp Ala Gly Ala
545                 550                 555

<210> SEQ ID NO 31
<211> LENGTH: 556
<212> TYPE: PRT
<213> ORGANISM: Artificial Sequence
<220> FEATURE:
<223> OTHER INFORMATION: VEEV/SINV nsP3 chimera

<400> SEQUENCE: 31

Ala Pro Ser Tyr His Val Val Arg Gly Asp Ile Ala Thr Ala Thr Glu
1               5                   10                  15

Gly Val Ile Ile Asn Ala Ala Asn Ser Lys Gly Gln Pro Gly Gly Gly
            20                  25                  30

Val Cys Gly Ala Leu Tyr Lys Lys Phe Pro Glu Ser Phe Asp Leu Gln
            35                  40                  45

Pro Ile Glu Val Gly Lys Ala Arg Leu Val Lys Gly Ala Ala Lys His
        50                  55                  60

Ile Ile His Ala Val Gly Pro Asn Phe Asn Lys Val Ser Glu Val Glu
65                  70                  75                  80

Gly Asp Lys Gln Leu Ala Glu Ala Tyr Glu Ser Ile Ala Lys Ile Val
                85                  90                  95

Asn Asp Asn Asn Tyr Lys Ser Val Ala Ile Pro Leu Leu Ser Thr Gly
            100                 105                 110

Ile Phe Ser Gly Asn Lys Asp Arg Leu Thr Gln Ser Leu Asn His Leu
        115                 120                 125

Leu Thr Ala Leu Asp Thr Thr Asp Ala Asp Val Ala Ile Tyr Cys Arg
130                 135                 140

Asp Lys Lys Trp Glu Met Thr Leu Lys Glu Ala Val Ala Arg Arg Glu
145                 150                 155                 160

Ala Val Glu Glu Ile Cys Ile Ser Asp Asp Ser Ser Val Thr Glu Pro
                165                 170                 175

Asp Ala Glu Leu Val Arg Val His Pro Lys Ser Ser Leu Ala Gly Arg
            180                 185                 190

Lys Gly Tyr Ser Thr Ser Asp Gly Lys Thr Phe Ser Tyr Leu Glu Gly
        195                 200                 205

Thr Lys Phe His Gln Ala Ala Lys Asp Ile Ala Glu Ile Asn Ala Met
210                 215                 220

Trp Pro Val Ala Thr Glu Ala Asn Glu Gln Val Cys Met Tyr Ile Leu
225                 230                 235                 240

Gly Glu Ser Met Ser Ser Ile Arg Ser Lys Cys Pro Val Glu Glu Ser
                245                 250                 255

Glu Ala Ser Thr Pro Pro Ser Thr Leu Pro Cys Leu Cys Ile His Ala
            260                 265                 270
```

```
Met Thr Pro Glu Arg Val Gln Arg Leu Lys Ala Ser Arg Pro Glu Gln
        275                 280                 285

Ile Thr Val Cys Ser Ser Phe Pro Leu Pro Lys Tyr Arg Ile Thr Gly
    290                 295                 300

Val Gln Lys Ile Gln Cys Ser Gln Pro Ile Leu Phe Ser Pro Lys Val
305                 310                 315                 320

Pro Ala Tyr Ile His Pro Arg Lys Tyr Leu Val Glu Thr Pro Pro Pro
                325                 330                 335

Ala Gln Ala Glu Glu Ala Pro Glu Val Val Ala Thr Pro Ser Pro Ser
            340                 345                 350

Thr Ala Asp Asn Thr Ser Leu Asp Val Thr Asp Ile Ser Leu Asp Met
        355                 360                 365

Asp Asp Ser Ser Glu Gly Ser Leu Phe Ser Ser Phe Ser Gly Ser Asp
    370                 375                 380

Asn Ser Ile Thr Ser Met Asp Ser Trp Ser Ser Gly Pro Ser Ser Leu
385                 390                 395                 400

Glu Ile Val Asp Arg Arg Gln Val Val Val Ala Asp Val His Ala Val
                405                 410                 415

Gln Glu Pro Ala Pro Ile Pro Pro Arg Leu Lys Lys Met Ala Arg
            420                 425                 430

Leu Ala Ala Ala Arg Lys Glu Pro Thr Pro Pro Ala Ser Asn Ser Ser
            435                 440                 445

Glu Ser Leu His Leu Ser Phe Gly Gly Val Ser Met Ser Leu Gly Ser
        450                 455                 460

Ile Phe Asp Gly Glu Thr Ala Arg Gln Ala Ala Val Gln Pro Leu Ala
465                 470                 475                 480

Thr Gly Pro Thr Asp Val Pro Met Ser Phe Gly Ser Phe Ser Asp Gly
                485                 490                 495

Glu Ile Asp Glu Leu Ser Arg Arg Val Thr Glu Ser Glu Pro Val Leu
                500                 505                 510

Phe Gly Ser Phe Glu Pro Gly Glu Val Asn Ser Ile Ile Ser Ser Arg
            515                 520                 525

Ser Ala Val Ser Phe Pro Leu Arg Lys Gln Arg Glu Glu Phe Glu Ala
530                 535                 540

Phe Val Ala Gln Gln Gln Arg Phe Asp Ala Gly Ala
545                 550                 555
```